US010265292B2

(12) United States Patent
Doane et al.

(10) Patent No.: US 10,265,292 B2
(45) Date of Patent: Apr. 23, 2019

(54) TERPENE-BASED COMPOSITIONS, PROCESSES METHODOLOGIES

(71) Applicant: The Werc Shop, LLC, Pasadena, CA (US)

(72) Inventors: Braden Doane, Bellevue, WA (US); Jeffrey Charles Raber, Pasadena, CA (US)

(73) Assignee: The Werc Shop, LLC, Monrovia, CA (US)

( * ) Notice: Subject to any disclaimer, the term of this patent is extended or adjusted under 35 U.S.C. 154(b) by 5 days.

(21) Appl. No.: 15/014,716

(22) Filed: Feb. 3, 2016

(65) Prior Publication Data

US 2016/0151328 A1    Jun. 2, 2016

Related U.S. Application Data

(63) Continuation-in-part of application No. 14/467,565, filed on Aug. 25, 2014.

(Continued)

(51) Int. Cl.
| A61K 31/352 | (2006.01) |
| A61K 47/02 | (2006.01) |
| A61K 47/10 | (2017.01) |
| A61K 47/14 | (2017.01) |
| G01N 30/02 | (2006.01) |

(Continued)

(52) U.S. Cl.
CPC ............ *A61K 31/352* (2013.01); *A24B 15/16* (2013.01); *A24B 15/167* (2016.11); *A24F 47/008* (2013.01); *A61K 47/02* (2013.01); *A61K 47/10* (2013.01); *A61K 47/14* (2013.01); *A61Q 13/00* (2013.01); *C11B 9/0007* (2013.01); *C11B 9/0015* (2013.01); *C11B 9/0034* (2013.01); *C11B 9/0038* (2013.01);

(Continued)

(58) Field of Classification Search
CPC .................................................... A61K 31/352
See application file for complete search history.

(56) References Cited

U.S. PATENT DOCUMENTS

| 4,957,744 A * | 9/1990 | della Valle ............. A61K 8/735 |
| | | 424/401 |
| 2003/0152649 A1 * | 8/2003 | Frame .................. A61K 31/015 |
| | | 424/725 |

(Continued)

OTHER PUBLICATIONS

Cannabidiol (CBD) Pre-Review Report Agenda Item 5.2, Expert Committee on Drug Dependence, Thirty-ninth Meeting, Geneva Nov. 6-10, 2017, World Health Organization.

(Continued)

*Primary Examiner* — Arrie L Reuther
(74) *Attorney, Agent, or Firm* — Patnstr, APC; Tom Brody; Peter Jon Gluck, Esq.

(57) ABSTRACT

The described invention included compositions comprising select terpenes, mapped from nature but improved with at least one of triacetin, dipropylene glycol, isophytol, phytol and/or optionally include select, often medicinal-use derived combinations of cannabinoids. The compositions and devices have a variety of uses, such as for vaporization and inhalation, and for use as personal lubricants, and the like synthetic creations of which appear to mimic or improve upon natural phenomena, and while being highly inspired by the same, remain empirically and non-obviously distinct from the same.

25 Claims, 2 Drawing Sheets

Related U.S. Application Data

(60) Provisional application No. 62/147,847, filed on Apr. 15, 2015, provisional application No. 62/147,848, filed on Apr. 15, 2015.

(51) Int. Cl.
*A24F 47/00* (2006.01)
*A24B 15/16* (2006.01)
*C11B 9/00* (2006.01)
*A61Q 13/00* (2006.01)

(52) U.S. Cl.
CPC .......... *C11B 9/0046* (2013.01); *C11B 9/0049* (2013.01); *C11B 9/0053* (2013.01); *G01N 30/02* (2013.01)

(56) References Cited

U.S. PATENT DOCUMENTS

| | | | |
|---|---|---|---|
| 2008/0008667 A1* | 1/2008 | Hoke | A61K 8/922 424/58 |
| 2011/0091404 A1* | 4/2011 | Wohrle | A61K 8/37 424/70.1 |
| 2012/0202891 A1* | 8/2012 | Stinchcomb | A61K 9/0014 514/733 |
| 2016/0346339 A1* | 12/2016 | Finley | A61K 31/355 |

OTHER PUBLICATIONS

The Werc Shop, Does the Source of Terpenes Matter? Whitepaper, Apr. 2018, www.TheWercShop.com, 10 pages, Apr. 2018.

* cited by examiner

TERPENE-BASED COMPOSITIONS, PROCESSES METHODOLOGIES

CROSS REFERENCE TO RELATED APPLICATION

This application is a continuation-in part of U.S. patent application Ser. No. 14/467,565, filed Aug. 25, 2014, (which claims the benefit of and priority to U.S. provisional patent application No. 61/879,281, filed Sep. 18, 2013), and Likewise claims the priority of U.S. provisional patent application No. 62/147,847 (Apr. 15, 2015), 62/147,848 (Apr. 15, 2015) and 62/282,431 (Jul. 31, 2015). The contents of each of these applications is incorporated by reference herein in its entirety, along with PCT/US2014/064860 and ISR WO 2015/070167 as if expressly set forth and is owned by a Common Assignee.

FIELD OF THE DISCLOSURE

The present disclosure relates to compositions including either triacetin, dipropylene glycol, isophytol and/or phytol with selected terpenes. The terpenes are selected to produce a pleasing fragrance when the compositions are used and/or to improve the bioavailability or potency of other compounds delivered in the compositions, such as cannabinoids.

BACKGROUND OF THE DISCLOSURE

Terpenes are a class of chemical components comprised of the fundamental building block of isoprene. Typically known for their olfactory stimulation, they are commonly used in the manufacture of chewing gum, candies and mints. They are also recognized for their diverse biological activity, often being touted as components which synergize with other endogenous and exogenous ligands. They are also recognized as entourage compounds, meaning that they increase the effects of ligands that bind to some receptors, while the compounds, themselves, have little affinity for the receptor.

Terpenes naturally are biosynthesized from units of isoprene, which can be linked to form linear chains or rings. In increasing length, the terpenes include hemiterpenes (single isoprenoid unit), monoterpenes (two units), sesquiterpenes (three units), diterpenes (four units), sesterterpenes (five units), triterpenes (six units), and so on. Terpenes are also known as terpenoids.

The fragrance of fruits and flowers is primarily due to aerosolized terpenes that are registered by the olfactory receptor neurons in the nose. In citrus fruits, the major aromatic compounds are limonene (LIM) and eucalyptol (EUC), which are both terpenes. The aromatic compounds of clove oil include eugenol and beta-caryophyllene (BCP), which are terpenes. The aromatic compounds of peppermint include LIM, menthone, and menthol, which are all terpenes.

The terpene composition of a sample, e.g., a plant, flower fruit, etc. can be analyzed with analytical tools, such as chromatography or mass spectrometry. Nonetheless, establishing the actual type and amount of terpene in a sample can be difficult because there may be hundreds of different terpenes in a sample, and terpenes with very different properties may differ by only the stereochemistry at a single carbon atom. See, for example, the well-known difference between R-(−)-carvone, which smells like spearmint, and S-(+)-cavone, which smells like caraway. Accordingly, determining the type and amount of each terpene in a sample will often require the use of complimentary analytical techniques, such as LC-MS and GC-MS.

SUMMARY OF THE DISCLOSURE

The present disclosure provides a composition that contains a combination of triacetin, dipropylene glycol, isophytol, and/or phytol and at least two terpenes. The compositions find a variety of uses, such as vaporizable inhalants, oral and sublingual compositions, topical compositions, and personal lubricants. In many instances, the compositions will include more than two terpenes. In exclusionary embodiments, the compositions can exclude one or more of any terpenes and/or related plant materials, depending on intended applications. The exclusion of certain terpenes may improve the fragrance and/or the performance of the composition.

The terpenes may be selected from a list comprising alpha-bisabolol, borneol, camphene, camphor, beta-caryophyllene, delta-3-carene, caryophyllene oxide, alpha-cedrene, beta-eudesmol, fencholfenchyl alcohol, geraniol, guaiol, alpha-humulene, isoborneol limonene, linalool, menthol, myrcene, nerol, nerolidol, cis-ocimene, trans-ocimene, alpha-phellandrene, alpha-pinene, beta-pinene, sabinene, 4-thujanol, alpha-terpinene, alpha-terpineol, terpinolene, alpha-guaiene, elemene, farnesene, farnesol, germacrene B, guaia-1(10),11-diene, trans-2-pinanol, selina-3,7(11)-diene, eudesm-7(11)-en-4-ol, and valencene.

The present disclosure provides compositions, comprising novel combinations of terpenes that mimic the fragrance of plant matter that is fresh, processed, or dried. Also provided are novel combinations of terpenes that mimic a documented emotional response that is conferred by the processed or dried plant matter, or provides any number of utilitarian benefits, real or perceived. Also described are methods for determining the composition of terpenes in a sample, including the type and amount of terpenes. Once the terpene composition of a sample is determined, the identified blend of terpenes can be reconstructed to achieve the desired fragrance or other properties. In some embodiments, certain terpenes may be left out of the composition.

Compositions comprising either triacetin, dipropylene glycol, isophytol and/or phytol and at least two terpenes may additionally comprise a cannabinoid. The cannabinoids may be selected from the group consisting of tetrahydrocannabinol, delta-9-tetrahydrocannabinol (THC), delta-8-tetrahydrocannabinol, delta-9-tetrahydrocannabinol propyl analogue (THCV), cannabidiol (CBD), cannabidiol propyl analogs (CBDV), cannabinol (CBN), cannabichromene (CBC), cannabichromene propyl analogs (CBCV) and cannabigerol (CBG) or their corresponding cannabinoid acid counterparts. In some embodiments, the compositions will comprise between 2 and 85% (wt/wt) of cannabinoids, e.g., around 10%, around 15%, around 20% cannabinoids. In some embodiments, the compositions will specifically exclude cannabinoids.

In some embodiments, the combination of a cannabinoid with a formulating agent provides a desirable applicant formulation that can be specifically quantified and reproducibly produced. Additional exemplary implementations of the present disclosure share and are based upon the principle that the combination of a terpene with a formulating agent provides a functional desirable formulation that can be appealing to the sensory system, additionally as a physiologically functional agent, and can be specifically quantified and prepared in a reproducible fashion. In preferred embodiments, such formulations may serve to be compatible with latex and possess qualities exhibiting a slippery tactile sensation, providing for effective use as a sexual lubricant. In other preferred embodiments, a composition comprising terpenes in triacetin, dipropylene glycol, isophytol, and/or phytol, form a uniform and homogeneous solution that can be vaporized in consistent fashion without adulteration of taste of the specific terpene composition in an electronic cigarette cartridge or other device designed to facilitate inhalation of vapors.

The compositions of the invention may additionally include other delivery agents in addition to triacetin, dipropylene glycol, isophytol and/or phytol, such as diethyl phthalate, tributyrin, isoparaffins, paraffins, silicone oils, perfluorinated aliphatic ethers, glycol ethers, glycol ether esters, medium chain triglycerides, esters, ketones, polyethylene glycol, ethanol, cyclodextrin, hydroxymethyl cellulose, hydroxyethyl cellulose, hydroxypropyl cellulose, carboxymethyl cellulose, dimethicone, or cyclomethicone. In some embodiments, terpenes, such as NDL or LIM, act as delivery agents.

In an embodiment, the invention comprises a prepared composition of terpenes comprising BCP, LIM, and myrcene (MYR), wherein the composition has a detectable fragrance. The fragrance can be detected, for example, by a human olfactory system or a synthetic nose.

Also provided is a composition comprising BCP, LIM, MYR, alpha-pinene (API), and linalool (LIN), wherein the terpenes are present in approximately equal percentages by weight (wt %).

In another embodiment, the invention provides a composition comprising BCP at about 10-30 wt %, LIM about 5-45 wt %, and MYR at about 5-30 wt %; and wherein the sum of all terpenes in the composition is up to 100 wt %.

In an embodiment, the present disclosure provides a composition comprising a terpene formulation, wherein the terpene formulation consists of BCP, LIM, MYR, and at least one other terpene, wherein the composition does not contain 3,3'-dihydroxy-5,4'-dimethoxybibenzyl, wherein the terpene formulation is the only source of terpenes in the composition, and wherein the BCP, LIM, and MYR together comprise at least 25% (wt./vol.) of the terpene formulation, or at least 30%, at least 35%, at least 40%, at least 45%, at least 50%, at least 55%, at least 60%, at least 65%, at least 70%, at least 75%, at least 80%, at least 85%, at least 90%, of the terpene composition.

In another embodiment, the composition comprises a modifier. The modifier (described in more detail below) may comprise a thiol, an ester, a ketone, an aldehyde, a cannabinoid, another compound, or any combination thereof.

In an exclusionary embodiment, the invention provides any of the above compositions, wherein the composition does not contain 3,3'-dihydroxy-5,4'dimethoxybibenzyl. In another exclusionary embodiment, the invention provides any of the above compositions, wherein the composition does not contain cellulose. In another exclusionary embodiment, the invention provides any of the above compositions, wherein the composition does not contain chlorophyll. In another exclusionary embodiment, the composition does not include ledol. In another exclusionary embodiment, the composition does not include alpha-terpinene. In another exclusionary embodiment, the composition does not include camphor.

Also provided is any of the above compositions, wherein the each terpene is either purified from a natural source or is synthetic.

Also provided is a composition wherein the terpene formulation consists of BCP, LIM, MYR, API, and LIN. Also provided is the above composition, wherein the terpene formulation consists of BCP, LIM, MYR, beta-pinene (BPI), and LIN. Also provided is the above composition, wherein the terpene formulation consists of BCP, LIM, MYR, and terpinolene (TER). Also provided is the above composition, wherein the terpene formulation consists of BCP, LIM, MYR, TER, and BPI. Also provided is the above composition, wherein the terpene formulation comprises nerolidol (NDL), farnesol (FOL), and LIM. Also provided is the above composition, wherein the terpene formulation comprises NDL, FOL, LIM, EUC, LIN, and geraniol (GER).

In embodiments that refer to the tables, what is provided is a composition comprising a formulation that includes one of the terpene trios that are disclosed in Tables 2-37, wherein the terpene formulation is the only source of terpenes in the composition, wherein the terpene trio accounts for at least 25% of the terpenes of the formulation (or at least 45%, at least 50%, at least 55%, at least 60%, at least 65%, at least 70%, at least 75%, at least 80%, at least 85%, at least 90%, at least 95%), and wherein each terpene is either purified from a natural source or is synthetic. Also provided is the above composition, wherein the terpene trio accounts for at least 70% of the terpenes of the formulation. Further provided is the above composition, wherein the terpene trio accounts for at least 80% of the terpenes of the formulation.

Also provided is the above composition, wherein the formulation does not contain any terpene in addition to the terpenes in the terpene trio. Moreover, what is embraced is the above composition, wherein the terpene trio is BCP, LIM, and MYR. In yet another embodiment, what is provided is the above composition, wherein the terpene trio is BCP, LIM, and MYR, and wherein the formulation additionally comprises: (i) BPI, or (ii) LIN, or (iii) both BPI and LIN.

Further provided is the above composition, wherein the terpene trio is BCP, LIM, and MYR, and wherein the formulation additionally comprises BPI and TER, and does not include LIN. Further provided is the above composition, that comprises MYR, API, and: (i) BPI; or (ii) BCP; or (iii) both BPI and BCP. In exclusionary embodiments, what is provided is the above composition that does not contain more than four terpenes being each of less than 50% purity, of less than 60% purity, of less than 70% purity, of less than 80% purity, of less than 90% purity of less than 95% purity or of less than 99% purity. Moreover, what is provided is the above composition that does not contain more than five terpenes.

In device embodiments, what is provided is a container comprising one of the above-disclosed compositions. The container may be configured to deliver the composition as a spray, in drops, as an ointment, or as a cream. In some embodiments the container will be configured to deliver the composition to a heating element, for example the heating element within a vaporizing device such as an electronic cigarette or pipe.

In a methods embodiment, what is provided is a method for applying a fragrance, the method comprising providing a composition of terpenes, contacting an olfactorily detectable quantity of the composition with the atmosphere, and causing a human olfactory system or electronic nose to detect the presence of the composition in the atmosphere. The method may further comprising contacting the olfactorily detectable quantity of composition with a carrier substance, which may comprise a perfume, incense, cosmetic, moisturizer, emollient, toiletry, edible substance, inhalable substance, electronic cigarette liquid, diffuser substance, sticker substance or candle.

In a methods embodiment, what is provided is a method for using one of the above compositions, comprising the step of contacting the composition with the atmosphere, the step of allowing a detectable quantity of vaporize and migrate into the atmosphere, and the step of inhaling by a human subject of at least a portion of the detectable quantity, wherein the detectable quantity can be detected by one or both of an olfactory system or by a synthetic nose.

In other embodiments, what is provided is an apparatus for dispensing at least a fragranced terpene-based composition according to any claims, tables, and the specification, including said terpene-based fragranced composition disposed or effective to be emplaced therein. In a process embodiment, what is provided is a process to impart any terpene-based fragranced compositions in whole, or in part to a perfume, flavor material, incense, cosmetic or toiletry, according to any claims, tables, and the specification above. In a system embodiment, what is provided is a system for repelling or attracting olfactorily sentient organisms based upon the claims, tables, and the specifications above. In another system embodiment, what is provided is a system for addressing the masking of odors, according to any claims, tables, or disclosures herein comprised of at least one prepared version of a terpene-based composition. In products by process embodiments, what is provided is a products by processes of any claims herein. Moreover, what is provided is a product, according to the tables and specification herein, for treating mammals in need thereof.

In embodiments, what can be excluded is any composition, any formulation, any composition containing said formulation, and related methods, wherein the composition is a fluid (or comprises mainly fluid, or where about 80% of the entire composition is fluid, or where about 60% of the entire composition is fluid, or where about 40% of the entire composition is fluid), and wherein the fluid component of the composition contains less than 10% (wt./vol.), less than 1.0%, less than 0.5%, less than 0.2%, less than 0.1%, less than 0.05%, less than 0.02%, less than 0.01%, less than 0.005%, less than 0.002%, less than 0.001%, less than 0.0005%, less than 0.0002%, less than 0.0001%, less than 0.00001%, less than 0.000001%, less than 0.0000001%, and the like, 3,3'-dihydroxy-5,4'-dimethoxybibenzyl. Also, what can be excluded is a composition where the fluid component of the composition contains detectable 3,3'-dihydroxy-5,4'-dimethoxybibenzyl, and where the detectable 3,3'-dihydroxy-5,4'-dimethoxybibenzyl occurs at a concentration that is less than 1.0%, less than 0.5%, less than 0.2%, less than 0.1%, less than 0.05%, less than 0.02%, less than 0.01%, less than 0.005%, less than 0.002%, less than 0.001%, less than 0.0005%, less than 0.0002%, less than 0.0001%, less than 0.00001%, less than 0.000001%, less than 0.0000001%, and the like.

The above exclusionary embodiments can also apply to one or more other chemicals, such as terpenes or non-terpenes.

Moreover, what is embraced is the above composition wherein the terpene formulation consists of about 50% (wt./vol.) MYR, about 15% (wt./vol.) API, and about 35% (wt./vol.) BCP, and wherein the sum of the % equals up to 100%. Also embraced is the above composition, comprising a formulation that includes one of the terpene trios that are disclosed in Tables 2-37, wherein the terpene formulation is the only source of terpenes in the composition, wherein the terpene trio accounts for at least 60% of the terpenes of the formulation, and wherein each terpene is either purified from a natural source or is synthetic. Table 1 is a legend that correlates the number used to refer to a terpene, with the actual name of the terpene.

Moreover, what is encompassed is the above composition, wherein the terpene trio accounts for at least 70% of the terpenes of the formulation. Also embraced is the above composition, wherein the terpene trio accounts for at least 80% of the terpenes of the formulation.

Further provided is the above composition, wherein the formulation does not contain any terpene in addition to the terpenes in the terpene trio. Additionally encompassed is the above composition, wherein the terpene trio is BCP, LIM, and MYR. Further provided is the above composition, wherein the terpene trio is BCP, LIM, and MYR, and wherein the formulation additionally comprises: (i) BPI, or (ii) LIN, or (iii) both BPI and LIN.

In embodiments that limit the number of terpenes, what is provided is each and every one of the above compositions, wherein the composition does not contain more than four terpenes, wherein the composition does not contain more than five terpenes, wherein the composition does not contain more than six terpenes, and so on.

In device embodiments, what is provided for each of the above-disclosed compositions, that is, provided separately for each and every one of the above compositions, is a device that comprises the composition. The device can be a holder, a vial, a bottle, a canister, a paper wrapper, a foil wrapper, a plastic wrapper, and so on. The device can be a wax candle, a container or wrapper that comprises a soap, a container that comprises a perfume, a container that comprises a cosmetic cream, an electronic cigarette, a scratch and sniff device, a passive diffusion device, an edible substance, a tincture, or a container holding a pressurized or gelatin based composition that is configured for aerosol dispersal.

Also provided is a process for generating a library of prepared terpene compositions, the process comprising: obtaining a sample; analyzing the chemical profile of the sample to identify terpenes in the sample; quantifying the terpenes identified; and preparing a blend of terpenes based on those quantities. The sample can be from any plant or other natural product, including *Cannabis sativa* L., *Humulus lupulus*, or ether plants. The analysis step may comprise separating substances from a mixture, genetic analysis, chemotaxonomic analysis, compound extraction, gas chromatography flame ionization detection, chemical formula identification, chromatography, or any other analytical chemistry technique known in the art. Terpenes identified can be those listed in Tables 1-37 below, or any other terpene. Terpenes may be quantified based on their mass fraction, percent weight, mole fraction, percentage by volume, or the like. The prepared blend may comprise all natural terpenes, all synthetic terpenes, or a combination thereof.

Also provided is a database or library of terpene compositions produced by the above process.

The present disclosure encompasses all possible combinations of the above embodiments, and encompasses all possible disclosures of each independent claim with its dependent claims. For example, what is encompassed is an invention that is the combination of: claim 1+claim 2; or the combination of: claim 1+claim 2+claim 3; or the combination of claim 1+claim 3+claim 4; or the combination of claim 1+claim 2+claim 3+claim 4; and the like.

DETAILED DESCRIPTION

Figure 1:
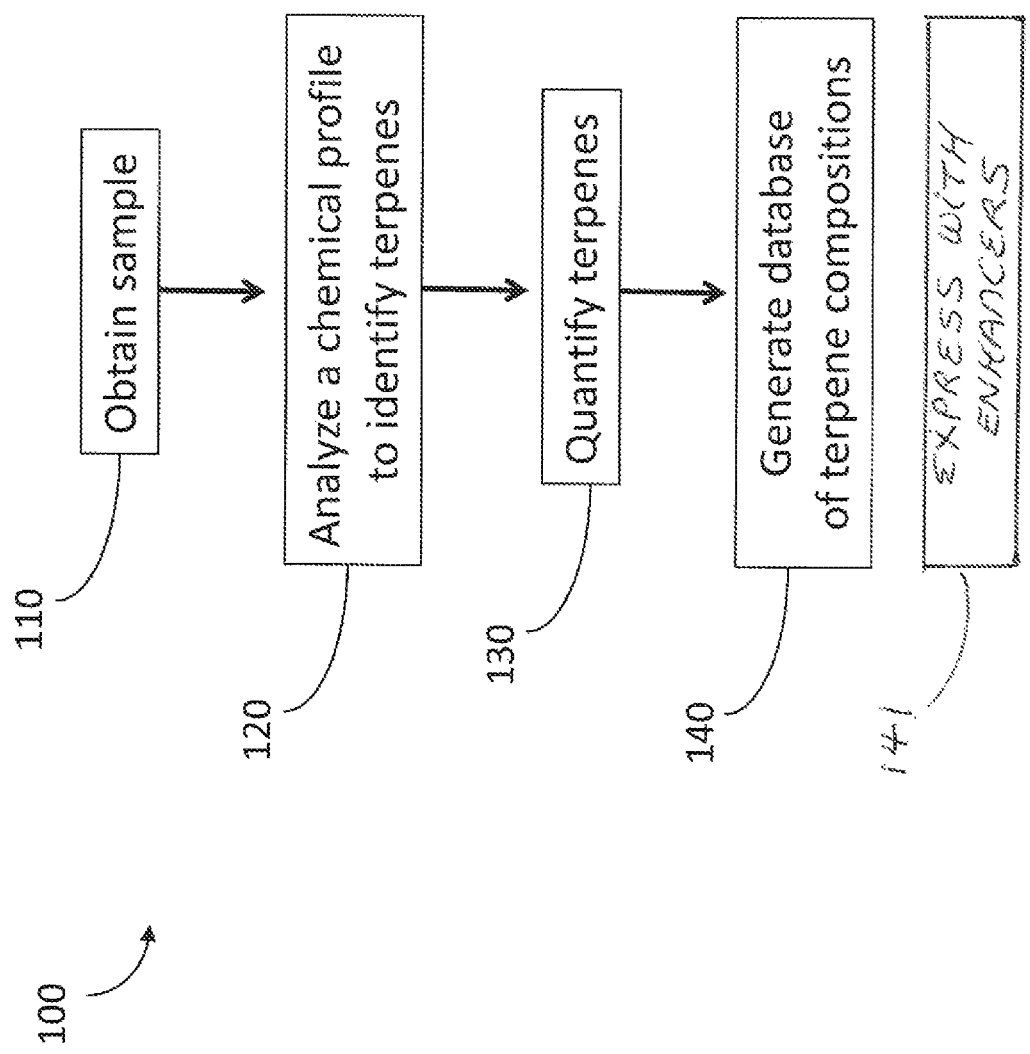
FIG. 1 shows a method for generating a library of prepared terpene compositions.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

The terms "adapted to," "configured for," and "capable of," mean the same thing. Where more than one of these terms are used in a claim set, it is the case that each and every one of these terms, as they might occur, means, "capable of."

An "agonist" is a compound that stimulates an increase in a biochemical or physiological activity. The activity can be the rate of ion transport by an ion channel, rate of signal transmission by a receptor such as a G-protein-linked receptor, rate of secretion of a substance from a cell, enzymatic activity, genetic expression, and so on.

An "antagonist" is a compound that reduces or inhibits a biochemical or physiological activity. For a compound to be an antagonist, it is not necessary that there exist any known agonist, and it is not necessary that the antagonist work by reducing the activity of a corresponding agonist. Likewise, the present inventors have discovered that a composition which contains a combination of additional helpful moieties, defined herein as "enhancers", namely triacetin, dipropylene glycol, isophytol, and/or phytol works better for uses defined within this application and its incorporated family than expected or shown in nature.

Some examples of terpenes, and their classification, are as follows:

Hemiterpenes: Examples of hemiterpenes, which do not necessarily have an odor, are 2-methyl-1,3-butadiene, hemialboside, and hymenoside;

Monoterpenes: pinene, alpha-pinene, beta-pinene, cis-pinene, trans-pinane, cis-pinanol, trans-pinanol (Erman and Kane (2008) Chem. Biodivers. 5:910-919), limonene; linalool; myrcene; eucalyptol; alpha-phellandrene; beta-phellandrene; alpha-ocimene; beta-ocimene, cis-ocimene, ocimene, delta-3-carene; fenchol; sabinene; borneol, isoborneol, camphene, camphor, phellandrene, alpha-phellandrene, alpha-terpinene, geraniol, linalool, nerol, menthol, myrcene, terpinolene, alpha-terpinolene, beta-terpinolene, gamma-terpinolene, delta-terpinolene, alpha-terpineol, and trans-2-pinanol.

Sesquiterpenes: caryophyllene, caryophyllene oxide, humulene, alpha-humulene, alpha-bisabolene; beta-bisabolene; santalol; selinene; nerolidol, bisabolol; alpha-cedrene, beta-cedrene, beta-eudesmol, eudesm-7(11)-en-4-ol, selina-3,7(11)-diene, guaiol, valencene, alpha-guaiene, beta-guaiene, delta-guaiene, guaiene, farnesene, alpha-farnesene, beta-farnesene, elemene, alpha-elemene, beta-elemene, gamma-elemene, delta-elemene, germacrene, germacrene A, germacrene B, germacrene C, germacrene D, and germacrene E.

Diterpenes: oridonin, phytol, and isophytol.

Triterpenes: ursolic acid, oleanolic acid;

"1.5 ene": guaia-1(10),11-diene can be characterized as 1.5 ene. Guaia-1(10),11-diene is halfway between a monoterpene and diterpene, in terms of how many isoprenoid units are present. Monoterpene is $C_{10}H_{16}$, and diterpene is $C_{20}H_{32}$. Guaia-1(10),11-diene is $C_{15}H_{24}$. Isoprene is $C_5H_8$ (two double bonds).

In "comprising" embodiments, the present disclosure provides a formulation that comprises a fluid that is a transparent liquid, a translucent liquid, an opaque liquid, a slurry, an emulsion, a suspension, a gel, and the like. In "consisting" embodiments, the present disclosure provides a formulation that consists of a fluid that is a transparent liquid, a translucent liquid, an opaque liquid, a slurry, an emulsion, a suspension, a gel, and the like. The designation of liquid, slurry, emulsion, gel, and so on, refers to this characterization as determined at room temperature (about 23 degrees centigrade).

The cannabinoid receptors include CB1 and CB2. CB1 and CB2 are members of the G protein-coupled receptor family. The ligands of $CB_1$ include delta-9-tetrahydrocannabinol (THC), as well as an endogenous ligand, N-arachidonyl ethanolamide (AEA; anandamide). In addition to CB1 and CB2, cannabinoids can bind to "receptors" such as various ion channels, such as vanilloid (TRPV) receptors, and to nuclear receptors, such as peroxisome proliferator-activated receptor (PPAR) (Console-Bram et al. (2012) Prog. Neuropsychopharmacol. Biol. Psychiatry. 38:4-15). Biochemical properties of terpenes, including receptor binding, can be assessed using labeled terpenes and labeled ligands where a terpene influences binding properties of the labeled ligand. Useful labels include 32P, 33P, 35S, 14C, 3H, 125I, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

The ability of a compound, such as a terpene, to serve as an agonist, an antagonist, to synergize with another compound, or to function as an entourage compound, can be assessed by a number of assay methods. Methods for determining binding to cells or subcellular particles that express a cannabinoid receptor have been described (Leggett et al. (2004) Br. J. Pharmacol. 141:253 262). Leggett et al., supra, determined that a fatty acid amide (oleamide) can activate cannabinoid receptor CB1.

Endocannabinoids are compounds produced by the body which activate cannabinoid receptors. Anandamide and 2-acylglycerolarachidonic acid are considered endocannabinoids.

Phytocannabinoids, also called natural cannabinoids or herbal cannabinoids, are compounds produced by botanicals, most commonly *Cannabis sativa* L. and are often found in both carboxylated, acidic, and neutral forms, such as cannabidiolic acid (CBDA) and cannabidiol (CBD), respectively. Neutral phytocannabinoids can be derived from heating cannabinoid acids to perform the event referred to as decarboxylation. Various cultivars of *Cannabis sativa* L. can produce varying cannabinoid ratios and unique and diverse cannabinoid profiles, with their cannabinoids being produced in the trichomes of the plant, often in a sticky resinous form comprised with associated terpenes. These components are cytotoxic to the plant and are thus produced and stored in the trichomes to ward of predators and used in chemical botanical warfare.

"Synergy" refers to the phenomenon where a first compound stimulates a first level of a particular activity, where a second compound stimulates a second level of the same particular activity, and where the presence of both compounds results in a third level of the same particular activity, where the third level is greater than the additive sum of the first level and the second level. Synergy can occur where the first compound and second compound are used at the same time, or where the first compound and second compound are used sequentially.

"Entourage compound" is a compound that can increase the effects of one or more naturally-occurring ligands that bind to one or more receptors, but that has little or no affinity for the receptor. In a preferred, but non-limiting embodiment, an entourage compound increases the effects of a naturally-occurring ligand that binds to one or more cannabinoid receptors, but that has little or no affinity for the cannabinoid receptor.

Terpenes can be acquired commercially, in various purities, and are useful biochemical agents for a variety of olfactory and physiologically stimulating purposes. There are suppliers of terpenes that are pure and homogeneous, contract laboratories that synthesize terpenes, and contract laboratories that purify terpenes from natural products, e.g., essential oils, are available (see, e.g., Sigma-Aldrich, St. Louis, Mo.; TCI America, Portland, Oreg.; Arizona Chemical, Jacksonville, Fla.). Without implying any limitation, the term "pure" can refer to a terpene that is over 95% pure, over 98% pure, over 99% pure, over 99.5% pure, over 99.9% pure, over 99.99% pure, and the like. Generally, the term "pure" does not take into account any solvent that may be used for dissolving the terpene, such as a solvent that is ethanol, acetone, tetrahydrofuran, and so on. In other words, unless specified otherwise, either explicitly or by the context, any solvent that is present is not relevant to the characterization of a given terpene as pure and homogeneous.

Biochemical Assays for Entourage Compounds

The ability of a compound, such as a terpene, to serve as an agonist, an antagonist, to synergize with another compound, or to function as an entourage, compound, can be assessed by a number of assay methods. Methods for determining binding to cells or subcellular particles that express a cannabinoid receptor have been described (Leggett et al. (2004) Br. J. Pharmacol. 141:253-262). Leggett et al., supra, determined that a fatty acid amide (oleamide) can activate cannabinoid receptor CB1.

Human Sensory Panel for Odors; Correlating Odors with Chemical Quantitation of Odiferous Compounds At least the following methods are available for use in the present disclosure. Human panels have been trained to evaluate odors, such where the odors had the names, grassy green, green spicy, sweet, seasoned, sharp, soupy, mellow, metallic, fragrant fruity, cardboard-like, and complex (Kurobayashi et al. (2006) Biosci. Blotechnol. Biochem. 70:958-965). The Kurobayashi et al., supra, study included detection of odor of terpenes, e.g., myrcene. Human panels have been trained to evaluate the level of odorants, including terpenes (linalool; L-carvone) on a scale of zero (extremely mild) to ten (extremely intense). Odorants were delivered to human subjects using an air stream. The subjects receiving the odorants, and providing subjective responses on odor intensity, also provided objective responses using electroolfactograms (EOG). The EOG test involved placing electrodes on the contralateral bridge of the nose, earlobe, and mastoids.

A variety of physiological parameters have been tested, in studies of subject response to terpenes, e.g., linalool. These parameters include blood oxygen saturation, pulse rate, breathing rate, eye-blinks, skin conductance, skin temperature, and surface electromyogram (Heuberger et al. (2004) Neuropsychopharmacology. 29:1925-1932). Various subjective parameters have also been tested, in subject response to terpenes, including subjective attentiveness, mood, cheerfulness, subjective relaxation, vigor, calmness, and alertness (see, e.g., Heuberger et al (2004) Neuropsychopharmacology. 29:1925-1932; Diego et al. (1998) Int. J. Neurosci. 96:217-224; Knasko (1992) Chem. Senses. 17;27-35). Sugawara's group (Sugawara et al. (1998) J. Home Econ. Jpn. 49:1281-1290; Sugawara et al. (2013) Molecules. 18:3312-3338; Satoh and Sugawara (2003) Analytical Sciences. 19:139-146), have used sensory tests for assessing subjective responses to variety of terpene-containing oils. The terpene-containing oils were tested for subjective impressions, that is, fresh-stale, soothing-activating, airy-heavy, plain-rich, natural-unnatural, elegant-unrefined, soft-strong, pleasant-unpleasant, warm-cool, comfortable-uncomfortable, woodsy-not woodsy, floral-peppery, lively-dull. Sugawara's group also provided methods for the statistical analysis of data on subjective response, for example, calculation of the p value. These investigators also acquired electroencephalography data. Odorant was administered by a 300 mL inhaler flask, where 0.02 to 0.2 mL of odorant was applied to a strip of filter paper placed at the bottom of the flask.

(Moss et al. (2008) Intern. J. Neuroscience. 118:59-77), discloses tests for assessing various psychological responses to aromas such as peppermint odor. The tests include those for alertness, calmness, contentedness, immediate word recall, ability to match digits quickly, memory of details of a picture of a 3-dimensional house, and time to respond by pressing yes or no in order to match a screen that displays either "yes" or "no."

Fragrance Panels with Human Subjects

Odorants, volatile chemicals, and fragrances can be administered by various devices, e.g., Aroma-Stream (Tisserand, Hove, Sussex, England), H2EO Aircare Ultrasonic Diffuser (Aromatics International, Lolo, Mont.), ZAQ NoorAir Aromatherapy Essential Oil Diffuser (Enovize, Inc., Skokie, Ill.).

Detecting the presence of odiferous chemicals, as well as the quantification of one or more odiferous chemicals, can be assessed by the human nose. Quantification can be in terms of, for example, micrograms/liter of air, nanograms/L of air, picograms/L of air, femtograms/L of air, attograms/L of air, and so on. Also, quantification can be in terms of micromoles/liter of air, nanomoles/L of air, picomoles/L of air, femtomoles/L of air, attomoles/L of air, and so on. The skilled artisan is able to quantify the concentrations of various volatile compounds, by way of odor. For example, 2,4,6-trichloroanisole (TCA) can be detected by way of smell, when it exists at a concentration of a few nanograms/L of air (H. Rudy. Gerstel Solutions Worldwide, No. 11, pages 9-11). To give another example, the lower limit of detection of formaldehyde in the air has been determined to be 0.03-1.0 milligrams formaldehyde per cubic meter of air (Salthammer et al. (2010) Chem. Rev. 110:2536-2672).

Sensory panels with human subjects are used to identify odors, including odors of degradation products of polypropylene and polyethylene. These degradation products can include aldehydes, ketones, carboxylic acids, alcohols, and lactones. Studies have demonstrated the correlation of human odor perceptions with chemical quantitation by mass spectroscopy and gas chromatography (Hopfer et al (2012) Anal. Bioanal. Chem. 402:903-913). Human sensory panels have been used for detecting and quantifying a variety of organic chemicals (see, e.g., Johnson et al (2012) PLoS ONE. 7:e32693 (7 pages); Zhou et al (1999) J. Agric. Food Chem. 47:3941-3953; Brattoli et al (2011) Sensors (Basel). 11:5290-5322).

Synthetic Nasal Devices

Synthetic nasal devices, including electronic nose devices are available. See for example, Cyranose® 320, Sensigent, Baldwin Park, Calif.; Arshak et al (2004) Sensor Review. 24:181-198; Monge et al (2004) Comb. Chem. High Throughput Screen. 7:337-344; Ye et al (2011) J. Pharm. Biomed. 55:1239-1244; Hodgins et al (1995) J. Automat. Chem. 17:179-185.

Classification of a Chemical or Oil by Fragrance Notes

The present disclosure encompasses terpene formulations that can be characterized by one or more of the following sensory terms, that is: citrus, citrus peel, lemon, lemon rind, lime, grapefruit, grapefruit peel, fruity, creamy, nut-like, melon, berry, seedy, strawberry, cranberry, pineapple, floral, earthy, wood, pine, woody/pine, herbal, tea-like, musty and cheesy aromas, raspberry, orange, acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, musk, sweet, balsamic, spicy, woody, heavy floral, cheesy, mandarin, ugli fruit; anise, cinnamon clove, basil, mint, lavender, lavandin, thyme, rosemary, geranium, roses, citronella, cypress, eucalyptus, peru balsam, camphor, sandalwood, ylang, cedarwood, amyris oil, cedarwood oil, cocoa absolute, copaiba balsam, menthe oil pays, myrrh resin, patchouli oil, vanillin, and vetiver oil. See, US 2010/0111880 of Chen, U.S. Pat. No. 7,534,460 of Dewis, US 2009/0257973 of Fraser, which are each incorporated herein by reference in their entirety. The disclosure also encompasses compositions with a fragrance that has, e.g., bewitching, warm, powdery, slightly animal and velvety connotation (see, RE38,659 of Williams, which is incorporated by reference). Also encompassed are compositions with a fragrance that has, e.g., a green note, floral note, fruity note, chypre note, oriental note, leather note, tobacco note.

The present disclosure provides a formulation that contains a top note terpene, middle note terpene, and bottom note terpene. U.S. Pat. No. 6,769,428 of Cronk identifies terpenes that are top note (e.g., citronellal, citronellol, citronellyl acetate, dihydrolinalool, dihydromyrcenol, eucalyptol, geraniol, geranyl acetate, geranyl nitrile, hydroxycitronellal, limonene, linalool, linalool oxide, linalyl acetate, linalyl propionate, methyl anthranilate, alpha-methyl ionone, methyl nonyl acetaldehyde, menthone, isomenthone, myrcene, myrcenyl acetate, myrocenol, nerol, neryl acetate, alpha-pinene, beta-pinene, gamma-terpinene, alpha-terpineol, beta-terpineol, terpinyl acetate), middle note (e.g., coumarin, ethyl vanillin, eugenol, isoeugenol), and bottom note (e.g., hexyl cinnamic aldehyde).

The present disclosure provides terpene compositions that contain individual terpenes with a high volatility and low substantivity. Chemicals with a high volatility and low substantivity are used to give an initial burst of characters, such as light, fresh, fruity, citrus, green or floral, which are detected soon after application. Such materials are referred to, by the artisan skilled in the field of fragrances as "top notes". Less volatile, and more substantive, chemicals, at least in perfumes, are used to give characters such as musk, sweet, balsamic, spicy, woody or heavy floral to the fragrance oil which, although may also be detected soon after application, also last for longer. The skilled artisan refers to these materials as "middle notes" or "base notes". The skilled artisan can blend perfume raw materials so that the resultant fragrance oils have the desired overall fragrance character profile (see U.S. Pat. No. 7,208,464 of Heltovics, which is incorporated herein by reference in its entirety).

"Top note" fragrances are "fragrances having a high vapor pressure, and when applied to a paper sachet, vaporization takes place within 2 hours, and no scent remains. "Middle note" fragrances are "fragrances having a medium vapor pressure, and when applied to a paper sachet, the scent remains from about 2 to about 6 hours. "Base note" fragrances are fragrances having a low vapor pressure and high retentivity, and when applied to a paper sachet, the scent remains for more than about 6 hours. The terms "top note", "middle note", and "base note" are recognized by those skilled in the art of fragrance-containing compositions. See, U.S. Pat. No. 6,013,618 of Morelli, which is incorporated herein by reference in its entirety.

The present disclosure provides a formulation that comprises at least one terpene that provides a top note aroma, at least one terpene that provides a middle note aroma, and at least one terpene that provides a bottom note aroma. Also provided is a formulation that contains one or more terpenes that provides only a top note aroma. Also provided is a formulation that contains one or more terpenes that provides only a middle note aroma. Also provided is a formulation that contains one or more terpenes that provides only a bottom note aroma. Also provided is a formulation that contains only terpenes that provide a top note aroma and a bottom note aroma. Also provided is a formulation that contains only terpenes that provide a top note aroma and a middle note aroma. Also provided is a formulation that contains only terpenes that provide a middle note aroma and a bottom note aroma.

Modifiers

The present disclosure provides a composition that comprises a terpene formulation and one or more modifiers. As used herein, the term "modifier" refers to other classes of chemicals that are not terpenes. Chemicals such as thiols, esters, ketones, and aldehydes are potential modifiers. These compounds have distinct fragrances. The present invention contemplates using such other chemicals in conjunction with terpenes.

Thiols are organosulfur compounds that contain a carbon-boarded sulfhydryl group. They have pungent odors often resembling garlic.

Esters are organic compounds that occur naturally in fats and oils. They often have a pleasant fruity odor. They are responsible for the aromas of many fruits, including apples, bananas, and strawberries.

Some modifier compounds that are contemplated by the invention are 3-methyl-2-butene-1-thiol (sulfur compound) and hexanoic acid hexyl ester (pungent odor). Another modifier compound for use with the present invention is 2-heptanone, which is a naturally occurring compound in beer, bread, and some cheeses, and which has a banana-like odor.

Octanal and cis-4-decenal are aldehydes that have a fruit-like citrus odor. Either or both compounds can be used as modifiers with in the compositions of the disclosed invention.

Cannabinoids are another class of modifiers contemplated by the invention. Cannabinoids are a class of diverse chemical compounds that act on cannabinoid receptors in the brain. Many are produced naturally in the human body. Others known as phytocannabinoids are found in and on plants. Some commonly known phytocannabinoids include delta-9-tetrahydrocannabinol (THC) and cannabidiol (CBD). Cannabinoids can also be created synthetically.

The addition of cannabinoids of 40-99% purity to a composition of terpenes and propylene glycol emulsifies the terpenes in the mixture. Cannabinoids added at 10-70% act as an emulsifier.

Without implying any limitation, other modifiers can be selected from 4-hydroxy-2,5-dimethyl-3(2H)-furanone (strawberry), ethyl butyrate (apple, fruity), isoamyl acetate (banana), propyl hexanoate (pineapple, fruity), allyl hexanoate (pineapple, fruity), valencene (orange, fresh fruity), methyl anthranilate (also known as methyl 2-aminobenzoate) (grape), methyl butyrate (fruity, apple, pineapple), benzyl acetate (fruity, strawberry), p-mentha-8-thiol-3-one (grapefruit), (1S,4S)-trans-p-menthan-8-thiol-3-one acetate (black currant, exotic), (1R,4S)-cis-p-menthan-8-thiol-3-one acetate (fruity, sweet).

Without implying any limitation, a composition that comprises a formulation of terpenes and one or more modifiers, can consist of about 99.5% terpenes and about 0.5% modifiers, about 99% terpenes and about 1% modifiers, about 95% terpenes and about 5% modifiers, about 90% terpenes and about 10% modifiers, about 85% terpenes and about 15% modifiers, about 80% terpenes and about 20% modifiers, about 75% terpenes and about 25% modifiers, about 70% terpenes and about 30% modifiers, about 60% terpenes and about 40% modifiers, about 50% terpenes and about 50% modifiers, about 40% terpenes and about 60% modifiers, about 30% terpenes and about 70% modifiers, about 20% terpenes and about 80% modifiers, and so on, as expressed in weight/volume (wt./vol.).

In some embodiments, the compositions may additionally comprise surfactants, such as TWEENs, stearates, ammonium lauryl sulfate, sodium lauryl sulfate, or siloxanes. The surfactants may be anioic, cationic, nonionic, or zwitterionic. In some embodiments, the compositions may comprise thickening agents such as hydroxymethyl cellulose, hydroxyethyl cellulose, hydroxypropyl cellulose, or carboxymethyl cellulose. In some embodiments, the compositions include penetrants such as vitamin E or other tocopherols. In some embodiments the compositions include humectants.

Isolation and Analysis of Terpenes

Terpenes can be purified, analyzed, and identified, by various techniques, including high pressure liquid chromatography (HPLC), gas chromatography, and other chromatographic techniques (see, e.g., Musenga et al (2006) J. Sep. Sci. 29:1251-1258; Yang et al. (2009) J. Nat. Prod. 72:484-487; Jella et al. (1998) J. Agric. Food Chem. 46:242-247; Andrea et al. (2003) J. Agric. Food Chem. 51:4978-4983; Villa et al. (2007) J. Pharm. Biomed. Anal. 44:755-762).

Terpenes and other chemicals can be analyzed by mass spectrometry (Hendriks and Bruins (1983) Biol. Mass Spectrom. 10:377-381; gas chromatography-mass spectrometry (GC-MS) (Gadulo et al (2010) J. Food Sci. 75:C199-207), nuclear magnetic resonance (NMR) (Mucci et al (2013) Food Chem. 141:3167-3176; Zhang et al (2013) Food Chem. 138:208-213), mass spectroscopy, and Matrix-Assisted Laser Desorption/Ionization Time-of-Flight mass spectrometry (MALDI-TOF) (Scalarone et al. (2005) J. Mass Spectrom. 40:1527-1535).

Once the sample has been measured, e.g., with an analytical technique discussed above, the terpenes can be identified and quantified. The identification and quantification of the terpenes may involve comparison of the individual terpene mass, retention time, spectra, etc., to a database of terpene properties, e.g., as discussed below. Identification of the type and amount of terpenes may also involve comparison known distributions of terpenes, i.e., a "terpene fingerprint," to measured terpene distributions.

Creation of a Database of Terpenes

The present invention involves the isolation and analysis of naturally-occurring terpene compositions, and also the preparation of terpene compositions that mimic those compositions found in nature.

Methods of the inventions involve generating a library of prepared terpene compositions, the process comprising: obtaining a sample; analyzing a chemical profile of the sample to identify terpenes in the sample; quantifying the terpenes identified; and generating a library or database of terpene compositions based on those quantities. The method may further comprise preparing a blend of terpenes that mimics one or more of the compositions represented in the library.

The sample can be from any plant or other natural product, including *Cannabis sativa* L., *Humulus lupulus*, or other plant strains. The analysis step may comprise separating substances from a mixture, genetic analysis, chemotaxonomic analysis, compound extraction, gas chromatography flame ionization detection, chemical formula identification, chromatography, or any other analytical chemistry technique described herein or otherwise known in the art. Terpenes can be identified based on their chromatography profiles or other chemical properties of the analyzed compounds. Terpenes identified can be those listed in Table 1, or any other terpene. Terpenes may be quantified based on their mass fraction, percent weight, mole fraction, percentage by volume, or the like. The compositions and their quantities can be assembled as a library or database, or any other data management format known in the art. In embodiments that involve creating a prepared blend that mimics a naturally-occurring composition, the synthetic blend may comprise naturally-occurring terpenes, all synthetic terpenes, or a combination thereof.

Also provided is a database or library of terpene compositions produced by the above process.

Fluids

In "comprising" embodiments, the present disclosure provides a formulation that comprises a fluid that is a transparent liquid, a translucent liquid, an opaque liquid, a slurry, an emulsion, a suspension, a gel, and the like. In "consisting" embodiments, the present disclosure provides a formulation that consists of a fluid that is a transparent liquid, a translucent liquid, an opaque liquid, a slurry, an emulsion, a suspension, a gel, and the like. The designation of liquid, slurry, emulsion, gel, and so on, refers to this characterization as determined at room temperature (about 23 degrees centigrade).

Various additional components can be added, in addition to triacetin, to achieve the desired properties, such as dipropylene glycol, phytol, isophytol, diethyl phthalate, isoparaffins, paraffins, silicon oils, perfluorinated aliphatic ethers, polyethylene glycols, glycol ethers, glycol ether esters, esters, ketones, propylene glycol, ethanol, dimethicone or cyclomethicone, and so on.

Solvents such as propylene glycol are commonly used in electronic cigarette (e-cigarette) formulations. As discussed above, the addition of 10-70% cannabinoids to a mixture of terpenes and propylene glycol creates an emulsified mixture ideal for use in e-cigarettes.

Exclusionary Embodiments

In embodiments, the present disclosure can exclude a composition that has any essential oil. Also, the disclosure can exclude a composition that contains one or more specific oils, such as ocimum oil, jasmine oil, cymbopogon oil (lemongrass), santalum oil, eucalyptus oil, bergamote oil, lemon oil, lavandin oil, spearmint oil, wintergreen oil, cardamom oil, neroli bigarade oil, rosemary oil, orange oil, petitgrain oil, cinnamon leaf oil, vetiver oil, patchouli oil, grapefruit oil, mandarin oil, pepper oil, valerian oil, almond oil, citronella oil, anise oil, geranium oil, mint oil, verbena oil, clove oil, cajeput oil, fennel oil, girfole oil, myrtle oil, thyme oil, cypress oil, pine oil, armoise oil, and so on. What can be excluded is a composition that contains any kind of citrus fruit oil, e.g., from orange, lemon, grapefruit, and so on. Where applicable, the present disclosure encompasses an oil that is an "essential oil." Also, the present disclosure can encompass any formulation that includes one or more of the above oils.

In an exclusionary embodiment, the invention provides any of the above compositions, wherein the composition does not contain 3,3'-dihydroxy-5,4'-dimethoxybibenzyl. In another exclusionary embodiment, the invention provides any of the above compositions, wherein the composition does not contain cellulose. In another exclusionary embodiment, the invention provides any of the above compositions, wherein the composition does not contain chlorophyll.

Also, what can be excluded is any composition that contains a terpene that accounts for at least 20%, at least 30%, at least 40%, at least 50%, at least 60%, at least 70%, at least 80%, or at least 90%, of the terpenes in any one of the oils (or essential oils) disclosed herein. Moreover, what can be excluded is any composition that comprises one of the terpene trios that are identified in the tables herein. Each terpene trio is a group of three different terpenes that are explicitly identified by the three numbers in the trio (Table 1 is a key for each number).

Without implying any limitation, that can also be excluded from the present disclosure is any composition that includes one or more excipients, viscosity-imparting agents, solvents, binders, lubricants, preservatives, anti-oxidants, and the like. For example, what can be excluded from the present disclosure is, paraffin oil, isopropyl palmitate, cetryl alcohol, beeswax, polyethylene glycol, glycerol, pheoxyethanol, silica, sodium bicarbonate, sodium carbonate, cellulose, carboxymethyl cellulose, acacia, agar, gums, hydrogels, alginic acid, a monosaccharide, a disaccharide, and so on. In embodiments, the present disclosure can include one or more excipients, viscosity-imparting agents, solvents, binders, lubricants, preservatives, and the like, such as one or more of those disclosed herein.

In other exclusionary embodiments, what can be excluded is a composition, where a fluid component of the composition, does not contain one or more of the following molecules (see, e.g., Flores-Sanchez and Verpoorte (2008) Secondary metabolism in cannabis in Phytochem. Rev. DOI 10.1007/s11101-008-9094-4); cannabigerol; cannabichromene; cannabitriol; cannabidiol; cannabicyclolol; cannabielsoin, cannabinodiol; cannabinol; delta8-tetrahydrocannabinol; delta9-tetrahydrocannabinol; cannabichromanone; cannabicoumaronone; cannabicitran; 10-oxo-delta6a10a-tetrahydrocannabinol; cannabiglendol; delta7-isotetrahydrocannabinol; CBLVA; CBV; CBEVA-B; CBCVA; delta9-THCVA; CBDVA; CBGVA; divarinolic acid; quercetin; kaemferol; dihydrokaempferol; dihydroquercetin; cannflavin B; isovitexin; apigenin; naringenin; eriodictyol; luteolin; orientin; cytisoside; vitexin; canniprene; 3,4'-dihydroxy-5-methoxy bibenzyl; dihydroresveratrol; 3,4'dihydroxy-5,3'-dimethoxy-5'-isoprenyl; cannabistilbene 1; cannabistilbene 11a; cannabistilbene 11b; cannithrene 1; cannithrene 2; cannabispirone; iso-cannabispirone; cannabispirenon-A; cannabispirenone-B; canna-bispiradienone; alpha-cannabispiranol; beta-cannabispiranol; acetyl-cannabispirol; 7-hydroxy-5-methoxyindan-1-spiro-cyclohexane; 5-hydroxy-7-methoxyindan-1-spiro cyclohexane; 5,7-dihydroxyindan-1-cyclohexane; cannabispiradienone; 3,4'-dihydroxy-5-methoxybibenzyl; canniprene; cannabispirone; cannithrene I; cannithrene 2; alpha-cannabispiranol, acetyl-cannabispirol; vomifoliol; dihydrovomifoliol; dihydroactinidiolide; palustrine; palustridine; plus-cannabisativine; anhydrocannabisativine; dihydroperiphylline; cannabisin-A; cannabisin-B; cannabisin-C; cannabisin-D; grossamide; cannabisin-E; cannabisin-F; cannabisin-G; and so on.

The present disclosure provides a terpene formulation that comprises only one monoterpene. The present disclosure provides a terpene formulation that comprises only two monoterpenes. The present disclosure provides a terpene formulation that comprises only three monoterpenes. The present disclosure provides a terpene formulation that comprises only four monoterpenes.

The present disclosure provides a terpene formulation that comprises only one sesquiterpene. The present disclosure provides a terpene formulation that comprises only two sesquiterpenes. The present disclosure provides a terpene formulation that comprises only three sesquiterpenes. The present disclosure provides a terpene formulation that comprises only for sesquiterpenes.

In exclusionary embodiments, the present disclosure can exclude any composition, and can exclude any formulation that includes an essential oil. Also, the present disclosure can exclude any composition, and can exclude any formulation that includes one or more of salicylaldehyde, glycerol, polyethylene glycol, ionic detergent, non-ionic detergent, surfactant, phenylgycidate compound, calone, vanillin, jamonate, manzanate, verdox, vertoliff, furaneol, methyl cinnamate, butyl valerate, amyl acetate, furfural, ethyl vanillin, a lactone compound, any kind of aldehyde, methyl ionone, citrate, fumarate, amyl cinnamaldehyde, benzyl alcohol, free ions or salts of carbonate, free ions or salts of sulfate, free ions or salts of phosphate, cymene, any salicylate compound, anisyl alcohol, methyl heptin carbonate, any compound with a ketone group, any compound with a benzoate group, any sugar, dextrose, dextrate, silica, maltodextrin, sorbitol, and oil that is other than an essential oil, and the like. Other compounds, which can be excluded from the compositions and formulations of the present disclosure, or in the alternative, which can be included, are disclosed (see, e.g., US 2008/0194455 of Widder, U.S. Pat. No. 5,948,812 of Kraft, US 2003/0024997 of Welch, US 2009/0004303 of Perring each of which is incorporated herein by reference in its entirety).

The present disclosure provides a terpene formulation that comprises only one monoterpene. The present disclosure provides a terpene formulation that comprises only two monoterpenes. The present disclosure provides a terpene formulation that comprises only three monoterpenes. The present disclosure provides a terpene formulation that comprises only four monoterpenes.

The present disclosure provides a terpene formulation that comprises only one sesquiterpene. The present disclosure provides a terpene formulation that comprises only two sesquiterpenes. The present disclosure provides a terpene formulation that comprises only three sesquiterpenes. The present disclosure provides a terpene formulation that comprises only four sesquiterpenes.

In exclusionary embodiments, the present disclosure can exclude any composition, and can exclude any formulation that includes an essential oil. Also, the present disclosure can exclude any composition, and can exclude any formulation, that includes water, over 0.1% water (wt./vol.), over 0.2% water, over 0.5% water, over 1.0% water, over 2% water, over 5% water, and so on. Moreover, the present disclosure can exclude any composition, and can exclude any formulation, that includes one or more of salicylaldehyde, glycerol, polyethylene glycol, ionic detergent, hon-ionic detergent, surfactant, phenylgycidate compound, calone, vanillin, jamunate, manzanate, verdox, vertoliff, furaneol, methyl cinnamate, butyl valerate, amyl acetate, furfural, ethyl vanillin, a lactone compound, any kind of aldehyde, methyl ionone, citrate, fumarate, amyl cinnamaldehyde, benzyl alcohol, free ions or salts of carbonate, free ions or salts of sulfate, free ions or salts of phosphate, cymene, any salicylate compound, anisyl alcohol, methyl heptin carbonate, any compound with a ketone group, any compound with a benzoate group, any sugar, dextrose, dextrate, silica, maltodextrin, sorbitol, and oil that is other than an essential oil, and the like. Other compounds, which can be excluded from the compositions and formulations of the present disclosure, or in the alternative, which can be included, are disclosed (see, e.g., US 2008/0194455 of Widder, U.S. Pat. No. 5,948,812 of Kraft, US 2003/0024997 of Welch, US 2009/0004303 of Perring, US 2009/0162308 of Kuhn, each of which is incorporated herein by reference in its entirety).

The present disclosure provides formulations that include one or more of these terpenes. In exclusionary embodiments, the present disclosure can also exclude one or more of any terpene that is disclosed herein.

In some embodiments, without implying any limitation, a composition is a solution, suspension, emulsion, slurry, gel, and so on, where the formulation is mixed within or dispersed within the composition. In this type of embodiment, the formulation can be evenly distributed throughout the composition. In other embodiments, the composition and formulation can be substantially different things, for example, the composition can be a matrix of fibers, where the formulation surrounds or coats the fibers. Also, the composition can be a compartment that contains a fragrance that is not a terpene, while the formulation consists only of terpenes and that resides in a separate compartment. In some embodiments, the composition includes non-terpenes that float above the terpene formulation or, alternatively, that sink below the terpene formulation. In other embodiments, the non-terpene constituents of the composition can reside in beads or granules, while the terpene formulation can take the form of a solution. Alternatively, the terpene formulation can reside in beads or granules, while the non-terpene components of the terpene formulation can be configured as something that is not beads or granules.

EXAMPLE 1

In a first example, a composition was provided comprising equal parts MYR, LIM, LIN, API, and BCP. This particular composition of terpenes was designed to have a citrus scent. Three human subjects tested the organoleptic properties of the composition and reported the odor qualities of the composition. The first human subject reported a "sweet citrus" scent, with "woody earthen overtones." The second human subject described the composition as having a "light floral" aroma with a hint of "fruity citrus." The third human subject reported a "pleasant flowery scent" with notes of "lemony citrus."

EXAMPLE 2

To create a database of terpene compositions like the database or library described herein, naturally occurring plant samples were analyzed for their chemical properties.

FIG. 1 shows a method 100 for generating such a database. The method 100 involves obtaining a sample in step 110. The sample can be a naturally occurring plant product, such as a member of the Cannabis genus, or any other plant product. Step 120 of the method involves analyzing a chemical profile of the sample to identify terpenes therein. The analysis can be any of the chemical analyses described herein, including chromatography. The analysis step may further comprise other processes for extracting compounds or otherwise preparing the sample for analysis. The method further comprises quantifying terpenes in step 130. The terpenes can be quantified by mass fraction, percent weight, mole fraction, percentage by volume, or the like. The quantities can be used to determine a ratio of terpenes in the composition. In step 140, those quantities, ratios, or other chemical properties are entered into a database of terpene compositions. The database may comprise chromatography profiles or other chemical properties found in the terpene compositions.

Figure 2:
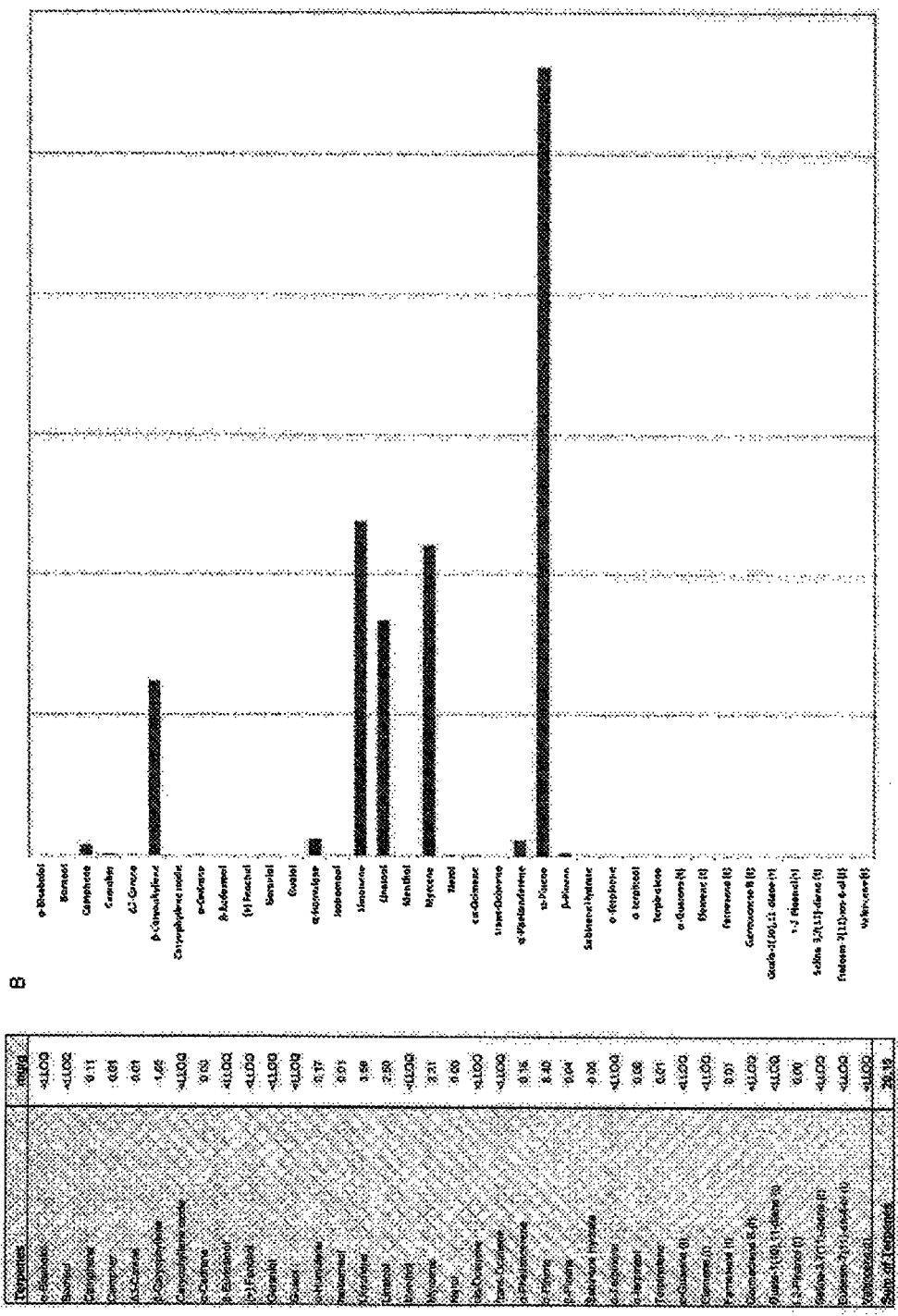
FIG. 2 shows the result of a chromatographic analysis of a typical blend or strain of plant by terpene content, according to the present inventions.

An example of one such analysis is shown in FIG. 2. A sample of a naturally occurring plant was isolated and analyzed using chromatography. The five most abundant terpenes in the composition were found to be BCP, LIM, LIN, MYR, and API. These terpenes were determined to be present in quantities of 1.85 mg/g, 3.56 mg/g, 2.50 mg/g, 3.31 mg/g, and 8.40 mg/g, respectively. Other terpenes were found in trace quantities, including camphene, humulene, phellandrene, and BPI. These quantities and chemical properties were entered into a database, like the one described herein.

EXAMPLE 3

A variety of compositions suitable for use with electronic cigarettes are prepared. They are disclosed in Formulations 1-7, disclosed below.

| Formulation 1 | |
|---|---|
| Ingredient | Weight percent of ingredient (wt/wt formulation) |
| Dipropylene glycol | 65% |
| THC | 25% |
| LIM | 4% |
| BCP | 3% |
| MYR | 3% |

| Formulation 2 | |
|---|---|
| Ingredient | Weight percent of ingredient (wt/wt formulation) |
| Dipropylene glycol | 90% |
| BCP | 5% |
| LIM | 2.5% |
| MYR | 2.5% |

| Formulation 3 | |
|---|---|
| Ingredient | Weight percent of ingredient (wt/wt formulation) |
| Dipropylene glycol | 74% |
| Phytol | 10% |

Formulation 3

| Ingredient | Weight percent of ingredient (wt/wt formulation) |
|---|---|
| THC | 14% |
| BCP | 1% |
| LIM | 0.5% |
| MYR | 0.5% |

Formulation 4

| Ingredient | Weight percent of ingredient (wt/wt formulation) |
|---|---|
| Dipropylene glycol | 74% |
| Triacetin | 9% |
| THC | 14% |
| NDL | 1% |
| FOL | 0.6% |
| LIM | 0.6% |
| EUC | 0.3% |
| LIN | 0.3% |
| GER | 0.2% |

Formulation 5

| Ingredient | Weight percent of ingredient (wt/wt formulation) |
|---|---|
| Phytol | 89% |
| NDL | 3% |
| FOL | 2% |
| LIM | 2% |
| EUC | 2% |
| LIN | 1% |
| GER | 1% |

Formulation 6

| Ingredient | Weight percent of ingredient (wt/wt formulation |
|---|---|
| Phytol | 80% |
| THC | 17% |
| NDL | 1% |
| FOL | 0.6% |
| LIM | 0.6% |
| EUC | 0.3% |
| LIN | 0.3% |
| GER | 0.2% |

Formulation 7

| Ingredient | Weight percent of ingredient (wt/wt formulation) |
|---|---|
| THC | 80% |
| Phytol | 17% |
| NDL | 1% |
| FOL | 0.6% |
| LIM | 0.6% |
| EUC | 0.3% |
| LIN | 0.3% |
| GER | 0.2% |

EXAMPLE 4

A variety of compositions suitable for use as a personal lubricant are prepared. They are disclosed in Formulations 8-16, discussed below.

Formulation 8 (gel)

| Ingredient | Weight percent of ingredient (wt/wt formulation) |
|---|---|
| Water | 75% |
| Propylene glycol | 10% |
| Hydroxyethyl cellulose | 3% |
| Triacetin | 8% |
| THC | 4% |

Formulation 9 (gel)

| Ingredient | Weight percent of ingredient (wt/wt formulation) |
|---|---|
| Water | 75% |
| Propylene glycol | 10% |
| Hydroxyethyl cellulose | 4% |
| Triacetin | 9% |
| BCP | 1% |
| LIM | 0.5% |
| MYR | 0.5% |

Formulation 10 (gel)

| Ingredient | Weight percent of ingredient (wt/wt formulation) |
|---|---|
| Water | 74% |
| Propylene glycol | 9% |
| Hydroxypropyl cellulose | 3% |
| Triacetin | 8% |
| THC | 4% |
| BCP | 1% |
| LIM | 0.5% |
| MYR | 0.5% |

Formulation 11 (gel)

| Ingredient | Weight percent of ingredient (wt/wt formulation) |
|---|---|
| Water | 71.5% |
| Propylene glycol | 6% |
| Polyethylene glycol | 6% |
| Hydroxyethyl cellulose | 4% |
| Triacetin | 10% |
| NDL | 0.5% |
| Isopropyl myristate | 0.5% |
| FOL | 0.4% |
| LIM | 0.4% |
| EUC | 0.3% |
| LIN | 0.2% |
| GER | 0.2% |

Formulation 12 (gel)

| Ingredient | Weight percent of ingredient (wt/wt formulation) |
|---|---|
| Water | 72.5% |
| Propylene glycol | 6% |
| Polyethylene glycol | 4% |
| Hydroxyethyl cellulose | 3% |
| Triacetin | 8% |
| THC | 4% |
| NDL | 0.5% |
| Isopropyl myristate | 0.5% |
| FOL | 0.4% |
| LIM | 0.4% |
| EUC | 0.3% |
| LIN | 0.2% |
| GER | 0.2% |

Formulation 13 (gel)

| Ingredient | Weight percent of ingredient (wt/wt formulation) |
|---|---|
| Water | 73% |
| Propylene glycol | 8% |
| Hydroxyethyl cellulose | 3% |
| Triacetin | 7.5% |
| THC | 4% |
| Lactic acid | 2% |
| NDL | 0.5% |
| Isopropyl myristate | 0.5% |
| FOL | 0.4% |
| LIM | 0.4% |
| EUC | 0.3% |
| LIN | 0.2% |
| GER | 0.2% |

Formulation 14 (gel)

| Ingredient | Weight percent of ingredient (wt/wt formulation) |
|---|---|
| Water | 74% |
| Propylene glycol | 9% |
| Hydroxyethyl cellulose | 3% |
| Triacetin | 7.5% |
| THC | 4% |
| NDL | 0.5% |
| Isopropyl myristate | 0.5% |
| FOL | 0.4% |
| LIM | 0.4% |
| EUC | 0.3% |
| LIN | 0.2% |
| GER | 0.2% |

Formulation 15 (gel)

| Ingredient | Weight percent of ingredient (wt/wt formulation) |
|---|---|
| Water | 60% |
| Propylene glycol | 12% |
| Hydroxyethyl cellulose | 3% |
| Triacetin | 15% |
| THC | 10% |

Formulation 16 (gel)

| Ingredient | Weight percent of ingredient (wt/wt formulation) |
|---|---|
| Water | 65% |
| Propylene glycol | 14% |
| Hydroxyethyl cellulose | 4% |
| Triacetin | 15% |
| BCP | 1% |
| LIM | 0.5% |
| MYR | 0.5% |

Formulation 17 (gel)

| Ingredient | Weight percent of ingredient (wt/wt formulation) |
|---|---|
| Water | 60% |
| Propylene glycol | 12% |
| Hydroxypropyl cellulose | 4% |
| Triacetin | 13% |
| THC | 9% |
| BCP | 1% |
| LIM | 0.5% |
| MYR | 0.5% |

Formulation 18 (gel)

| Ingredient | Weight percent of ingredient (wt/wt formulation) |
|---|---|
| Water | 58.5% |
| Propylene glycol | 12% |
| Polyethylene glycol | 12% |
| Hydroxyethyl cellulose | 5% |
| Triacetin | 10% |
| NDL | 0.5% |
| Isopropyl myristate | 0.5% |
| FOL | 0.4% |
| LIM | 0.4% |
| EUC | 0.3% |
| LIN | 0.2% |
| GER | 0.2% |

Formulation 19 (gel)

| Ingredient | Weight percent of ingredient (wt/wt formulation) |
|---|---|
| Water | 61.5% |
| Propylene glycol | 8% |
| Polyethylene glycol | 5% |
| Hydroxyethyl cellulose | 3% |
| Triacetin | 12% |
| THC | 8% |
| NDL | 0.5% |
| Isopropyl myristate | 0.5% |
| FOL | 0.4% |
| LIM | 0.4% |
| EUC | 0.3% |
| LIN | 0.2% |
| GER | 0.2% |

| Formulation 20 (gel) | |
|---|---|
| Ingredient | Weight percent of ingredient (wt/wt formulation) |
| Water | 60% |
| Propylene glycol | 12% |
| Hydroxyethyl cellulose | 5% |
| Triacetin | 10.5% |
| THC | 8% |
| Lactic acid | 2% |
| NDL | 0.5% |
| Isopropyl myristate | 0.5% |
| FOL | 0.4% |
| LIM | 0.4% |
| EUC | 0.3% |
| LIN | 0.2% |
| GER | 0.2% |

| Formulation 21 (gel) | |
|---|---|
| Ingredient | Weight percent of ingredient (wt/wt formulation) |
| Water | 60% |
| Propylene glycol | 10% |
| Hydroxyethyl cellulose | 5% |
| Triacetin | 10.5% |
| THC | 13% |
| NDL | 0.5% |
| Isopropyl myristate | 0.5% |
| FOL | 0.4% |
| LIM | 0.4% |
| EUC | 0.3% |
| LIN | 0.2% |
| GER | 0.2% |

| Formulation 22 (liquid) | |
|---|---|
| Ingredient | Weight percent of ingredient (wt/wt formulation) |
| Water | 55% |
| Propylene glycol | 5% |
| Hydroxyethyl cellulose | 1% |
| Triacetin | 8% |
| Sorbitol | 10% |
| Glycerin | 14% |
| THC | 4% |
| NDL | 0.5% |
| Isopropyl myristate | 0.5% |
| FOL | 0.5% |
| LIM | 0.5% |
| EUC | 0.4% |
| LIN | 0.3% |
| GER | 0.3% |

| Formulation 23 (liquid) | |
|---|---|
| Ingredient | Weight percent of ingredient (wt/wt formulation) |
| Water | 55% |
| Propylene glycol | 5% |
| Hydroxyethyl cellulose | 1% |
| Triacetin | 4% |
| Sorbitol | 10% |
| Glycerin | 10% |
| THC | 4% |
| NDL | 0.5% |
| Isopropyl myristate | 0.5% |

-continued

| Formulation 23 (liquid) | |
|---|---|
| Ingredient | Weight percent of ingredient (wt/wt formulation) |
| FOL | 0.5% |
| LIM | 0.5% |
| EUC | 0.4% |
| LIN | 0.3% |
| GER | 0.3% |

OTHER EXAMPLES

Compositions of the present disclosure encompass, but are not limited to, combinations of terpenes from Tables 1-37.

TABLE 1

Terpenes
Table 1. Terpenes

| | |
|---|---|
| 1 | alpha-bisabolol |
| 2 | borneol |
| 3 | camphene |
| 4 | camphor |
| 5 | delta-3-carene |
| 6 | beta-caryophyllene |
| 7 | caryophyllene oxide |
| 8 | alpha-cedrene |
| 9 | beta-eudesmol |
| 10 | fenchyl alcohol |
| 11 | geraniol |
| 12 | guaiol |
| 13 | alpha-humulene |
| 14 | isoborneol |
| 15 | limonene |
| 16 | linalool |
| 17 | menthol |
| 18 | myrcene |
| 19 | nerol |
| 20 | ocimene |
| 21 | trans-ocimene |
| 22 | alpha-phellandrene |
| 23 | alpha-pinene |
| 24 | beta-pinene |
| 25 | sabinene |
| 26 | alpha-terpinene |
| 27 | alpha-terpineol |
| 28 | terpinolene |
| 29 | alpha-guaiene |
| 30 | elemene |
| 31 | farnesene |
| 32 | germacrene B |
| 33 | guaia-1(10),11-diene |
| 34 | trans-2-pinanol |
| 35 | selina-3,7(11)-diene |
| 36 | eudesm-7(11)-en-4-ol |
| 37 | valencene |

TABLE 2

Alpha-bisabolol family of terpene formulations.
The numbers refer to the terpenes from Table 1. The designation "family" is only for convenience in presentation, as other tables also include formulations with alpha-bisabolol.

| Subfamily | |
|---|---|
| 2 | 1 + 2 + 3, 1 + 2 + 4, 1 + 2 + 5, 1 + 2 + 6, 1 + 2 + 7, 1 + 2 + 8, 1+ 2 + 9, 1 + 2 + 10, 1 + 2 + 11, 1 + 2 + 12, 1 + 2 + 13, 1 + 2 + 14, 1 +2 + 15, 1 + 2 + 16, 1 + 2 + 17, 1 + 2 + 18, 1 + 2 + |

TABLE 2-continued

Alpha-bisabolol family of terpene formulations.
The numbers refer to the terpenes from Table 1. The designation "family" is only for convenience in presentation, as other tables also include formulations with alpha-bisabolol.

| Subfamily | |
|---|---|
|  | 19, 1 + 2 + 20, 1 + 2 + 21, 1 + 2 +22, 1 + 2 + 23, 1 + 2 + 24, 1 + 2 + 25, 1 + 2 + 26, 1 + 2 + 27, 1 + 2 + 28, 1 + 2 + 29, 1 + 2 + 30, 1 + 2 + 31, 1 + 2 + 32, 1 + 2 + 33, 1 + 2 + 34, 1 + 2 + 35, 1 + 2 + 36, 1 + 2 + 37. |
| 3 | 1 + 3 + 4, 1 + 3 + 5, 1 + 3 + 6, 1 + 3 + 7, 1 + 3 + 8, 1 + 3 + 9, 1 + 3 + 10, 1 + 3 + 11, 1 + 3 + 12, 1 + 3 + 13, 1 + 3 + 14, 1 + 3 + 15, 1 + 3 + 16, 1 + 3 + 17, 1 + 3 + 18, 1 + 3 + 19, 20, 1 + 3 + 21, 1 + 3 + 22, 1 + 3 + 23, 1 + 3 + 24, 1 + 3 + 25, 1 + 3 + 26, 1 + 3 + 27, 1 + 3 + 28, 1 + 3 + 29, 1 + 3 + 30, 1 + 3 + 31, 1 + 3 + 32, 1 + 3 + 33, 1 + 3 + 34, 1 + 3 + 35, 1 + 3 + 36, 1 + 3 + 37. |
| 4 | 1 + 4 + 5, 1 + 4 + 6, 1 + 4 + 7, 1 + 4 + 8, 1 + 4 + 9, 1 + 4 + 10, 1 + 4 + 11, 1 + 4 + 12, 1 + 4 + 13, 1 + 4 + 14, 1 + 4 + 15, 1 + 4 + 16, 1 + 4 + 17, 1 + 4 + 18, 1 + 4 + 19, 1 + 4 + 20, 1 + 4 + 21, 1 + 4 + 22, 1 + 4 + 23, 1 + 4 + 24, 1 + 4 + 25, 1 + 4 + 26, 1 + 4 + 27, 1 + 4 + 28, 1 + 4 + 29, 1 + 4 + 30, 1 + 4 + 31, 1 + 4 + 32, 1 + 4 + 33, 1 + 4 + 34, 1 + 4 + 35, 1 + 4 + 36, 1 + 4 + 37. |
| 5 | 1 + 5 + 6, 1 + 5 + 7, 1 + 5 + 8, 1 + 5 + 9, 1 + 5 + 10, 1 + 5 + 11, 1 + 5 + 12, 1 + 5 + 13, 1 + 5 + 14, 1 + 5 + 15, 1 + 5 + 16, 1 + 5 + 17, 1 + 5 + 18, 1 + 5 + 19, 1 + 5 + 20, 1 + 5 + 21, 1 + 5 + 22, 1 + 5 + 23, 1 + 5 + 24, 1 + 5 + 25, 1 + 5 + 26, 1 + 5 + 27, 1 + 5 + 28, 1 + 5 + 29, 1 + 5 + 30, 1 + 5 + 31, 1 + 5 + 32, 1 + 5 + 33, 1 + 5 + 34, 1 + 5 + 35, 1 + 5 + 36, 1 + 5 + 37. |
| 6 | 1 + 6 + 7, 1 + 6 + 8, 1 + 6 + 9, 1 + 6 + 10, 1 + 6 + 11, 1 + 6 + 12, 1 + 6 + 13, 1 + 6 + 14, 1 + 6 + 15, 1 + 6 + 16, 1 + 6 + 17, 1 + 6 + 18, 1 + 6 + 19, 1 + 6 + 20, 1 + 6 + 21, 1 + 6 + 22, 1 + 6 + 23, 1 + 6 + 24, 1 + 6 + 25, 1 + 6 + 26, 1 + 6 + 27, 1 + 6 + 28, 1 + 6 + 29, 1 + 6 + 30, 1 + 6 + 31, 1 + 6 + 32, 1 + 6 + 33, 1 + 6 + 34, 1 + 6 + 35, 1 + 6 + 36, 1 + 6 + 37. |
| 7 | 1 + 7 + 8, 1 + 7 + 9, 1 + 7 + 10, 1 + 7 + 11, 1 + 7 + 12, 1 + 7 + 13, 1 + 7 + 14, 1 + 7 + 15, 1 + 7 + 16, 1 + 7 + 17, 1 + 7 + 18, 1 + 7 + 19, 1 + 7 + 20, 1 + 7 + 21, 1 + 7 + 22, 1 + 7 + 23, 1 + 7 + 24, 1 + 7 + 25, 1 + 7 + 26, 1 + 7 + 27, 1 + 7 + 28, 1 + 7 + 29, 1 + 7 + 30, 1 + 7 + 31, 1 + 7 + 32, 1 + 7 + 33, 1 + 7 + 34, 1 + 7 + 35, 1 + 7 + 36, 1 + 7 + 37. |
| 8 | 1 + 8 + 9, 1 + 8 + 10, 1 + 8 + 11, 1 + 8 + 12, 1 + 8 + 13, 1 + 8 + 14, 1 + 8 + 15, 1 + 8 + 16, 1 + 8 + 17, 1 + 8 + 18, 1 + 8 + 19, 1 + 8 + 20, 1 + 8 + 21, 1 + 8 + 22, 1 + 8 + 23, 1 + 8 + 24, 1 + 8 + 25, 1 + 8 + 26, 1 + 8 + 27, 1 + 8 + 28, 1 + 8 + 29, 1 + 8 + 30, 1 + 8 + 31, 1 + 8 + 32, 1 + 8 + 33, 1 + 8 + 34, 1 + 8 + 35, 1 + 8 + 36, 1 + 8 + 37. |
| 9 | 1 + 9 + 10, 1 + 9 + 11, 1 + 9 + 12, 1 + 9 + 13, 1 + 9 + 14, 1 + 9 + 15, 1 + 9 + 16, 1 + 9 + 17, 1 + 9 + 18, 1 + 9 + 19, 1 + 9 + 20, 1 + 9 + 21, 1 + 9 + 22, 1 + 9 + 23, 1 + 9 + 24, 1 + 9 + 25, 1 + 9 + 26, 1 + 9 +27, 1 + 9 + 28, 1 + 9 + 29, 1 + 9 + 30, 1 + 9 + 31, 1 + 9 + 32, 1 + 9 + 33, 1 + 9 + 34, 1 + 9 + 35, 1 + 9 + 36, 1 + 9 + 37. |
| 10 | 1 + 10 + 11, 1 + 10 + 12, 1 + 10 + 13, 1 + 10 + 14, 1 + 10 + 15, 1 + 10 + 16, 1 + 10 + 17, 1 + 10 + 18, 1 + 10 + 19, 1 + 10 + 20, 1 + 10 + 21, 1 + 10 + 22, 1 + 10 + 23, 1 + 10 + 24, 1 + 10 + 25, 1 + 10 + 26, 1 + 10 + 27, 1 + 10 + 28, 1 + 10 + 29, 1 + 10 + 30, 1 + 10 + 31, 1 + 10 + 32, 1 + 10 + 33, 1 + 10 + 34, 1 + 10 + 35, 1 + 10 + 36, 1 + 10 + 37. |
| 11 | 1 + 11 + 12, 1 + 11 + 13, 1 + 11 + 14, 1 + 11 + 15, 1 + 11 + 16, 1 + 11 + 17, 1 + 11 + 18, 1 + 11 + 19, 1 + 11 + 20, 1 + 11 + 21, 1 + 11 + 22, 1 + 11 + 23, 1 + 11 + 24, 1 + 11 + 25, 1 + 11 + 26, 1 + 11 + 27, 1 + 11 + 28, 1 + 11 + 29, 1 + 11 + 30, 1 + 11 + 31, 1 + 11 + 32, 1 + 11 + 33, 1 + 11 + 34, 1 + 11 + 35, 1 + 11 + 36, 1 + 11 + 37. |
| 12 | 1 + 12 + 13, 1 + 12 + 14, 1 + 12 + 15, 1 + 12 + 16, 1 + 12 + 17, 1 + 12 + 18, 1 + 12 + 19, 1 + 12 + 20, 1 + 12 + 21, 1 + 12 + 22, 1 + 12 + 23, 1 + 12 + 24, 1 + 12 + 25, 1 + 12 + 26, 1 + 12 + 27, 28, 1 + 12 + 29, 1 + 12 + 30, 1 + 12 + 31, 1 + 12 + 32, 1 + 12 + 33, 1 + 12 + 34, 1 + 12 + 35, 1 + 12 + 36, 1 + 12 + 37. |
| 13 | 1 + 13 + 14, 1 + 13 + 15, 1 + 13 + 16, 1 + 13 + 17, 1 + 13 + 18, 1 + 13 + 19, 1 + 13 + 20, 1 + 13 + 21, 1 + 13 + 22, 1 + 13 + 23, 1 + 13 + 24, 1 + 13 + 25, 1 + 13 + 26, 1 + 13 + 27, 1 + 13 + 28, 1 + 13 + 29, 1 + 13 + 30, 1 + 13 + 31, 1 + 13 + 32, 1 + 13 + 33, 1 + 13 + 34, 1 + 13 + 35, 1 + 13 + 36, 1 + 13 + 37. |
| 14 | 1 + 14 + 15, 1 + 14 + 16, 1 + 14 + 17, 1 + 14 + 18, 1 + 14 + 19, 1 + 14 + 20, 1 + 14 + 21, 1 + 14 + 22, 1 + 14 + 23, 1 + 14 + 24, 1 + 14 + 25, 1 + 14 + 26, 1 + 14 + 27, 1 + 14 + 28, 1 + 14 + 29, 1 + 14 + 30, 1 + 14 + 31, 1 + 14 + 32, 1 + 14 + 33, 1 + 14 + 34, 1 + 14 + 35, 1 + 14 + 36, 1 + 14 + 37. |
| 15 | 1 + 15 + 16, 1 + 15 + 17, 1 + 15 + 18, 1 + 15 + 19, 1 + 15 + 20, 1 + 15 + 21, 1 + 15 + 22, 1 + 15 + 23, 1 + 13 + 24, 1 + 15 + 25, 1 + 15 + 26, 1 + 15 + 27, 1 + 15 + 28, 1 + 15 + 29, 1 + 15 + 30, 1 + 15 + 31, 1 + 15 + 32, 1 + 15 + 33, 1 + 15 + 34, 1 + 15 + 35. |
| 16 | 1 + 16 + 17, 1 + 16 + 18, 1 + 16 + 19, 1 + 16 + 20, 1 + 16 + 21, 1 + 16 + 22, 1 + 16 + 23, 1 + 16 + 24, 1 + 16 + 25, 1 + 16 + 26, 1 + 16 + 27, 1 + 16 + 28, 1 + 16 + 29, 1 + 16 + 30, 1 + 16 + 31, 1 + 16 + 32, 1 + 16 + 33, 1 + 16 + 34, 1 + 16 + 35, 1 + 16 + 36, 1 + 16 + 37. |
| 17 | 1 + 17 + 18, 1 + 17 + 19, 1 + 17 + 20, 1 + 17 + 21, 1 + 17 + 22, 1 + 17 + 23, 1 + 17 + 24, 1 + 17 + 25, 1 + 17 + 26, 1 + 17 + 27, 1 + 17 + 28, 1 + 17 + 29, 1 + 17 + 30, 1 + 17 + 31, 1 + 17 + 32, 1 + 17 + 33, 1 + 17 + 34, 1 + 17 + 35, 1 + 17 + 36, 1 + 17 + 37. |
| 18 | 1 + 18 + 19, 1 + 18 + 20, 1 + 18 + 21, 1 + 18 + 22, 1 + 18 + 23, 1 + 18 + 24, 1 + 18 + 25, 1 + 18 + 26, 1 + 18 + 27, 1 + 18 + 28, 1 + 18 + 29, 1 + 18 + 30, 1 + 18 + 31, 1 + 18 + 32, 1 + 18 + 33, 1 + 18 + 34, 1 + 18 + 35, 1 + 18 + 36, 1 + 18 + 37. |
| 19 | 1 + 19 + 20, 1 + 19 + 21, 1 + 19 + 22, 1 + 19 + 23, 1 + 19 + 24, 1 + 19 + 25, 1 + 19 + 26, 1 + 19 + 27, 1 + 19 + 28, 1 + 19 + 29, 1 + 19 + 30, 1 + 19 + 31, 1 + 19 + 32, 1 + 19 + 33, 1 + 19 + 34, 1 + 19 + 35, 1 + 19 + 36, 1 + 19 + 37. |
| 20 | 1 + 20 + 21, 1 + 20 + 22, 1 + 20 + 23, 1 + 20 + 24, 1 + 20 + 25, 1 + 20 + 26, 1 + 20 + 27, 1 + 20 + 28, 1 + 20 + 29, 1 + 20 + 30, 1 + 20 + 31, 1 + 20 + 32, 1 + 20 + 33, 1 + 20 + 34, 1 + 20 + 35, 1 + 20 + 36, 1 + 20 + 37. |
| 21 | 1 + 21 + 22, 1 + 21 + 23, 1 + 21 + 24, 1 + 21 + 25, 1 + 21 + 26, 1 + 21 + 27, 1 + 21 + 28, 1 + 21 + 29, 1 + 21 + 30, 1 + 21 + 31, 1 + 21 + 32, 1 + 21 + 33, 1 + 21 + 34, 1 + 21 + 35, 1 + 21 + 36, 1 + 21 + 37. |
| 22 | 1 + 22 + 23, 1 + 22 + 24, 1 + 22 + 25, 1 + 22 + 26, 1 + 22 + 27, 1 + 22 + 28, 1 + 22 + 29, 1 + 22 + 30, 1 + 22 + 31, 1 + 22 + 32, 1 + 22 + 33, 1 + 22 + 34, 1 + 22 + 35, 1 + 22 + 36, 1 + 22 + 37. |
| 23 | 1 + 23 + 24, 1 + 23 + 25, 1 + 23 + 26, 1 + 23 + 27, 1 + 23 + 28, 1 + 23 + 29, 1 + 23 + 30, 1 + 23 + 31, 1 + 23 + 32, 1 + 23 + 33, 1 + 23 + 34, 1 + 23 + 35, 1 + 23 + 36, 1 + 23 + 37. |
| 24 | 1 + 24 + 25, 1 + 24 + 26, 1 + 24 + 27, 1 + 24 + 28, 1 + 24 + 29, 1 + 24 + 30, 1 + 24 + 31, 1 + 24 + 32, 1 + 24 + 33, 1 + 24 + 34, 1 + 24 + 35, 1 + 24 + 36, 1 + 24 + 37. |

TABLE 2-continued

Alpha-bisabolol family of terpene formulations.
The numbers refer to the terpenes from Table 1. The designation "family" is only for convenience in presentation, as other tables also include formulations with alpha-bisabolol.

| Subfamily | |
|---|---|
| 25 | 1 + 25 + 26, 1 + 25 + 27, 1 + 25 + 28, 1 + 25 + 29, 1 + 25 + 30, 1 + 25 + 31, 1 + 25 + 32, 1 + 25 + 33, 1 + 25 + 34, 1 + 25 + 35, 1 + 25 + 36, 1 + 25 + 37. |
| 26 | 1 + 26 + 27, 1 + 26 + 28, 1 + 26 + 29, 1 + 26 + 30, 1 + 26 + 31, 1 + 26 + 32, 1 + 26 + 33, 1 + 26 + 34, 1 + 26 + 35, 1 + 26 + 36, 1 + 26 + 37. |
| 27 | 1 + 27 + 28, 1 + 27 + 29, 1 + 27 + 30, 1 + 27 + 31, 1 + 27 + 32, 1 + 27 + 33, 1 + 27 + 34, 1 + 27 + 35, 1 + 27 + 36, 1 + 27 + 37. |
| 28 | 1 + 28 + 29, 1 + 28 + 30, 1 + 28 + 31, 1 + 28 + 32, 1 + 28 + 33, 1 + 28 + 34, 1 + 28 + 35, 1 + 28 + 36, 1 + 28 + 37. |
| 29 | 1 + 29 + 30, 1 + 29 + 31, 1 + 29 + 32, 1 + 29 + 33, 1 + 29 + 34, 1 + 29 + 35, 1 + 29 + 36, 1 + 29 + 37. |
| 30 | 1 + 30 + 31, 1 + 31 + 32, 1 + 30 + 33, 1 + 30 + 34, 1 + 30 + 35, 1 + 30 + 36, 1 + 30 + 37. |
| 31 | 1 + 31 + 32, 1 + 31 + 33, 1 + 31 + 34, 1 + 31 + 35, 1 + 31 + 36, 1 + 31 + 37. |
| 32 | 1 + 32 + 33, 1 + 32 + 34, 1 + 32 + 35, 1 + 32 + 36, 1 + 32 + 37. |
| 33 | 1 + 33 + 34, 1 + 33 + 35, 1 + 33 + 36, 1 + 33 + 37. |
| 34 | 1 + 34 + 35, 1 + 34 + 36, 1 + 34 + 37. |
| 35 | 1 + 35 + 36, 1 + 35 + 37. |
| 36 | 1 + 36 + 27. |

TABLE 3

Borneol family of terpene formulations.
The numbers refer to the terpenes from Table 1.
The designation "family" is only for convenience in presentation, as other tables also include formulations with borneol.

Each disclosure of three terpenes represents a distinct formulation. In one embodiment, the formulation that is described by the indicated mixture of the three terpenes does not include any additional terpenes. In other embodiments, it does include additional terpenes.

| Subfamily | |
|---|---|
| 3 | 2 + 3 + 4, 2 + 3 + 5, 2 + 3 + 6, 2 + 3 + 7, 2 + 3 + 8, 2 + 3 + 9, 2 + 3 + 10, 2 + 3 + 11, 2 + 3 + 12, 2 + 3 + 13, 2 + 3 + 14, 2 + 3 + 15, 2 + 3 + 16, 2 + 3 + 17, 2 + 3 + 18, 2 + 3 + 19, 2 + 3 + 20, 2 + 3 + 21, 2 + 3 + 22, 2 + 3 + 23, 2 + 3 + 24, 2 + 3 + 25, 2 + 3 + 26, 2 + 3 + 27, 2 + 3 + 28, 2 + 3 + 29, 2 + 3 + 30, 2 + 3 + 31, 2 + 3 + 32, 2 + 3 + 33, 2 + 3 + 34, 2 + 3 + 35, 2 + 3 + 36, 2 + 3 + 37. |
| 4 | 2 + 4 + 5, 2 + 4 + 6, 2 + 4 + 7, 2 + 4 + 8, 2 + 4 + 9, 2 + 4 + 10, 2 + 4 + 11, 2 + 4 + 12, 2 + 4 + 13, 2 + 4 + 4, 2 + 4 + 15, 2 + 4 + 16, 2 + 4 + 17, 2 + 4 + 18, 2 + 4 + 19, 2 + 4 + 20, 2 + 4 + 21, 2 + 4 + 22, 2 + 4 + 23, 2 + 4 + 24, 2 + 4 + 25, 2 + 4 + 26, 2 + 4 + 27, 2 + 4 + 28, 2 + 4 + 29, 2 + 4 + 30, 2 + 4 + 31, 2 + 4 + 32, 2 + 4 + 33, 2 + 4 + 34, 2 + 4 + 35, 2 + 4 + 36, 2 + 4 + 37. |
| 5 | 2 + 5 + 6, 2 + 5 + 7, 2 + 5 + 8, 2 + 5 + 9, 2 + 5 + 10, 2 + 5 + 11, 2 + 5 + 12, 2 + 5 + 13, 2 + 5 + 14, 2 + 5 + 15, 2 + 5 + 16, 2 + 5 + 17, 2 + 5 + 18, 2 + 5 + 19, 2 + 5 + 20, 2 + 5 + 21, 2 + 5 + 22, 2 + 5 + 23, 2 + 5 + 24, 2 + 5 + 25, 2 + 5 + 26, 2 + 5 + 27, 2 + 5 + 28, 2 + 5 + 29, 2 + 5 + 30, 2 + 5 + 31, 2 + 5 + 32, 2 + 5 + 33, 2 + 5 + 34, 2 + 5 + 35, 2 + 5 + 36, 2 + 5 + 37. |

TABLE 3-continued

Borneol family of terpene formulations.
The numbers refer to the terpenes from Table 1.
The designation "family" is only for convenience in presentation, as other tables also include formulations with borneol.

Each disclosure of three terpenes represents a distinct formulation. In one embodiment, the formulation that is described by the indicated mixture of the three terpenes does not include any additional terpenes. In other embodiments, it does include additional terpenes.

| Subfamily | |
|---|---|
| 6 | 2 + 6 + 7, 2 + 6 + 8, 2 + 6 + 9, 2 + 6 + 10, 2 + 6 + 11, 2 + 6 + 12, 2 + 6 + 13, 2 + 6 + 14, 2 + 6 + 15, 2 + 6 + 16, 2 + 6 + 17, 2 + 6 + 18, 2 + 6 + 19, 2 + 6 + 20, 2 + 6 + 21, 2 + 6 + 22, 2 + 6 + 23, 2 + 6 + 24, 2 + 6 + 25, 2 + 6 + 26, 2 + 6 + 27, 2 + 6 + 28, 2 + 6 + 29, 2 + 6 + 30, 2 + 6 + 31, 2 + 6 + 32, 2 + 6 + 33, 2 + 6 + 34, 2 + 6 + 35, 2 + 6 + 36, 2 + 6 + 37. |
| 7 | 2 + 7 + 8, 2 + 7 + 9, 2 + 7 + 10, 2 + 7 + 11, 2 + 7 + 12, 2 + 7 + 13, 2 + 7 + 14, 2 + 7 + 15, 2 + 7 + 16, 2 + 7 +17, 2 + 7 + 18, 2 + 7 + 19, 2 + 7 + 20, 2 + 7 + 21, 2 + 7 + 22, 2 + 7 + 23, 2 + 7 + 24, 2 + 7 + 25, 2 + 7 + 26, 2 + 7 + 27, 2 + 7 + 28, 2 + 7 + 29, 2 + 7 + 30, 2 + 7 + 31, 2 + 7 + 32, 2 + 7 + 33, 2 + 7 + 34, 2 + 7 + 35, 2 + 7 + 36, 2 + 7 + 37. |
| 8 | 2+ 8 + 9, 2 + 8 + 10, 2 + 8 + 11, 2 + 8 + 12, 2 + 8 + 13, 2 + 8 + 14, 2 + 8 + 15, 2 + 8 + 16, 2 + 8 + 17, 2 + 8 + 18, 2 + 8 + 19, 2 + 8 + 20, 2 + 3 + 21, 2 + 8 + 22, 2 + 8 + 23, 2 + 8 + 24, 2 + 8 + 25, 2 + 8 + 26, 2 + 8 + 27, 2 + 8 + 28, 2 + 8 + 29, 2 + 8 + 30, 2 + 8 + 31, 2 + 8 + 32, 2 + 8 + 33, 2 + 8 + 34, 2 + 8 + 35, 2 + 8 + 36, 2 + 8 + 37. |
| 9 | 2 + 9 + 10, 2 + 9 + 11, 2 + 9 + 12, 2 + 9 + 13, 2 + 9 + 14, 2 + 9 + 15, 2 + 9 + 16, 2 + 9 + 17, 2 + 9 + 18, 2 + 9 + 19, 2 + 9 + 20, 2 + 9 + 21, 2 + 9 + 22, 2 + 9 + 23, 2 + 9 + 24, 2 + 9 + 25, 2 + 9 + 26, 2 + 9 + 27, 2 + 9 + 28, 2 + 9 + 29, 2 + 9 + 30, 2 + 9 + 31, 2 + 9 + 32, 2 + 9 + 33, 2 + 9 + 34, 2 + 9 + 35, 2 + 9 + 36, 2 + 9 + 37. |
| 10 | 2 + 10 + 11, 2 + 10 + 12, 2 + 10 + 13, 2 + 10 + 14, 2 + 10 + 15, 2 + 10 + 16, 2 + 10 + 17, 2 + 10 + 18, 2 + 10 + 19, 2 + 10 + 20, 2 + 10 + 21, 2 + 10 + 22, 2 + 10 + 23, 2 + 10 + 24, 2 + 10 + 25, 2 + 10 + 26, 2 + 10 + 27, 2 + 10 + 28, 2 + 10 + 29, 2 + 10 + 30, 2 + 10 + 31, 2 + 10 + 32, 2 + 10 + 33, 2 + 10 + 34, 2 + 10 + 35, 2 + 10 + 36, 2 + 10 + 37. |
| 11 | 2 + 11 + 12, 2 + 11 + 13, 2 + 11 + 14, 2 + 11 + 15, 2 + 11 + 16, 2 + 11 + 17, 2 + 11 + 18, 2 + 11 + 19, 2 + 11 + 20, 2 + 11 + 21, 2 + 11 + 22, 2 + 11 + 23, 2 + 11 + 24, 2 + 11 + 25, 2 + 11 + 26, 2 + 11 + 27, 2 + 11 + 28, 2 + 11 + 29, 2 + 11 + 30, 2 + 11 + 31, 2 + 11 + 32, 2 + 11 + 33, 2 + 11 + 34, 2 + 11 + 35, 2 + 11 + 36, 2 + 11 + 37. |
| 12 | 2 + 12 + 13, 2 + 12 + 14, 2 + 12 + 15, 2 + 12 + 16, 2 + 12 + 17, 2 + 12 + 18, 2 + 12 + 19, 2 + 12 + 20, 2 + 12 + 21, 2 + 12 + 22, 2 + 12 + 23, 2 + 12 + 24, 2 + 12 + 25, 2 + 12 + 26, 2 + 12 + 27, 2 + 12 + 28, 2 + 12 + 29, 2 + 12 + 30, 2 + 12 + 31, 2 + 12 + 32, 2 + 12 + 33, 2 + 12 + 34, 2 + 12 + 35, 2 + 12 + 36, 2 + 12 + 37. |

TABLE 3-continued

Borneol family of terpene formulations.
The numbers refer to the terpenes from Table 1.
The designation "family" is only for convenience in presentation, as other tables also include formulations with borneol.

Each disclosure of three terpenes represents a distinct formulation. In one embodiment, the formulation that is described by the indicated mixture of the three terpenes does not include any additional terpenes. In other embodiments, it does include additional terpenes.

| Subfamily | |
|---|---|
| 13 | 2 + 13 + 14, 2 + 13 + 15, 2 + 13 + 16, 2 + 13 + 17, 2 + 13 + 18, 2 + 13 + 19, 2 + 13 + 20, 2 + 13 + 21, 2 + 13 + 22, 2 + 13 + 23, 2 + 13 + 24, 2 + 13 + 25, 2 + 13 + 26, 2 + 13 + 27, 2 + 13 + 28, 2 + 13 + 29, 2 + 13 + 30, 2 + 13 + 31, 2 + 13 + 32, 2 + 13 + 33, 2 + 13 + 34, 2 + 13 + 35, 2 + 13 + 36, 2 + 13 + 37. |
| 14 | 2 + 14 + 15, 2 + 14 + 16, 2 + 14 + 17, 2 + 14 + 18, 2 + 14 + 19, 2 + 14 + 20, 2 + 14 + 21, 2 + 14 + 22, 2 + 14 + 23, 2 + 14 + 24, 2 + 14 + 25, 2 + 14 + 26, 2 + 14 + 27, 2 + 14 + 28, 2 + 14 + 29, 2 + 14 + 30, 2 + 14 + 31, 2 + 14 + 32, 2 + 14 + 33, 2 + 14 + 34, 2 + 14 + 35, 2 + 14 + 36, 2 + 14 + 37. |
| 15 | 2 + 15 + 16, 2 + 15 + 17, 2 + 15 + 18, 2 + 15 + 19, 2 + 15 + 20, 2 + 15 + 21, 2 + 15 + 22, 2 + 15 + 23, 2 + 15 + 24, 2 + 15 + 25, 2 + 15 + 26, 2 + 15 + 27, 2 + 15 + 28, 2 + 15 + 29, 2 + 15 + 30, 2 + 15 + 31, 2 + 15 + 32, 2 + 15 + 33, 2 + 15 + 34, 2 + 15 + 35, 2 + 15 + 36, 2 + 15 + 37. |
| 16 | 2 + 16 + 17, 2 + 16 + 18, 2 + 16 + 19, 2 + 16 + 20, 2 + 16 + 21, 2 + 16 + 22, 2 + 16 + 23, 2 + 16 + 24, 2 + 16 + 25, 2 + 16 + 26, 2 + 16 + 27, 2 + 16 + 28, 2 + 16 + 29, 2 + 16 + 30, 2 + 16 + 31, 2 + 16 + 32, 2 + 16 + 33, 2 + 16 + 34, 2 + 16 + 35, 2 + 16 + 36, 2 + 16 + 37. |
| 17 | 2 + 17 + 18, 2 + 17 + 19, 2 + 17 + 20, 2 + 17 + 21, 2 + 17 + 22, 2 + 17 + 23, 2 + 17 + 24, 2 + 17 + 25, 2 + 17 + 26, 2 + 17 + 27, 2 + 17 + 28, 2 + 17 + 29, 2 + 17 + 30, 2 + 17 + 31, 2 + 17 + 32, 2 + 17 + 33, 2 + 17 + 34, 2 + 17 + 35, 2 + 17 + 37. |
| 18 | 2 + 18 + 19, 2 + 18 + 20, 2 + 18 + 21, 2 + 18 + 22, 2 + 18 + 23, 2 + 18 + 24, 2 + 18 + 25, 2 + 18 + 26, 2 + 18 + 27, 2 + 18 + 28, 2 + 18 + 29, 2 + 18 + 30, 2 + 18 + 31, 2 + 18 + 32, 2 + 18 + 33, 2 + 18 + 34, 2 + 18 + 35, 2 + 18 + 36, 2 +18 + 37. |
| 19 | 2 + 19 + 20, 2 + 19 + 21, 2 + 19 + 22, 2 + 19 + 23, 2 + 19 + 24, 2 + 19 + 25, 2 + 19 + 26, 2 + 19 + 27, 2 + 19 + 28, 2 + 19 + 29, 2 + 19 + 30, 2 + 19 + 31, 2 + 19 + 32, 2 + 19 + 33, 2 + 19 + 34, 2 + 19 + 35, 2 + 19 + 36, 2 + 19 + 37. |
| 20 | 2 + 20 + 21, 2 + 20 + 22, 2 + 20 + 23, 2 + 20 + 24, 2 + 20 + 25, 2 + 20 + 26, 2 + 20 + 27, 2 + 20 + 28, 2 + 20 + 29, 2 + 20 + 30, 2 + 20 + 31, 2 + 20 + 32, 2 + 20 + 33, 2 + 20 + 34, 2 + 20 + 35, 2 + 20 + 36, 2 + 20 +37. |
| 21 | 2 + 21 + 22, 2 + 21 + 23, 2 + 21 + 24, 2 + 21 + 25, 2 + 21 + 26, 2 + 21 + 27, 2 + 21 + 28, 2 + 21 + 29, 2 + 21 + 30, 2 + 21 + 31, 2 + 21 + 32, 2 + 21 + 33, 2 + 21 + 34, 2 + 21 + 35, 2 + 21 + 36, 2 + 21 + 37. |
| 22 | 2 + 22 + 23, 2 + 22 + 24, 2 + 22 + 25, 2 + 22 + 26, 2 + 22 + 27, 2 + 22 + 28, 2 + 22 + 29, 2 + 22 + 30, 2 + 22 + 31, 2 + 22 + 32, 2 + 22 + 33, 2 + 22 + 34, 2 + 22 + 35, 2 + 22 + 36, 2 + 22 + 37. |
| 23 | 2 + 23 + 24, 2 + 23 + 25, 2 + 23 + 26, 2 + 23 + 27, 2 + 23 + 28, 2 + 23 + 29, 2 + 23 + 30, 2 + 23 + 31, 2 + 23 + 32, 2 + 23 + 33, 2 + 23 + 34, 2 + 23 + 35, 2 + 23 + 36, 2 + 23 + 37. |
| 24 | 2 + 24 + 25, 2 + 24 + 26, 2 + 24 + 27, 2 + 24 + 28, 2 + 24 + 29, 2 + 24 + 30, 2 + 24 + 31, 2 + 24 + 32, 2 + 24 + 33, 2 + 24 + 34, 2 + 24 + 35, 2 + 24 + 36, 2 + 24 + 37. |
| 25 | 2 + 25 + 26, 2 + 25 + 27, 2 + 25 + 28, 2 + 25 + 29, 2 + 25 + 30, 2 + 25 + 31, 2 + 25 + 32, 2 + 25 + 33, 2 + 25 + 34, 2 + 25 + 35, 2 + 25 + 36, 2 + 25 + 37. |
| 26 | 2 + 26 + 27, 2 + 26 + 28, 2 + 26 + 29, 2 + 26 + 30, 2 + 26 + 31, 2 + 26 + 32, 2 + 26 + 33, 2 + 26 + 34, 2 + 26 + 35, 2 + 26 + 36, 2 + 26 + 37. |
| 27 | 2 + 27 + 28, 2 + 27 + 29, 2 + 27 + 30, 2 + 27 + 31, 2 + 27 + 32, 2 + 27 + 33, 2 + 27 + 34, 2 + 27 + 35, 2 + 27 + 36, 2 + 27 + 37. |
| 28 | 2 + 28 + 29, 2 + 28 + 30, 2 + 28 + 31, 2 + 28 + 32, 2 + 28 + 33, 2 + 28 + 34, 2 + 28 + 35, 2 + 28 + 36, 2 + 28 + 37. |
| 29 | 2 + 29 + 30, 2 + 29 + 31, 2 + 29 + 32, 2 + 29 + 33, 2 + 29 + 34, 2 + 29 + 35, 2 + 29 + 36, 2 + 29 + 37. |
| 30 | 2 + 30 + 31, 2 + 30 + 32, 2 + 30 + 33, 2 + 30 + 34, 2 + 30 + 35, 2 + 30 + 36, 2 + 30 + 37. |
| 31 | 2 + 31 + 32, 2 + 31 + 33, 2 + 31 + 34, 2 + 31 + 35, 2 + 31 + 36, 2 + 31 + 37. |
| 32 | 2 + 32 + 33, 2 + 32 + 34, 2 + 32 + 35, 2 + 32 + 36, 2 + 32 + 37. |
| 33 | 2 + 33 + 34, 2 + 33 + 35, 2 + 33 + 36, 2 + 33 + 37. |
| 34 | 2 + 34 + 35, 2 + 34 + 36, 2 + 34 + 37. |
| 35 | 2 + 35 + 36, 2 + 35 + 37. |
| 36 | 2 + 36 + 37. |

TABLE 4

Camphene family of terpene formulations.
The numbers refer to the terpenes from Table 1.
The designation "family" is only for convenience in presentation, as other tables also include formulations with camphene.

Each disclosure of three terpenes represents a distinct formulation. In one embodiment, the formulation that is described by the indicated mixture of the three terpenes does not include any addition terpenes. In other embodiments, it does include additional terpenes.

| Subfamily | |
|---|---|
| 4 | 3 + 4 + 5, 3 + 4 + 6, 3 + 4 + 7, 3 + 4 + 8, 3 + 4 + 9, 3 + 4 + 10, 3 + 4 + 11, 3 + 4 + 12, 3 + 4 + 13, 3 + 4 + 14, 3 + 4 + 15, 3 + 4 + 16, 3 + 4 + 17, 3 + 4 + 18, 3 + 4 + 19, 3 + 4 + 20, 3 + 4 + 21, 3 + 4 + 22, 3 + 4 + 23, 3 + 4 + 24, 3 + 4 + 25, 3 + 4 + 26, 3 + 4 + 27, 3 + 4 + 28, 3 + 4 + 29, 3 + 4 + 30, 3 + 4 + 31, 3 + 4 + 32, 3 + 4 + 33, 3 + 4 + 34, 3 + 4 + 35, 3 + 4 + 36, 3 + 4 + 37. |

TABLE 4-continued

Camphene family of terpene formulations.
The numbers refer to the terpenes from Table 1.
The designation "family" is only for convenience in presentation,
as other tables also include formulations with camphene.

Each disclosure of three terpenes represents a distinct formulation. In one embodiment, the formulation that is described by the indicated mixture of the three terpenes does not include any addition terpenes. In other embodiments, it does include additional terpenes.

| Sub-family | Formulations |
|---|---|
| 5 | 3 + 5 + 6, 3 + 5 + 7, 3 + 5 + 8, 3 + 5 + 9, 3 + 5 + 10, 3 + 5 + 11, 3 + 5 + 12, 3 + 5 + 13, 3 + 5 + 14, 3 + 5 + 15, 3 + 5 + 16, 3 + 5 + 17, 3 + 5 +18, 3 + 5 + 19, 3 + 5 + 20, 3 + 5 + 21, 3 + 5 + 22, 3 + 5 + 23, 3 + 5 + 24, 3 + 5 + 25, 3 + 5 + 26, 3 + 5 + 27, 3 + 5 + 28, 3 + 5 + 29, 3 + 5 + 30, 3 + 5 + 31, 3 + 5 + 32, 3 + 5 + 33, 3 + 5 + 34, 3 + 5 + 35, 3 + 5 + 36, 3 + 5 + 37. |
| 6 | 3 + 6 + 7, 3 + 6 + 8, 3 + 6 + 9, 3 + 6 + 10, 3 + 6 + 11, 3 + 6 + 12, 3 + 6 + 13, 3 + 6 + 14, 3 + 6 + 15, 3 + 6 + 16, 3 + 6 + 17, 3 + 6 + 18, 3 + 6 + 19, 3 + 6 + 20, 3 + 6 + 21, 3 + 6 + 22, 3 + 6 + 23, 3 + 6 + 24, 3 + 6 + 25, 3 + 6 + 26, 3 + 6 + 27, 3 + 6 + 28, 3 + 6 + 29, 3 + 6 + 30, 3 + 6 + 31, 3 + 6 + 32, 3 + 6 + 33, 3 + 6 + 34, 3 + 6 + 35, 3 + 6 + 36, 3 + 6 + 37. |
| 7 | 3 + 7 + 8, 3 + 7 + 9, 3 + 7 +10, 3 + 7 + 11, 3 + 7 + 12, 3 + 7 + 13, 3 + 7 + 14, 3 + 7 + 15, 3 + 7 + 16, 3 + 7 + 17, 3 + 7 + 18, 3 + 7 + 19, 3 + 7 + 20, 3 + 7 + 21, 3 + 7 + 22, 3 + 7 + 23, 3 + 7 + 24, 3 + 7 + 25, 3 + 7 + 26, 3 + 7 + 27, 3 + 7 + 28, 3 + 7 + 29, 3 + 7 + 29, 3 + 7 + 30, 3 + 7 + 31, 3 + 7 + 32, 3 + 7 + 33, 3 + 7 + 34, 3 + 7 + 35, 3 + 7 + 36, 3 + 7 + 37. |
| 8 | 3 + 8 + 9, 3 + 8 + 10, 3 + 8 + 11, 3 + 8 + 12, 3 + 8 + 13, 3 + 8 + 14, 3 + 8 + 15, 3 + 8 + 16, 3 + 8 + 17, 3 + 8 + 18, 3 + 8 + 19, 3 + 8 + 20, 3 + 8 + 21, 3 + 8 + 22, 3 + 8 + 23, 3 + 8 + 24, 3 + 8 + 25, 3 + 8 + 26, 3 + 8 + 27, 3 + 8 + 28, 3 + 8 + 29, 3 + 8 + 30, 3 + 8 + 31, 3 + 8 + 32, 3 + 8 + 33, 3 + 8 + 34, 3 + 8 + 35, 3 + 8 + 36, 3 + 8 + 37. |
| 9 | 3 + 9 + 10, 3 + 9 + 11, 3 + 9 + 12, 3 + 9 + 13, 3 + 9 + 14, 3 + 9 + 15, 3 + 9 + 16, 3 + 9 + 17, 3 + 9 + 18, 3 + 9 + 19, 3 + 9 + 20, 3 + 9 + 21, 3 + 9 + 22, 3 + 9 + 23, 3 + 9 + 24, 3 + 9 + 25, 3 + 9 + 26, 3 + 9 + 27, 3 + 9 + 28, 3 + 9 + 29, 3 + 9 + 30, 3 + 9 + 31, 3 + 9 + 32, 3 + 9 + 33, 3 + 9 + 34, 3 + 9 + 35, 3 + 9 + 36, 3 + 9 + 37. |
| 10 | 3 + 10 + 11, 3 + 10 + 12, 3 + 10 + 13, 3 + 10 + 14, 3 + 10 + 15, 3 + 10 + 16, 3 + 10 + 17, 3 + 10 + 18, 3 + 10 + 19, 3 + 10 + 20, 3 + 10 + 21, 3 + 10 + 22, 3 + 10 + 23, 3 + 10 + 24, 3 + 10 + 25, 3 + 10 + 26, 3 + 10 + 27, 3 + 10 + 28, 3 + 10 + 29, 3 + 10 + 30, 3 + 10 + 31, 3 + 10 + 32, 3 + 10 + 33, 3 + 10 + 34, 3 + 10 + 35, 3 + 10 + 36, 3 + 10 + 37. |
| 11 | 3 + 11 + 12, 3 + 11 + 13, 3 + 11 + 14, 3 + 11 + 15, 3 + 11 + 16, 3 + 11 + 17, 3 + 11 + 18, 3 + 11 + 19, 3 + 11 + 20, 3 + 11 + 21, 3 + 11 + 22, 3 + 11 + 23, 3 + 11 + 24, 3 + 11 + 25, 3 + 11 + 26, 3 + 11 + 27, 3 + 11 + 28, 3 + 11 + 29, 3 + 11 + 30, 3 + 11 + 31, 3 + 11 + 32, 3 + 11 + 33, 3 + 11 + 34, 3 + 11 + 35, 3 + 11 + 36, 3 + 11 + 37. |
| 12 | 3 + 12 + 13, 3 + 12 + 14, 3 + 12 + 15, 3 + 12 + 16, 3 + 12 + 17, 3 + 12 + 18, 3 + 12 + 19, 3 + 12 + 20, 3 + 12 + 21, 3 + 12 + 22, 3 + 12 + 23, 3 + 12 + 24, 3 + 12 + 25, 3 + 12 + 26, 3 + 12 + 27, 3 + 12 + 28, 3 + 12 + 29, 3 + 12 + 30, 3 + 12 + 31, 3 + 12 + 32, 3 + 12 + 33, 3 + 12 + 34, 3 + 12 + 35, 3 + 12 + 36, 3 + 12 + 37. |
| 13 | 3 + 13 + 14, 3 + 13 + 15, 3 + 13 + 16, 3 + 13 + 17, 3 + 13 + 18, 3 + 13 + 19, 3 + 13 + 20, 3 + 13 + 21, 3 + 13 + 22, 3 + 13 + 23, 3 + 13 + 24, 3 + 13 + 25, 3 + 13 + 26, 3 + 13 + 27, 3 + 13 + 28, 3 + 13 + 29, 3 + 13 + 30, 3 + 13 + 31, 3 + 13 + 32, 3 + 13 + 33, 3 + 13 + 34, 3 + 13 + 35, 3 + 13 + 36, 3 + 13 + 37. |
| 14 | 3 + 14 + 15, 3 + 14 + 16, 3 + 14 + 17, 3 + 14 + 18, 3 + 14 + 19, 3 + 14 + 20, 3 + 14 + 21, 3 + 14 + 22, 3 + 14 + 23, 3 + 14 + 24, 3 + 14 + 25, 3 + 14 + 26, 3 + 14 + 27, 3 + 14 + 28, 3 + 14 + 29, 3 + 14 + 30, 3 + 14 + 31, 3 + 14 + 32, 3 + 14 + 33, 3 + 14 + 34, 3 + 14 + 35, 3 + 14 + 36, 3 + 14 + 37. |
| 15 | 3 + 15 + 16, 3 + 15 + 17, 3 + 15 + 18, 3 + 15 + 19, 3 + 15 + 20, 3 + 15 + 21, 3 + 15 + 22, 3 + 15 + 23, 3 + 15 + 24, 3 + 15 + 25, 3 + 15 + 26, 3 + 15 + 27, 3 + 15 + 28, 3 + 15 + 29, 3 + 15 + 30, 3 + 15 + 31, 3 + 15 + 32, 3 + 15 + 33, 3 + 15 + 34, 3 + 15 + 35, 3 + 15 + 36, 3 + 15 + 37. |
| 16 | 3 + 16 + 17, 3 + 16 + 18, 3 + 16 + 19, 3 + 16 + 20, 3 + 16 + 21, 3 + 16 + 22, 3 + 16 + 23, 3 + 16 + 24, 3 + 16 + 25, 3 + 16 + 26, 3 + 16 + 27, 3 + 16 + 28, 3 + 16 + 29, 3 + 16 + 30, 3 + 16 + 31, 3 + 16 + 32, 3 + 16 + 33, 3 + 16 + 34, 3 + 16 + 35, 3 + 16 + 36, 3 + 16 + 37. |
| 17 | 3 + 17 + 18, 3 + 17 + 19, 3 + 17 + 20, 3 + 17 + 21, 3 + 17 + 22, 3 + 17 + 23, 3 + 17 + 24, 3 + 17 + 25, 3 + 17 + 26, 3 + 17 + 27, 3 + 17 + 28, 3 + 17 + 29, 3 + 17 + 30, 3 + 17 + 31, 3 + 17 + 32, 3 + 17 + 33, 3 + 17 + 34, 3 + 17 + 35, 3 + 17 + 36, 3 + 17 + 37. |
| 18 | 3 + 18 + 19, 3 + 18 + 20, 3 + 18 + 21, 3 + 18 + 22, 3 + 18 + 23, 3 + 18 + 24, 3 + 18 + 25, 3 + 18 + 26, 3 + 18 + 27, 3 + 18 + 28, 3 + 18 + 29, 3 + 18 + 30, 3 + 18 + 31, 3 + 18 + 32, 3 + 18 + 33, 3 + 18 + 34, 3 + 18 + 35, 3 + 18 + 36, 3 + 18 + 37. |
| 19 | 3 + 19 + 20, 3 + 19 + 21, 3 + 19 + 22, 3 + 19 + 23, 3 + 19 + 24, 3 + 19 + 25, 3 + 19 + 26, 3 + 19 + 27, 3 + 19 + 28, 3 + 19 + 29, 3 + 19 + 30, 3 + 19 + 31, 3 + 19 + 32, 3 + 19 + 33, 3 + 19 + 34, 3 + 19 + 35, 3 + 19 + 36, 3 + 19 + 37. |
| 20 | 3 + 20 + 21, 3 + 20 + 22, 3 + 20 + 23, 3 + 20 + 24, 3 + 20 + 25, 3 + 20 + 26, 3 + 20 + 27, 3 + 20 + 28, 3 + 20 + 29, 3 + 20 + 30, 3 + 20 + 31, 3 + 20 + 32, 3 + 20 + 33, 3 + 20 + 34, 3 + 20 + 35, 3 + 20 + 36, 3 + 20 + 37. |
| 21 | 3 + 21 + 22, 3 + 21 + 23, 3 + 21 + 24, 3 + 21 + 25, 3 + 21 + 26, 3 + 21 + 27, 3 + 21 + 28, 3 + 21 + 29, 3 + 21 + 30, 3 + 21 + 31, |

TABLE 4-continued

Camphene family of terpene formulations.
The numbers refer to the terpenes from Table 1.
The designation "family" is only for convenience in presentation,
as other tables also include formulations with camphene.

Each disclosure of three terpenes represents a distinct formulation. In one embodiment, the formulation that is described by the indicated mixture of the three terpenes does not include any addition terpenes. In other embodiments, it does include additional terpenes.

| Sub-family | |
|---|---|
|  | 3 + 21 + 32, 3 + 21 + 33, 3 + 21 + 34, 3 + 21 + 35, 3 + 21 + 36,<br>3 + 21 + 37. |
| 22 | 3 + 22 + 23, 3 + 22 + 24, 3 + 22 + 25, 3 + 22 + 26, 3 + 22 + 27,<br>3 + 22 + 28, 3 + 22 + 29, 3 + 22 + 30, 3 + 22 + 31, 3 + 22 + 32,<br>3 + 22 + 33, 3 + 22 + 34, 3 + 22 + 35, 3 + 22 + 36, 3 + 22 + 37. |
| 23 | 3 + 23 + 24, 3 + 23 + 25, 3 + 23 + 26, 3 + 23 + 27, 3 + 23 + 28,<br>3 + 23 + 29, 3 + 23 + 30, 3 + 23 + 31, 3 + 23 + 32, 3 + 23 + 33,<br>3 + 23 + 34, 3 + 23 + 35, 3 + 23 + 36, 3 + 23 + 37. |
| 24 | 3 + 24 + 25, 3 + 24 + 26, 3 + 24 + 27, 3 + 24 + 28, 3 + 24 + 29,<br>3 + 24 + 30, 3 + 24 + 31, 3 + 24 + 32, 3 + 24 + 33, 3 + 24 + 34,<br>3 + 24 + 35, 3 + 24 + 36, 3 + 24 + 37. |
| 25 | 3 + 25 + 26, 3 + 25 + 27, 3 + 25 + 28, 3 + 25 + 29, 3 + 25 + 30,<br>3 + 25 + 31, 3 + 25 + 32, 3 + 25 + 33, 3 + 25 + 34, 3 + 25 + 35,<br>3 + 25 + 36, 3 + 25 + 37. |
| 26 | 3 + 26 + 27, 3 + 26 + 28, 3 + 26 + 29, 3 + 26 + 30, 3 + 26 + 31,<br>3 + 26 + 32, 3 + 26 + 33, 3 + 26 + 34, 3 + 26 + 35, 3 + 26 + 36,<br>3 + 26 + 37. |
| 27 | 3 + 27 + 28, 3 + 27 + 29, 3 + 27 + 30, 3 + 27 + 31, 3 + 27 + 32,<br>3 + 27 + 33, 3 + 27 + 34, 3 + 27 + 35, 3 + 27 + 36, 3 + 27 + 37. |
| 28 | 3 + 28 + 29, 3 + 28 + 30, 3 + 28 + 31, 3 + 28 + 32, 3 + 28 + 33,<br>3 + 28 + 34, 3 + 28 + 35, 3 + 28 + 36, 3 + 28 + 37. |
| 29 | 3 + 29 + 30, 3 + 29 + 31, 3 + 29 + 32, 3 + 29 + 33, 3 + 29 + 34,<br>3 + 29 + 35, 3 + 29 + 36, 3 + 29 + 37. |
| 30 | 3 + 30 + 31, 3 + 30 + 32, 3 + 30 + 33, 3 + 30 + 34, 3 + 30 + 35,<br>3 + 30 + 36, 3 + 30 + 37. |
| 31 | 3 + 31 + 32, 3 + 31 + 33, 3 + 31 + 34, 3 + 31 + 35, 3 + 31 + 36,<br>3 + 31 + 37. |
| 32 | 3 + 32 + 33, 3 + 32 + 34, 3 + 32 + 35, 3 + 32 + 36, 3 + 32 + 37. |
| 33 | 3 + 33 + 34, 3 + 33 + 35, 3 + 33 + 36, 3 + 33 + 37. |
| 34 | 3 + 34 + 35, 3 + 34 + 36, 3 + 34 + 37. |
| 35 | 3 + 35 + 36, 3 + 35 + 37. |

TABLE 5

Camphor family of terpene formulations.
The numbers refer to the terpenes from Table 1. The designation "family" is only for convenience in presentation, as other tables also include formulations with camphor.

Each disclosure of three terpenes represents a distinct formulation. In one embodiment, the formulation that is described by the indicated mixture of the three terpenes does not include any additional terpenes. In other embodiments, it does include additional terpenes.

| Sub-family | |
|---|---|
| 5 | 4 + 5 + 6, 4 + 5 + 7, 4 + 5 + 8, 4 + 5 + 9, 4 + 5 + 10, 4 + 5 + 11,<br>4 + 5 + 12, 4 + 5 + 13, 4 + 5 + 14, 4 + 5 + 15, 4 + 5 + 16, 4 + 5 + 17, 4 + 5 + 18, 4 + 5 + 19, 4 + 5 + 20, 4 + 5 + 21, 4 + 5 + 22,<br>4 + 5 + 23, 4 + 5 + 24, 4 + 5 + 25, 4 + 5 + 26, 4 + 5 + 27, 4 + 5 + 28, 4 + 5 + 29, 4 + 5 + 30, 4 + 5 + 31, 4 + 5 + 32, 4 + 5 + 33, 4 + 5 + 34, 4 + 5 + 35, 4 + 5 + 36, 4 + 5 + 37. |
| 6 | 4 + 6 + 7, 4 + 6 + 8, 4 + 6 + 9, 4 + 6 + 10, 4 + 6 + 11, 4 + 6 + 12,<br>4 + 6 + 13, 4 + 6 + 14, 4 + 6 + 15, 4 + 6 + 16, 4 + 6 + 17, 4 + 6 + 18, 4 + 6 + 19, 4 + 6 + 20, 4 + 6 + 21, 4 + 6 + 22, 4 + 6 + 23,<br>4 + 6 + 24, 4 + 6 + 25, 4 + 6 + 26, 4 + 6 + 27, 4 + 6 + 28, 4 + 6 + 29, 4 + 6 + 30, 4 + 6 + 31, 4 + 6 + 32, 4 + 6 + 33, 4 + 6 + 34, 4 + 6 + 35, 4 + 6 + 36, 4 + 6 + 37. |
| 7 | 4 + 7 + 8, 4 + 7 + 9, 4 + 7 + 10, 4 + 7 + 11, 4 + 7 + 12, 4 + 7 + 13,<br>4 + 7 + 14, 4 + 7 + 15, 4 + 7 + 16, 4 + 7 + 17, 4 + 7 + 18, 4 + 7 + 19, 4 + 7 + 20, 4 + 7 + 21, 4 + 7 + 22, 4 + 7 + 23, 4 + 7 + 24,<br>4 + 7 + 25, 4 + 7 + 26, 4 + 7 + 27, 4 + 7 + 28, 4 + 7 + 29, 4 + 7 + 30, 4 + 7 + 31, 4 + 7 + 32, 4 + 7 + 33, 4 + 7 + 34, 4 + 7 + 35, 4 + 7 + 36, 4 + 7 + 37. |
| 8 | 4 + 8 + 9, 4 + 8 + 10, 4 + 8 + 11, 4 + 8 + 12, 4 + 8 + 13, 4 + 8 + 14, 4 + 8 + 15, 4 + 8 + 16, 4 + 8 + 17, 4 + 8 + 18, 4 + 8 + 19, 4 + 8 + 20, 4 + 8 + 21, 4 + 8 + 22, 4 + 8 + 23, 4 + 8 + 24, 4 + 8 + 25,<br>4 + 8 + 26, 4 + 8 + 27, 4 + 8 + 28, 4 + 8 + 29, 4 + 8 + 30, 4 + 8 + 31, 4 + 8 + 32, 4 + 8 + 33, 4 + 8 + 34, 4 + 8 + 35, 4 + 8 + 36, 4 + 8 + 37. |
| 9 | 4 + 9 + 10, 4 + 9 + 11, 4 + 9 + 12, 4 + 9 + 13, 4 + 9 + 14, 4 + 9 + 15, 4 + 9 + 16, 4 + 9 + 17, 4 + 9 + 18, 4 + 9 + 19, 4 + 9 + 20, 4 + 9 + 21, 4 + 9 + 22, 4 + 9 + 23, 4 + 9 + 24, 4 + 9 + 25, 4 + 9 + 26,<br>4 + 9 + 27, 4 + 9 + 28, 4 + 9 + 29, 4 + 9 + 30, 4 + 9 + 31, 4 + 9 + 32, 4 + 9 + 33, 4 + 9 + 34, 4 + 9 + 35, 4 + 9 + 36, 4 + 9 + 37. |
| 10 | 4 + 10 + 11, 4 + 10 + 12, 4 + 10 + 13, 4 + 10 + 14, 4 + 10 + 15,<br>4 + 10 + 16, 4 + 10 + 17, 4 + 10 + 18, 4 + 10 + 19, 4 + 10 + 20,<br>4 + 10 + 21, 4 + 10 + 22, 4 + 10 + 23, 4 + 10 + 24, 4 + 10 + 25,<br>4 + 10 + 26, 4 + 10 + 27, 4 + 10 + 28, 4 + 10 + 29, 4 + 10 + 30,<br>4 + 10 + 31, 4 + 10 + 32, 4 + 10 + 33, 4 + 10 + 34, 4 + 10 + 35,<br>4 + 10 + 36, 4 + 10 + 37. |
| 11 | 4 + 11 + 12, 4 + 11 + 13, 4 + 11 + 14, 4 + 11 + 15, 4 + 11 + 16,<br>4 + 11 + 17, 4 + 11 + 18, 4 + 11 + 19, 4 + 11 + 20, 4 + 11 + 21,<br>4 + 11 + 22, 4 + 11 + 23, 4 + 11 + 24, 4 + 11 + 25, 4 + 11 + 26,<br>4 + 11 + 27, 4 + 11 + 28, 4 + 11 + 29, 4 + 11 + 30, 4 + 11 + 31,<br>4 + 11 + 32, 4 + 11 + 33, 4 + 11 + 34, 4 + 11 + 35, 4 + 11 + 36,<br>4 + 11 + 37. |
| 12 | 4 + 12 + 13, 4 + 12 + 14, 4 + 12 + 15, 4 + 12 + 16, 4 + 12 + 17,<br>4 + 12 + 18, 4 + 12 + 19, 4 + 12 + 20, 4 + 12 + 21, 4 + 12 + 22,<br>4 + 12 + 23, 4 + 12 + 24, 4 + 12 + 25, 4 + 12 + 26, 4 + 12 + 27,<br>4 + 12 + 28, 4 + 12 + 29, 4 + 12 + 30, 4 + 12 + 31, 4 + 12 + 32,<br>4 + 12 + 33, 4 + 12 + 34, 4 + 12 + 35, 4 + 12 + 36, 4 + 12 + 37. |

TABLE 5-continued

Camphor family of terpene formulations.
The numbers refer to the terpenes from Table 1. The designation "family" is only for convenience in presentation, as other tables also include formulations with camphor.

Each disclosure of three terpenes represents a distinct formulation. In one embodiment, the formulation that is described by the indicated mixture of the three terpenes does not include any additional terpenes. In other embodiments, it does include additional terpenes.

| Sub-family | Formulations |
|---|---|
| 13 | 4 + 13 + 14, 4 + 13 + 15, 4 + 13 + 16, 4 + 13 + 17, 4 + 13 + 18, 4 + 13 + 19, 4 + 13 + 20, 4 + 13 + 21, 4 + 13 + 22, 4 + 13 + 23, 4 + 13 + 24, 4 + 13 + 25, 4 + 13 + 26, 4 + 13 + 27, 4 + 13 + 28, 4 + 13 + 29, 4 + 13 + 30, 4 + 13 + 31, 4 + 13 + 32, 4 + 13 + 33, 4 + 13 + 34, 4 + 13 + 35, 4 + 13 + 36, 4 + 13 + 37. |
| 14 | 4 + 14 + 15, 4 + 14 + 16, 4 + 14 + 17, 4 + 14 + 18, 4 + 14 + 19, 4 + 14 + 20, 4 + 14 + 21, 4 + 14 + 22, 4 + 14 + 23, 4 + 14 + 24, 4 + 14 + 25, 4 + 14 + 26, 4 + 14 + 27, 4 + 14 + 28, 4 + 14 + 29, 4 + 14 + 30, 4 + 14 + 31, 4 + 14 + 32, 4 + 14 + 33, 4 + 14 + 34, 4 + 14 + 35, 4 + 14 + 36, 4 + 14 + 37. |
| 15 | 4 + 15 + 16, 4 + 15 + 17, 4 + 15 + 18, 4 + 15 + 19, 4 + 15 + 20, 4 + 15 + 21, 4 + 15 + 22, 4 + 15 + 23, 4 + 15 + 24, 4 + 15 + 25, 4 + 15 + 26, 4 + 15 + 27, 4 + 15 + 28, 4 + 15 + 29, 4 + 15 + 30, 4 + 15 + 31, 4 + 15 + 32, 4 + 15 + 33, 4 + 15 + 34, 4 + 15 + 35, 4 + 15 + 36, 4 + 15 + 37. |
| 16 | 4 + 16 + 17, 4 + 16 + 18, 4 + 16 + 19, 4 + 16 + 20, 4 + 16 + 21, 4 + 16 + 22, 4 + 16 + 23, 4 + 16 + 24, 4 + 16 + 25, 4 + 16 + 26, 4 + 16 + 27, 4 + 16 + 28, 4 + 16 + 29, 4 + 16 + 30, 4 + 16 + 31, 4 + 16 + 32, 4 + 16 + 33, 4 + 16 + 34, 4 + 16 + 35, 4 + 16 + 36, 4 + 16 + 37. |
| 17 | 4 + 17 + 18, 4 + 17 + 19, 4 + 17 + 20, 4 + 17 + 21, 4 + 17 + 22, 4 + 17 + 23, 4 + 17 + 24, 4 + 17 + 25, 4 + 17 + 26, 4 + 17 + 27, 4 + 17 + 28, 4 + 17 + 29, 4 + 17 + 30, 4 + 17 + 31, 4 + 17 + 32, 4 + 17 + 33, 4 + 17 + 34, 4 + 17 + 35, 4 + 17 + 36, 4 + 17 + 37. |
| 18 | 4 + 18 + 19, 4 + 18 + 20, 4 + 18 + 21, 4 + 18 + 22, 4 + 18 + 23, 4 + 18 + 24, 4 + 18 + 25, 4 + 18 + 26, 4 + 18 + 27, 4 + 18 + 28, 4 + 18 + 29, 4 + 18 + 30, 4 + 18 + 31, 4 + 18 + 32, 4 + 18 + 33, 4 + 18 + 34, 4 + 18 + 35, 4 + 18 + 36, 4 + 18 + 37. |
| 19 | 4 + 19 + 20, 4 + 19 + 21, 4 + 19 + 22, 4 + 19 + 23, 4 + 19 + 24, 4 + 19 + 25, 4 + 19 + 26, 4 + 19 + 27, 4 + 19 + 28, 4 + 19 + 29, 4 + 19 + 30, 4 + 19 + 31, 4 + 19 + 32, 4 + 19 + 33, 4 + 19 + 34, 4 + 19 + 35, 4 + 19 + 36, 4 + 19 + 37. |
| 20 | 4 + 20 + 21, 4 + 20 + 22, 4 + 20 + 23, 4 + 20 + 24, 4 + 20 + 25, 4 + 20 + 26, 4 + 20 + 27, 4 + 20 + 28, 4 + 20 + 29, 4 + 20 + 30, 4 + 20 + 31, 4 + 20 + 32, 4 + 20 + 33, 4 + 20 + 34, 4 + 20 + 35, 4 + 20 + 36, 4 + 20 + 37. |
| 21 | 4 + 21 + 22, 4 + 21 + 23, 4 + 21 + 24, 4 + 21 + 25, 4 + 21 + 26, 4 + 21 + 27, 4 + 21 + 28, 4 + 21 + 29, 4 + 21 + 30, 4 + 21 + 31, 4 + 21 + 32, 4 + 21 + 33, 4 + 21 + 34, 4 + 21 + 35, 4 + 21 + 36, 4 + 21 + 37. |
| 22 | 4 + 22 + 23, 4 + 22 + 24, 4 + 22 + 25, 4 + 22 + 26, 4 + 22 + 27, 4 + 22 + 28, 4 + 22 + 29, 4 + 22 + 30, 4 + 22 + 31, 4 + 22 + 32, 4 + 22 + 33, 4 + 22 + 34, 4 + 22 + 35, 4 + 22 + 36, 4 + 22 + 37. |
| 23 | 4 + 23 + 24, 4 + 23 + 25, 4 + 23 + 26, 4 + 23 + 27, 4 + 23 + 28, 4 + 23 + 29, 4 + 23 + 30, 4 + 23 + 31, 4 + 23 + 32, 4 + 23 + 33, 4 + 23 + 34, 4 + 23 + 35, 4 + 23 + 36, 4 + 23 + 37. |
| 24 | 4 + 24 + 25, 4 + 24 + 26, 4 + 24 + 27, 4 + 24 + 28, 4 + 24 + 29, 4 + 24 + 30, 4 + 24 + 31, 4 + 24 + 32, 4 + 24 + 33, 4 + 24 + 34, 4 + 24 + 35, 4 + 24 + 36, 4 + 24 + 37. |
| 25 | 4 + 25 + 26, 4 + 25 + 27, 4 + 25 + 28, 4 + 25 + 29, 4 + 25 + 30, 4 + 25 + 31, 4 + 25 + 32, 4 + 25 + 33, 4 + 25 + 34, 4 + 25 + 35, 4 + 25 + 36, 4 + 25 + 37. |
| 26 | 4 + 26 + 27, 4 + 26 + 28, 4 + 26 + 29, 4 + 26 + 30, 4 + 26 + 31, 4 + 26 + 32, 4 + 26 + 33, 4 + 26 + 34, 4 + 26 + 35, 4 + 26 + 36, 4 + 26 + 37. |
| 27 | 4 + 27 + 28, 4 + 27 + 29, 4 + 27 + 30, 4 + 27 + 31, 4 + 27 + 32, 4 + 27 + 33, 4 + 27 + 34, 4 + 27 + 35, 4 + 27 + 36, 4 + 27 + 37. |
| 28 | 4 + 28 + 29, 4 + 28 + 30, 4 + 28 + 31, 4 + 28 + 32, 4 + 28 + 33, 4 + 28 + 34, 4 + 28 + 35, 4 + 28 + 36, 4 + 28 + 37. |
| 29 | 4 + 29 + 30, 4 + 29 + 31, 4 + 29 + 32, 4 + 29 + 33, 4 + 29 + 34, 4 + 29 + 35, 4 + 29 + 36, 4 + 29 + 37. |
| 30 | 4 + 30 + 31, 4 + 30 + 32, 4 + 30 + 33, 4 + 30 + 34, 4 + 30 + 35, 4 + 30 + 36, 4 + 30 + 37. |
| 31 | 4 + 31 + 32, 4 + 31 + 33, 4 + 31 + 34, 4 + 31 + 35, 4 + 31 + 36, 4 + 31 + 37. |
| 32 | 4 + 32 + 33, 4 + 32 + 34, 4 + 32 + 35, 4 + 32 + 36, 4 + 32 + 37. |
| 33 | 4 + 33 + 34, 4 + 33 + 35, 4 + 33 + 36, 4 + 33 + 37. |
| 34 | 4 + 34 + 35, 4 + 34 + 36, 4 + 34 + 37. |
| 35 | 4 + 35 + 36, 4 + 35 + 37. |
| 36 | 4 + 36 + 37. |

TABLE 6

Delta-3-carene family of terpene formulations.
The numbers refer to the terpenes from Table 1. The designation "family" is only for convenience in presentation, as other tables also include formulations with delta-3-carene.

Each disclosure of three terpenes represents a distinct formulation. In one embodiment, the formulation that is described by the indicated mixture of the three terpenes does not include any additional terpenes. In other embodiments, it does include additional terpenes.

| Sub-family | Formulations |
|---|---|
| 6 | 5 + 6 + 7, 5 + 6 + 8, 5 + 6 + 9, 5 + 6 + 10, 5 + 6 + 11, 5 + 6 + 12, 5 + 6 + 13, 5 + 6 + 14, 5 + 6 + 15, 5 + 6 + 16, 5 + 6 + 17, 5 + 6 + 18, 5 + 6 + 19, 5 + 6 + 20, 5 + 6 + 21, 5 + 6 + 22, 5 + 6 + 23, 5 + 6 + 24, 5 + 6 + 25, 5 + 6 + 26, 5 + 6 + 27, 5 + 6 + 28, 5 + 6 + 29, 5 + 6 + 30, 5 + 6 + 31, 5 + 6 + 32, 5 + 6 + 33, 5 + 6 + 34, 5 + 6 + 35, 5 + 6 + 36, 5 + 6 + 37. |

TABLE 6-continued

Delta-3-carene family of terpene formulations.
The numbers refer to the terpenes from Table 1. The designation "family" is only for convenience in presentation, as other tables also include formulations with delta-3-carene.

Each disclosure of three terpenes represents a distinct formulation. In one embodiment, the formulation that is described by the indicated mixture of the three terpenes does not include any additional terpenes. In other embodiments, it does include additional terpenes.

| Sub-family | Formulations |
|---|---|
| 7 | 5 + 7 + 8, 5 + 7 + 9, 5 + 7 + 10, 5 + 7 + 11, 5 + 7 + 12, 5 + 7 + 13, 5 + 7 + 14, 5 + 7 + 15, 5 + 7 + 16, 5 + 7 + 17, 5 + 7 + 18, 5 + 7 + 19, 5 + 7 + 20, 5 + 7 + 21, 5 + 7 + 22, 5 + 7 + 23, 5 + 7 + 24, 5 + 7 + 25, 5 + 7 + 26, 5 + 7 + 27, 5 + 7 + 28, 5 + 7 + 29, 5 + 7 + 30, 5 + 7 + 31, 5 + 7 + 32, 5 + 7 + 33, 5 + 7 + 34, 5 + 7 + 35, 5 + 7 + 36, 5 + 7 + 37. |
| 8 | 5 + 8 + 9, 5 + 8 + 10, 5 + 8 + 11, 5 + 8 + 12, 5 + 8 + 13, 5 + 8 + 14, 5 + 8 + 15, 5 + 8 + 16, 5 + 8 + 17, 5 + 8 + 18, 5 + 8 + 19, 5 + 8 + 20, 5 + 8 + 21, 5 + 8 + 22, 5 + 8 + 23, 5 + 8 + 24, 5 + 8 + 25, 5 + 8 + 26, 5 + 8 + 27, 5 + 8 + 28, 5 + 8 + 29, 5 + 8 + 30, 5 + 8 + 31, 5 + 8 + 32, 5 + 8 + 33, 5 + 8 + 34, 5 + 8 + 35, 5 + 8 + 36, 5 + 8 + 37. |
| 9 | 5 + 9 + 10, 5 + 9 + 11, 5 + 9 + 12, 5 + 9 + 13, 5 + 9 + 14, 5 + 9 + 15, 5 + 9 + 16, 5 + 9 + 17, 5 + 9 + 18, 5 + 9 + 19, 5 + 9 + 20, 5 + 9 + 21, 5 + 9 + 22, 5 + 9 + 23, 5 + 9 + 24, 5 + 9 + 25, 5 + 9 + 26, 5 + 9 + 27, 5 + 9 + 28, 5 + 9 + 29, 5 + 9 + 30, 5 + 9 + 31, 5 + 9 + 32, 5 + 9 + 33, 5 + 9 + 34, 5 + 9 + 35, 5 + 9 + 36, 5 + 9 + 37. |
| 10 | 5 + 10 + 11, 5 + 10 + 12, 5 + 10 + 13, 5 + 10 + 14, 5 + 10 + 15, 5 + 10 + 16, 5 + 10 + 17, 5 + 10 + 18, 5 + 10 + 19, 5 + 10 + 20, 5 + 10 + 21, 5 + 10 + 22, 5 + 10 + 23, 5 + 10 + 24, 5 + 10 + 25, 5 + 10 + 26, 5 + 10 + 27, 5 + 10 + 28, 5 + 10 + 29, 5 + 10 + 30, 5 + 10 + 31, 5 + 10 + 32, 5 + 10 + 33, 5 + 10 + 34, 5 + 10 + 35, 5 + 10 + 36, 5 + 10 + 37. |
| 11 | 5 + 11 + 12, 5 + 11 + 13, 5 + 11 + 14, 5 + 11 + 15, 5 + 11 + 16, 5 + 11 + 17, 5 + 11 + 18, 5 + 11 + 19, 5 + 11 + 20, 5 + 11 + 21, 5 + 11 + 22, 5 + 11 + 23, 5 + 11 + 24, 5 + 11 + 25, 5 + 11 + 26, 5 + 11 + 27, 5 + 11 + 28, 5 + 11 + 29, 5 + 11 + 30, 5 + 11 + 31, 5 + 11 + 32, 5 + 11 + 33, 5 + 11 + 34, 5 + 11 + 35, 5 + 11 + 36, 5 + 11 + 37. |
| 12 | 5 + 12 + 13, 5 + 12 + 14, 5 + 12 + 15, 5 + 12 + 16, 5 + 12 + 17, 5 + 12 + 18, 5 + 12 + 19, 5 + 12 + 20, 5 + 12 + 21, 5 + 12 + 22, 5 + 12 + 23, 5 + 12 + 24, 5 + 12 + 25, 5 + 12 + 26, 5 + 12 + 27, 5 + 12 + 28, 5 + 12 + 29, 5 + 12 + 30, 5 + 12 + 31, 5 + 12 + 32, 5 + 12 + 33, 5 + 12 + 34, 5 + 12 + 35, 5 + 12 + 36, 5 + 12 + 37. |
| 13 | 5 + 13 + 14, 5 + 13 + 15, 5 + 13 + 16, 5 + 13 + 17, 5 + 13 + 18, 5 + 13 + 19, 5 + 13 + 20, 5 + 13 + 21, 5 + 13 + 22, 5 + 13 + 23, 5 + 13 + 24, 5 + 13 + 25, 5 + 13 + 26, 5 + 13 + 27, 5 + 13 + 28, 5 + 13 + 29, 5 + 13 + 30, 5 + 13 + 31, 5 + 13 + 32, 5 + 13 + 33, 5 + 13 + 34, 5 + 13 + 35, 5 + 13 + 36, 5 + 13 + 37. |
| 14 | 5 + 14 + 15, 5 + 14 + 16, 5 + 14 + 17, 5 + 14 + 18, 5 + 14 + 19, 5 + 14 + 20, 5 + 14 + 21, 5 + 14 + 22, 5 + 14 + 23, 5 + 14 + 24, 5 + 14 + 25, 5 + 14 + 26, 5 + 14 + 27, 5 + 14 + 28, 5 + 14 + 29, 5 + 14 + 30, 5 + 14 + 31, 5 + 14 + 32, 5 + 14 + 33, 5 + 14 + 34, 5 + 14 + 35, 5 + 14 + 36, 5 + 14 + 37. |
| 15 | 5 + 15 + 16, 5 + 15 + 17, 5 + 15 + 18, 5 + 15 + 19, 5 + 15 + 20, 5 + 15 + 21, 5 + 15 + 22, 5 + 15 + 23, 5 + 15 + 24, 5 + 15 + 25, 5 + 15 + 26, 5 + 15 + 27, 5 + 15 + 28, 5 + 15 + 29, 5 + 15 + 30, 5 + 15 + 31, 5 + 15 + 32, 5 + 15 + 33, 5 + 15 + 34, 5 + 15 + 35, 5 + 15 + 36, 5 + 15 + 37. |
| 16 | 5 + 16 + 17, 5 + 16 + 18, 5 + 16 + 19, 5 + 16 + 20, 5 + 16 + 21, 5 + 16 + 22, 5 + 16 + 23, 5 + 16 + 24, 5 + 16 + 25, 5 + 16 + 26, 5 + 16 + 27, 5 + 16 + 28, 5 + 16 + 29, 5 + 16 + 30, 5 + 16 + 31, 5 + 16 + 32, 5 + 16 + 33, 5 + 16 + 34, 5 + 16 + 35, 5 + 16 + 36, 5 + 16 + 37. |
| 17 | 5 + 17 + 18, 5 + 17 + 19, 5 + 17 + 20, 5 + 17 + 21, 5 + 17 + 22, 5 + 17 + 23, 5 + 17 + 24, 5 + 17 + 25, 5 + 17 + 26, 5 + 17 + 27, 5 + 17 + 28, 5 + 17 + 29, 5 + 17 + 30, 5 + 17 + 31, 5 + 17 + 32, 5 + 17 + 33, 5 + 17 + 34, 5 + 17 + 35, 5 + 17 + 36, 5 + 17 + 37. |
| 18 | 5 + 18 + 19, 5 + 18 + 20, 5 + 18 + 21, 5 + 18 + 22, 5 + 18 + 23, 5 + 18 + 24, 5 + 18 + 25, 5 + 18 + 26, 5 + 18 + 27, 5 + 18 + 28, 5 + 18 + 29, 5 + 18 + 30, 5 + 18 + 31, 5 + 18 + 32, 5 + 18 + 33, 5 + 18 + 34, 5 + 18 + 35, 5 + 18 + 36, 5 + 18 + 37. |
| 19 | 5 + 19 + 20, 5 + 19 + 21, 5 + 19 + 22, 5 + 19 + 23, 5 + 19 + 24, 5 + 19 + 25, 5 + 19 + 26, 5 + 19 + 27, 5 + 19 + 28, 5 + 19 + 29, 5 + 19 + 30, 5 + 19 + 31, 5 + 19 + 32, 5 + 19 + 33, 5 + 19 + 34, 5 + 19 + 35, 5 + 19 + 36, 5 + 19 + 37. |
| 20 | 5 + 20 + 21, 5 + 20 + 22, 5 + 20 + 23, 5 + 20 + 24, 5 + 20 + 25, 5 + 20 + 26, 5 + 20 + 27, 5 + 20 + 28, 5 + 20 + 29, 5 + 20 + 30, 5 + 20 + 31, 5 + 20 + 32, 5 + 20 + 33, 5 + 20 + 34, 5 + 20 + 35, 5 + 20 + 36, 5 + 20 + 37. |
| 21 | 5 + 21 + 22, 5 + 21 + 23, 5 + 21 + 24, 5 + 21 + 25, 5 + 21 + 26, 5 + 21 + 27, 5 + 21 + 28, 5 + 21 + 29, 5 + 21 + 30, 5 + 21 + 31, 5 + 21 + 32, 5 + 21 + 33, 5 + 21 + 34, 5 + 21 + 35, 5 + 21 + 36, 5 + 21 + 37. |
| 22 | 5 + 22 + 23, 5 + 22 + 24, 5 + 22 + 25, 5 + 22 + 26, 5 + 22 + 27, 5 + 22 + 28, 5 + 22 + 29, 5 + 22 + 30, 5 + 22 + 31, 5 + 22 + 32, 5 + 22 + 33, 5 + 22 + 34, 5 + 22 + 35, 5 + 22 + 36, 5 + 22 + 37. |
| 23 | 5 + 23 + 24, 5 + 23 + 25, 5 + 23 + 26, 5 + 23 + 27, 5 + 23 + 28, 5 + 23 + 29, 5 + 23 + 30, 5 + 23 + 31, 5 + 23 + 32, 5 + 23 + 33, 5 + 23 + 34, 5 + 23 + 35, 5 + 23 + 36, 5 + 23 + 37. |

TABLE 6-continued

Delta-3-carene family of terpene formulations.
The numbers refer to the terpenes from Table 1. The
designation "family" is only for convenience in presentation,
as other tables also include formulations with delta-3-carene.

Each disclosure of three terpenes represents a distinct
formulation. In one embodiment, the formulation that
is described by the indicated mixture of the three
terpenes does not include any additional terpenes. In
other embodiments, it does include additional terpenes.

| Sub-family | |
|---|---|
| 24 | 5 + 24 + 25, 5 + 24 + 26, 5 + 24 + 27, 5 + 24 + 28, 5 + 24 + 29, 5 + 24 + 30, 5 + 24 + 31, 5 + 24 + 32, 5 + 24 + 33, 5 + 24 + 34, 5 + 24 + 35, 5 + 24 + 36, 5 + 24 + 37. |
| 25 | 5 + 25 + 26, 5 + 25 + 27, 5 + 25 + 28, 5 + 25 + 29, 5 + 25 + 30, 5 + 25 + 31, 5 + 25 + 32, 5 + 25 + 33, 5 + 25 + 34, 5 + 25 + 35, 5 + 25 + 36, 5 + 25 + 37. |
| 26 | 5 + 26 + 27, 5 + 26 + 28, 5 + 26 + 29, 5 + 26 + 30, 5 + 26 + 31, 5 + 26 + 32, 5 + 26 + 33, 5 + 26 + 34, 5 + 26 + 35, 5 + 26 + 36, 5 + 26 + 37. |
| 27 | 5 + 27 + 28, 5 + 27 + 29, 5 + 27 + 30, 5 + 27 + 31, 5 + 27 + 32, 5 + 27 + 33, 5 + 27 + 34, 5 + 27 + 35, 5 + 27 + 36, 5 + 27 + 37. |
| 28 | 5 + 28 + 29, 5 + 28 + 30, 5 + 28 + 31, 5 + 28 + 32, 5 + 28 + 33, 5 + 28 + 34, 5 + 28 + 35, 5 + 28 + 36, 5 + 28 + 37. |
| 29 | 5 + 29 + 30, 5 + 29 + 31, 5 + 29 + 32, 5 + 29 + 33, 5 + 29 + 34, 5 + 29 + 35, 5 + 29 + 36, 5 + 29 + 37 |
| 30 | 5 + 30 + 31, 5 + 30 + 32, 5 + 30 + 33, 5 + 30 + 34, 5 + 30 + 35, 5 + 30 + 36, 5 + 30 + 37. |
| 31 | 5 + 31 + 32, 5 + 31 + 33, 5 + 31 + 34, 5 + 31 + 35, 5 + 31 + 36, 5 + 31 + 37. |
| 32 | 5 + 32 + 33, 5 + 32 + 34, 5 + 32 + 35, 5 + 32 + 36, 5 + 32 + 37. |
| 33 | 5 + 33 + 34, 5 + 33 + 35, 5 + 33 + 36, 5 + 33 + 37. |
| 34 | 5 + 34 + 35, 5 + 34 + 36, 5 + 34 + 37. |
| 35 | 5 + 35 + 36, 5 + 35 + 37. |
| 36 | 5 + 36 + 37. |

TABLE 7

Beta-caryophyllene family of terpene formulations.
The numbers refer to the terpenes from Table 1. The
designation "family" is only for convenience in presentation,
as other tables also include formulations with beta-caryophyllene.

Each disclosure of three terpenes represents a distinct
formulation. In one embodiment, the formulation that
is described by the indicated mixture of the three
terpenes does not include any additional terpenes. In
other embodiments, it does include additional terpenes.

| Sub-family | |
|---|---|
| 7 | 6 + 7 + 8, 6 + 7 + 9, 6 + 7 + 10, 6 + 7 + 11, 6 + 7 + 12, 6 + 7 + 13, 6 + 7 + 14, 6 + 7 + 15, 6 + 7 + 16, 6 + 7 + 17, 6 + 7 + 18, 6 + 7 + 19, 6 + 7 + 20, 6 + 7 + 21, 6 + 7 + 22, 6 + 7 + 23, 6 + 7 + 24, 6 + 7 + 25, 6 + 7 + 26, 6 + 7 + 27, 6 + 7 + 28, 6 + 7 + 29, 6 + 7 + 30, 6 + 7 + 31, 6 + 7 + 32, 6 + 7 + 33, 6 + 7 + 34, 6 + 7 + 35, 6 + 7 + 36, 6 + 7 + 37. |
| 8 | 6 + 8 + 9, 6 + 8 + 10, 6 + 8 + 11, 6 + 8 + 12, 6 + 8 + 13, 6 + 8 + 14, 6 + 8 + 15, 6 + 8 + 16, 6 + 8 + 17, 6 + 8 + 18, 6 + 8 + 19, 6 + 8 + 20, 6 + 8 + 21, 6 + 8 + 22, 6 + 8 + 23, 6 + 8 + 24, 6 + 8 + 25, 6 + 8 + 26, 6 + 8 + 27, 6 + 8 + 28, 6 + 8 + 29, 6 + 8 + 30, 6 + 8 + 31, 6 + 8 + 32, 6 + 8 + 33, 6 + 8 + 34, 6 + 8 + 35, 6 + 8 + 36, 6 + 8 + 37. |

TABLE 7-continued

Beta-caryophyllene family of terpene formulations.
The numbers refer to the terpenes from Table 1. The
designation "family" is only for convenience in presentation,
as other tables also include formulations with beta-caryophyllene.

Each disclosure of three terpenes represents a distinct
formulation. In one embodiment, the formulation that
is described by the indicated mixture of the three
terpenes does not include any additional terpenes. In
other embodiments, it does include additional terpenes.

| Sub-family | |
|---|---|
| 9 | 6 + 9 + 10, 6 + 9 + 11, 6 + 9 + 12, 6 + 9 + 13, 6 + 9 + 14, 6 + 9 + 15, 6 + 9 + 16, 6 + 9 + 17, 6 + 9 + 18, 6 + 9 + 19, 6 + 9 + 20, 6 + 9 + 21, 6 + 9 + 22, 6 + 9 + 23, 6 + 9 + 24, 6 + 9 + 25, 6 + 9 + 26, 6 + 9 + 27, 6 + 9 + 28, 6 + 9 + 29, 6 + 9 + 30, 6 + 9 + 31, 6 + 9 + 32, 6 + 9 + 33, 6 + 9 + 34, 6 + 9 + 35, 6 + 9 + 36, 6 + 9 + 37. |
| 10 | 6 + 10 + 11, 6 + 10 + 12, 6 + 10 + 13, 6 + 10 + 14, 6 + 10 + 15, 6 + 10 + 16, 6 + 10 + 17, 6 + 10 + 18, 6 + 10 + 19, 6 + 10 + 20, 6 + 10 + 21, 6 + 10 + 22, 6 + 10 + 23, 6 + 10 + 24, 6 + 10 + 25, 6 + 10 + 26, 6 + 10 + 27, 6 + 10 + 28, 6 + 10 + 29, 6 + 10 + 30, 6 + 10 + 31, 6 + 10 + 32, 6 + 10 + 33, 6 + 10 + 34, 6 + 10 + 35, 6 + 10 + 36, 6 + 10 + 37. |
| 11 | 6 + 11 + 12, 6 + 11 + 13, 6 + 11 + 14, 6 + 11 + 15, 6 + 11 + 16, 6 + 11 + 17, 6 + 11 + 18, 6 + 11 + 19, 6 + 11 + 20, 6 + 11 + 21, 6 + 11 + 22, 6 + 11 + 23, 6 + 11 + 24, 6 + 11 + 25, 6 + 11 + 26, 6 + 11 + 27, 6 + 11 + 28, 6 + 11 + 29, 6 + 11 + 30, 6 + 11 + 31, 6 + 11 + 32, 6 + 11 + 33, 6 + 11 + 34, 6 + 11 + 35, 6 + 11 + 36, 6 + 11 + 37. |
| 12 | 6 + 12 + 13, 6 + 12 + 14, 6 + 12 + 15, 6 + 12 + 16, 6 + 12 + 17, 6 + 12 + 18, 6 + 12 + 19, 6 + 12 + 20, 6 + 12 + 21, 6 + 12 + 22, 6 + 12 + 23, 6 + 12 + 24, 6 + 12 + 25, 6 + 12 + 26, 6 + 12 + 27, 6 + 12 + 28, 6 + 12 + 29, 6 + 12 + 30, 6 + 12 + 31, 6 + 12 + 32, 6 + 12 + 33, 6 + 12 + 34, 6 + 12 + 35, 6 + 12 + 36, 6 + 12 + 37. |
| 13 | 6 + 13 + 14, 6 + 13 + 15, 6 + 13 + 16, 6 + 13 + 17, 6 + 13 + 18, 6 + 13 + 19, 6 + 13 + 20, 6 + 13 + 21, 6 + 13 + 22, 6 + 13 + 23, 6 + 13 + 24, 6 + 13 + 25, 6 + 13 + 26, 6 + 13 + 27, 6 + 13 + 28, 6 + 13 + 29, 6 + 13 + 30, 6 + 13 + 31, 6 + 13 + 32, 6 + 13 + 33, 6 + 13 + 34, 6 + 13 + 35, 6 + 13 + 36, 6 + 13 + 37. |
| 14 | 6 + 14 + 15, 6 + 14 + 16, 6 + 14 + 17, 6 + 14 + 18, 6 + 14 + 19, 6 + 14 + 20, 6 + 14 + 21, 6 + 14 + 22, 6 + 14 + 23, 6 + 14 + 24, 6 + 14 + 25, 6 + 14 + 26, 6 + 14 + 27, 6 + 14 + 28, 6 + 14 + 29, 6 + 14 + 30, 6 + 14 + 31, 6 + 14 + 32, 6 + 14 + 33, 6 + 14 + 34, 6 + 14 + 35, 6 + 14 + 36, 6 + 14 + 37. |
| 15 | 6 + 15 + 16, 6 + 15 + 17, 6 + 15 + 18, 6 + 15 + 19, 6 + 15 + 20, 6 + 15 + 21, 6 + 15 + 22, 6 + 15 + 23, 6 + 15 + 24, 6 + 15 + 25, 6 + 15 + 26, 6 + 15 + 27, 6 + 15 + 28, 6 + 15 + 29, 6 + 15 + 30, 6 + 15 + 31, 6 + 15 + 32, 6 + 15 + 33, 6 + 15 + 34, 6 + 15 + 35, 6 + 15 + 36, 6 + 15 + 37. |
| 16 | 6 + 16 + 17, 6 + 16 + 18, 6 + 16 + 19, 6 + 16 + 20, 6 + 16 + 21, 6 + 16 + 22, 6 + 16 + 23, 6 + 16 + 24, 6 + 16 + 25, 6 + 16 + 26, 6 + 16 + 27, 6 + 16 + 28, 6 + 16 + 29, 6 + 16 + 30, 6 + 16 + 31, |

TABLE 7-continued

Beta-caryophyllene family of terpene formulations.
The numbers refer to the terpenes from Table 1. The designation "family" is only for convenience in presentation, as other tables also include formulations with beta-caryophyllene.

Each disclosure of three terpenes represents a distinct formulation. In one embodiment, the formulation that is described by the indicated mixture of the three terpenes does not include any additional terpenes. In other embodiments, it does include additional terpenes.

| Sub-family | |
|---|---|
| | 6 + 16 + 32, 6 + 16 + 33, 6 + 16 + 34, 6 + 16 + 35, 6 + 16 + 36, <br> 6 + 16 + 37. |
| 17 | 6 + 17 + 18, 6 + 17 + 19, 6 + 17 + 20, 6 + 17 + 21, 6 + 17 + 22, <br> 6 + 17 + 23, 6 + 17 + 24, 6 + 17 + 25, 6 + 17 + 26, 6 + 17 + 27, <br> 6 + 17 + 28, 6 + 17 + 29, 6 + 17 + 30, 6 + 17 + 31, 6 + 17 + 32, <br> 6 + 17 + 33, 6 + 17 + 34, 6 + 17 + 35, 6 + 17 + 36, 6 + 17 + 37. |
| 18 | 6 + 18 + 19, 6 + 18 + 20, 6 + 18 + 21, 6 + 18 + 22, 6 + 18 + 23, <br> 6 + 18 + 24, 6 + 18 + 25, 6 + 18 + 26, 6 + 18 + 27, 6 + 18 + 28, <br> 6 + 18 + 29, 6 + 18 + 30, 6 + 18 + 31, 6 + 18 + 32, 6 + 18 + 33, <br> 6 + 18 + 34, 6 + 18 + 35, 6 + 18 + 36, 6 + 18 + 37. |
| 19 | 6 + 19 + 20, 6 + 19 + 21, 6 + 19 + 22, 6 + 19 + 23, 6 + 19 + 24, <br> 6 + 19 + 25, 6 + 19 + 26, 6 + 19 + 27, 6 + 19 + 28, 6 + 19 + 29, <br> 6 + 19 + 30, 6 + 19 + 31, 6 + 19 + 32, 6 + 19 + 33, 6 + 19 + 34, <br> 6 + 19 + 35, 6 + 19 + 36, 6 + 19 + 37. |
| 20 | 6 + 20 + 21, 6 + 20 + 22, 6 + 20 + 23, 6 + 20 + 24, 6 + 20 + 25, <br> 6 + 20 + 26, 6 + 20 + 27, 6 + 20 + 28, 6 + 20 + 29, 6 + 20 + 30, <br> 6 + 20 + 31, 6 + 20 + 32, 6 + 20 + 33, 6 + 20 + 34, 6 + 20 + 35, <br> 6 + 20 + 36, 6 + 20 + 37. |
| 21 | 6 + 21 + 22, 6 + 21 + 23, 6 + 21 + 24, 6 + 21 + 25, 6 + 21 + 26, <br> 6 + 21 + 27, 6 + 21 + 28, 6 + 21 + 29, 6 + 21 + 30, 6 + 21 + 31, <br> 6 + 21 + 32, 6 + 21 + 33, 6 + 21 + 34, 6 + 21 + 35, 6 + 21 + 36, <br> 6 + 21 + 37. |
| 22 | 6 + 22 + 23, 6 + 22 + 24, 6 + 22 + 25, 6 + 22 + 26, 6 + 22 + 27, <br> 6 + 22 + 28, 6 + 22 + 29, 6 + 22 + 30, 6 + 22 + 31, 6 + 22 + 32, <br> 6 + 22 + 33, 6 + 22 + 34, 6 + 22 + 35, 6 + 22 + 36, 6 + 22 + 37. |
| 23 | 6 + 23 + 24, 6 + 23 + 25, 6 + 23 + 26, 6 + 23 + 27, 6 + 23 + 28, <br> 6 + 23 + 29, 6 + 23 + 30, 6 + 23 + 31, 6 + 23 + 32, 6 + 23 + 33, <br> 6 + 23 + 34, 6 + 23 + 35, 6 + 23 + 36, 6 + 23 + 37. |
| 24 | 6 + 24 + 25, 6 + 24 + 26, 6 + 24 + 27, 6 + 24 + 28, 6 + 24 + 29, <br> 6 + 24 + 30, 6 + 24 + 31, 6 + 24 + 32, 6 + 24 + 33, 6 + 24 + 34, <br> 6 + 24 + 35, 6 + 24 + 36, 6 + 24 + 37. |
| 25 | 6 + 25 + 26, 6 + 25 + 27, 6 + 25 + 28, 6 + 25 + 29, 6 + 25 + 30, <br> 6 + 25 + 31, 6 + 25 + 32, 6 + 25 + 33, 6 + 25 + 34, 6 + 25 + 35, <br> 6 + 25 + 36, 6 + 25 + 37. |
| 26 | 6 + 26 + 27, 6 + 26 + 28, 6 + 26 + 29, 6 + 26 + 30, 6 + 26 + 31, <br> 6 + 26 + 32, 6 + 26 + 33, 6 + 26 + 34, 6 + 26 + 35, 6 + 26 + 36, <br> 6 + 26 + 37. |
| 27 | 6 + 27 + 28, 6 + 27 + 29, 6 + 27 + 30, 6 + 27 + 31, 6 + 27 + 32, <br> 6 + 27 + 33, 6 + 27 + 34, 6 + 27 + 35, 6 + 27 + 36, 6 + 27 + 37. |
| 28 | 6 + 28 + 29, 6 + 28 + 30, 6 + 28 + 31, 6 + 28 + 32, 6 + 28 + 33, <br> 6 + 28 + 34, 6 + 28 + 35, 6 + 28 + 36, 6 + 28 + 37. |
| 29 | 6 + 29 + 30, 6 + 29 + 31, 6 + 29 + 32, 6 + 29 + 33, 6 + 29 + 34, <br> 6 + 29 + 35, 6 + 29 + 36, 6 + 29 + 37 |
| 30 | 6 + 30 + 31, 6 + 30 + 32, 6 + 30 + 33, 6 + 30 + 34, 6 + 30 + 35, <br> 6 + 30 + 36, 6 + 30 + 37. |
| 31 | 6 + 31 + 32, 6 + 31 + 33, 6 + 31 + 34, 6 + 31 + 35, 6 + 31 + 36, <br> 6 + 31 + 37. |
| 32 | 6 + 32 + 33, 6 + 32 + 34, 6 + 32 + 35, 6 + 32 + 36, 6 + 32 + 37. |
| 33 | 6 + 33 + 34, 6 + 33 + 35, 6 + 33 + 36, 6 + 33 + 37. |
| 34 | 6 + 34 + 35, 6 + 34 + 36, 6 + 34 + 37. |
| 35 | 6 + 35 + 36, 6 + 35 + 37. |
| 36 | 6 + 36 + 37. |

TABLE 8

Alpha-cedrene family of terpene formulations.
The numbers refer to the terpenes from Table 1. The designation "family" is only for convenience in presentation, as other tables also include formulations with alpha-cedrene.

Each disclosure of three terpenes represents a distinct formulation. In one embodiment, the formulation that is described by the indicated mixture of the three terpenes does not include any additional terpenes. In other embodiments, it does include additional terpenes.

| Sub-family | |
|---|---|
| 9 | 8 + 9 + 10, 8 + 9 + 11, 8 + 9 + 12, 8 + 9 + 13, 8 + 9 + 14, 8 + 9 + 15, 8 + 9 + 16, 8 + 9 + 17, 8 + 9 + 18, 8 + 9 + 19, 8 + 9 + 20, 8 + 9 + 21, 8 + 9 + 22, 8 + 9 + 23, 8 + 9 + 24, 8 + 9 + 25, 8 + 9 + 26, 8 + 9 + 27, 8 + 9 + 28, 8 + 9 + 29, 8 + 9 + 30, 8 + 9 + 31, 8 + 9 + 32, 8 + 9 + 33, 8 + 9 + 34, 8 + 9 + 35, 8 + 9 + 36, 8 + 9 + 37. |
| 10 | 8 + 10 + 11, 8 + 10 + 12, 8 + 10 + 13, 8 + 10 + 14, 8 + 10 + 15, <br> 8 + 10 + 16, 8 + 10 + 17, 8 + 10 + 18, 8 + 10 + 19, 8 + 10 + 20, <br> 8 + 10 + 21, 8 + 10 + 22, 8 + 10 + 23, 8 + 10 + 24, 8 + 10 + 25, <br> 8 + 10 + 26, 8 + 10 + 27, 8 + 10 + 28, 8 + 10 + 29, 8 + 10 + 30, <br> 8 + 10 + 31, 8 + 10 + 32, 8 + 10 + 33, 8 + 10 + 34, 8 + 10 + 35, <br> 8 + 10 + 36, 8 + 10 + 37. |
| 11 | 8 + 11 + 12, 8 + 11 + 13, 8 + 11 + 14, 8 + 11 + 15, 8 + 11 + 16, <br> 8 + 11 + 17, 8 + 11 + 18, 8 + 11 + 19, 8 + 11 + 20, 8 + 11 + 21, <br> 8 + 11 + 22, 8 + 11 + 23, 8 + 11 + 24, 8 + 11 + 25, 8 + 11 + 26, <br> 8 + 11 + 27, 8 + 11 + 28, 8 + 11 + 29, 8 + 11 + 30, 8 + 11 + 31, <br> 8 + 11 + 32, 8 + 11 + 33, 8 + 11 + 34, 8 + 11 + 35, 8 + 11 + 36, <br> 8 + 11 + 37. |
| 12 | 8 + 12 + 13, 8 + 12 + 14, 8 + 12 + 15, 8 + 12 + 16, 8 + 12 + 17, <br> 8 + 12 + 18, 8 + 12 + 19, 8 + 12 + 20, 8 + 12 + 21, 8 + 12 + 22, <br> 8 + 12 + 23, 8 + 12 + 24, 8 + 12 + 25, 8 + 12 + 26, 8 + 12 + 27, <br> 8 + 12 + 28, 8 + 12 + 29, 8 + 12 + 30, 8 + 12 + 31, 8 + 12 + 32, <br> 8 + 12 + 33, 8 + 12 + 34, 8 + 12 + 35, 8 + 12 + 36, 8 + 12 + 37. |

TABLE 8-continued

Alpha-cedrene family of terpene formulations.
The numbers refer to the terpenes from Table 1. The
designation "family" is only for convenience in presentation,
as other tables also include formulations with alpha-cedrene.

Each disclosure of three terpenes represents a distinct
formulation. In one embodiment, the formulation
that is described by the indicated mixture of the three
terpenes does not include any additional terpenes. In
other embodiments, it does include additional terpenes.

| Sub-family | |
|---|---|
| 13 | 8 + 13 + 14, 8 + 13 + 15, 8 + 13 + 16, 8 + 13 + 17, 8 + 13 + 18, 8 + 13 + 19, 8 + 13 + 20, 8 + 13 + 21, 8 + 13 + 22, 8 + 13 + 23, 8 + 13 + 24, 8 + 13 + 25, 8 + 13 + 26, 8 + 13 + 27, 8 + 13 + 28, 8 + 13 + 29, 8 + 13 + 30, 8 + 13 + 31, 8 + 13 + 32, 8 + 13 + 33, 8 + 13 + 34, 8 + 13 + 35, 8 + 13 + 36, 8 + 13 + 37. |
| 14 | 8 + 14 + 15, 8 + 14 + 16, 8 + 14 + 17, 8 + 14 + 18, 8 + 14 + 19, 8 + 14 + 20, 8 + 14 + 21, 8 + 14 + 22, 8 + 14 + 23, 8 + 14 + 24, 8 + 14 + 25, 8 + 14 + 26, 8 + 14 + 27, 8 + 14 + 28, 8 + 14 + 29, 8 + 14 + 30, 8 + 14 + 31, 8 + 14 + 32, 8 + 14 + 33, 8 + 14 + 34, 8 + 14 + 35, 8 + 14 + 36, 8 + 14 + 37. |
| 15 | 8 + 15 + 16, 8 + 15 + 17, 8 + 15 + 18, 8 + 15 + 19, 8 + 15 + 20, 8 + 15 + 21, 8 + 15 + 22, 8 + 15 + 23, 8 + 15 + 24, 8 + 15 + 25, 8 + 15 + 26, 8 + 15 + 27, 8 + 15 + 28, 8 + 15 + 29, 8 + 15 + 30, 8 + 15 + 31, 8 + 15 + 32, 8 + 15 + 33, 8 + 15 + 34, 8 + 15 + 35, 8 + 15 + 36, 8 + 15 + 37. |
| 16 | 8 + 16 + 17, 8 + 16 + 18, 8 + 16 + 19, 8 + 16 + 20, 8 + 16 + 21, 8 + 16 + 22, 8 + 16 + 23, 8 + 16 + 24, 8 + 16 + 25, 8 + 16 + 26, 8 + 16 + 27, 8 + 16 + 28, 8 + 16 + 29, 8 + 16 + 30, 8 + 16 + 31, 8 + 16 + 32, 8 + 16 + 33, 8 + 16 + 34, 8 + 16 + 35, 8 + 16 + 36, 8 + 16 + 37. |
| 17 | 8 + 17 + 18, 8 + 17 + 19, 8 + 17 + 20, 8 + 17 + 21, 8 + 17 + 22, 8 + 17 + 23, 8 + 17 + 24, 8 + 17 + 25, 8 + 17 + 26, 8 + 17 + 27, 8 + 17 + 28, 8 + 17 + 29, 8 + 17 + 30, 8 + 17 + 31, 8 + 17 + 32, 8 + 17 + 33, 8 + 17 + 34, 8 + 17 + 35, 8 + 17 + 36, 8 + 17 + 37. |
| 18 | 8 + 18 + 19, 8 + 18 + 20, 8 + 18 + 21, 8 + 18 + 22, 8 + 18 + 23, 8 + 18 + 24, 8 + 18 + 25, 8 + 18 + 26, 8 + 18 + 27, 8 + 18 + 28, 8 + 18 + 29, 8 + 18 + 30, 8 + 18 + 31, 8 + 18 + 32, 8 + 18 + 33, 8 + 18 + 34, 8 + 18 + 35, 8 + 18 + 36, 8 + 18 + 37. |
| 19 | 8 + 19 + 20, 8 + 19 + 21, 8 + 19 + 22, 8 + 19 + 23, 8 + 19 + 24, 8 + 19 + 25, 8 + 19 + 26, 8 + 19 + 27, 8 + 19 + 28, 8 + 19 + 29, 8 + 19 + 30, 8 + 19 + 31, 8 + 19 + 32, 8 + 19 + 33, 8 + 19 + 34, 8 + 19 + 35, 8 + 19 + 36, 8 + 19 + 37. |
| 20 | 8 + 20 + 21, 8 + 20 + 22, 8 + 20 + 23, 8 + 20 + 24, 8 + 20 + 25, 8 + 20 + 26, 8 + 20 + 27, 8 + 20 + 28, 8 + 20 + 29, 8 + 20 + 30, 8 + 20 + 31, 8 + 20 + 32, 8 + 20 + 33, 8 + 20 + 34, 8 + 20 + 35, 8 + 20 + 36, 8 + 20 + 37. |
| 21 | 8 + 21 + 22, 8 + 21 + 23, 8 + 21 + 24, 8 + 21 + 25, 8 + 21 + 26, 8 + 21 + 27, 8 + 21 + 28, 8 + 21 + 29, 8 + 21 + 30, 8 + 21 + 31, 8 + 21 + 32, 8 + 21 + 33, 8 + 21 + 34, 8 + 21 + 35, 8 + 21 + 36, 8 + 21 + 37. |
| 22 | 8 + 22 + 23, 8 + 22 + 24, 8 + 22 + 25, 8 + 22 + 26, 8 + 22 + 27, 8 + 22 + 28, 8 + 22 + 29, 8 + 22 + 30, 8 + 22 + 31, 8 + 22 + 32, 8 + 22 + 33, 8 + 22 + 34, 8 + 22 + 35, 8 + 22 + 36, 8 + 22 + 37. |
| 23 | 8 + 23 + 24, 8 + 23 + 25, 8 + 23 + 26, 8 + 23 + 27, 8 + 23 + 28, 8 + 23 + 29, 8 + 23 + 30, 8 + 23 + 31, 8 + 23 + 32, 8 + 23 + 33, 8 + 23 + 34, 8 + 23 + 35, 8 + 23 + 36, 8 + 23 + 37. |
| 24 | 8 + 24 + 25, 8 + 24 + 26, 8 + 24 + 27, 8 + 24 + 28, 8 + 24 + 29, 8 + 24 + 30, 8 + 24 + 31, 8 + 24 + 32, 8 + 24 + 33, 8 + 24 + 34, 8 + 24 + 35, 8 + 24 + 36, 8 + 24 + 37. |
| 25 | 8 + 25 + 26, 8 + 25 + 27, 8 + 25 + 28, 8 + 25 + 29, 8 + 25 + 30, 8 + 25 + 31, 8 + 25 + 32, 8 + 25 + 33, 8 + 25 + 34, 8 + 25 + 35, 8 + 25 + 36, 8 + 25 + 37. |
| 26 | 8 + 26 + 27, 8 + 26 + 28, 8 + 26 + 29, 8 + 26 + 30, 8 + 26 + 31, 8 + 26 + 32, 8 + 26 + 33, 8 + 26 + 34, 8 + 26 + 35, 8 + 26 + 36, 8 + 26 + 37. |
| 27 | 8 + 27 + 28, 8 + 27 + 29, 8 + 27 + 30, 8 + 27 + 31, 8 + 27 + 32, 8 + 27 + 33, 8 + 27 + 34, 8 + 27 + 35, 8 + 27 + 36, 8 + 27 + 37. |
| 28 | 8 + 28 + 29, 8 + 28 + 30, 8 + 28 + 31, 8 + 28 + 32, 8 + 28 + 33, 8 + 28 + 34, 8 + 28 + 35, 8 + 28 + 36, 8 + 28 + 37. |
| 29 | 8 + 29 + 30, 8 + 29 + 31, 8 + 29 + 32, 8 + 29 + 33, 8 + 29 + 34, 8 + 29 + 35, 8 + 29 + 36, 8 + 29 + 37. |
| 30 | 8 + 30 + 31, 8 + 30 + 32, 8 + 30 + 33, 8 + 30 + 34, 8 + 30 + 35, 8 + 30 + 36, 8 + 30 + 37. |
| 31 | 8 + 31 + 32, 8 + 31 + 33, 8 + 31 + 34, 8 + 31 + 35, 8+ 31 + 36, 8 + 31 + 37. |
| 32 | 8 + 32 + 33, 8 + 32 + 34, 8 + 32 + 35, 8 + 32 + 36, 8 + 32 + 37. |
| 33 | 8 + 33 + 34, 8 + 33 + 35, 8 + 33 + 36, 8 + 33 + 37. |
| 34 | 8 + 34 + 35, 8 + 34 + 36, 8 + 34 + 37. |
| 35 | 8 + 35 + 36, 8 + 35 + 37. |
| 36 | 8 + 36 + 37. |

TABLE 9

Beta-eudesmol family of terpene formulations.
The numbers refer to the terpenes from Table 1. The
designation "family" is only for convenience in presentation,
as other tables also include formulations with beta-eudesmol.

Each disclosure of three terpenes represents a distinct
formulation. In one embodiment, the formulation
that is described by the indicated mixture of the three
terpenes does not include any addition terpenes. In
other embodiments, it does include additional terpenes.

| Sub-family | |
|---|---|
| 10 | 9 + 10 + 11, 9 + 10 + 12, 9 + 10 + 13, 9 + 10 + 14, 9 + 10 + 15, 9 + 10 + 16, 9 + 10 + 17, 9 + 10 + 18, 9 + 10 + 19, 9 + 10 + 20, 9 + 10 + 21, 9 + 10 + 22, 9 + 10 + 23, 9 + 10 + 24, 9 + 10 + 25, 9 + 10 + 26, 9 + 10 + 27, 9 + 10 + 28, 9 + 10 + 29, 9 + 10 + 30, |

TABLE 9-continued

Beta-eudesmol family of terpene formulations.
The numbers refer to the terpenes from Table 1. The designation "family" is only for convenience in presentation, as other tables also include formulations with beta-eudesmol.

Each disclosure of three terpenes represents a distinct formulation. In one embodiment, the formulation that is described by the indicated mixture of the three terpenes does not include any addition terpenes. In other embodiments, it does include additional terpenes.

| Sub-family | Formulations |
|---|---|
| | 9 + 10 + 31, 9 + 10 + 32, 9 + 10 + 33, 9 + 10 + 34, 9 + 10 + 35, 9 + 10 + 36, 9 + 10 + 37. |
| 11 | 9 + 11 + 12, 9 + 11 + 13, 9 + 11 + 14, 9 + 11 + 15, 9 + 11 + 16, 9 + 11 + 17, 9 + 11 + 18, 9 + 11 + 19, 9 + 11 + 20, 9 + 11 + 21, 9 + 11 + 22, 9 + 11 + 23, 9 + 11 + 24, 9 + 11 + 25, 9 + 11 + 26, 9 + 11 + 27, 9 + 11 + 28, 9 + 11 + 29, 9 + 11 + 30, 9 + 11 + 31, 9 + 11 + 32, 9 + 11 + 33, 9 + 11 + 34, 9 + 11 + 35, 9 + 11 + 36, 9 + 11 + 37. |
| 12 | 9 + 12 + 13, 9 + 12 + 14, 9 + 12 + 15, 9 + 12 + 16, 9 + 12 + 17, 9 + 12 + 18, 9 + 12 + 19, 9 + 12 + 20, 9 + 12 + 21, 9 + 12 + 22, 9 + 12 + 23, 9 + 12 + 24, 9 + 12 + 25, 9 + 12 + 26, 9 + 12 + 27, 9 + 12 + 28, 9 + 12 + 29, 9 + 12 + 30, 9 + 12 + 31, 9 + 12 + 32, 9 + 12 + 33, 9 + 12 + 34, 9 + 12 + 35, 9 + 12 + 36, 9 + 12 + 37. |
| 13 | 9 + 13 + 14, 9 + 13 + 15, 9 + 13 + 16, 9 + 13 + 17, 9 + 13 + 18, 9 + 13 + 19, 9 + 13 + 20, 9 + 13 + 21, 9 + 13 + 22, 9 + 13 + 23, 9 + 13 + 24, 9 + 13 + 25, 9 + 13 + 26, 9 + 13 + 27, 9 + 13 + 28, 9 + 13 + 29, 9 + 13 + 30, 9 + 13 + 31, 9 + 13 + 32, 9 + 13 + 33, 9 + 13 + 34, 9 + 13 + 35, 9 + 13 + 36, 9 + 13 + 37. |
| 14 | 9 + 14 + 15, 9 + 14 + 16, 9 + 14 + 17, 9 + 14 + 18, 9 + 14 + 19, 9 + 14 + 20, 9 + 14 + 21, 9 + 14 + 22, 9 + 14 + 23, 9 + 14 + 24, 9 + 14 + 25, 9 + 14 + 26, 9 + 14 + 27, 9 + 14 + 28, 9 + 14 + 29, 9 + 14 + 30, 9 + 14 + 31, 9 + 14 + 32, 9 + 14 + 33, 9 + 14 + 34, 9 + 14 + 35, 9 + 14 + 36, 9 + 14 + 37. |
| 15 | 9 + 15 + 16, 9 + 15 + 17, 9 + 15 + 18, 9 + 15 + 19, 9 + 15 + 20, 9 + 15 + 21, 9 + 15 + 22, 9 + 15 + 23, 9 + 15 + 24, 9 + 15 + 25, 9 + 15 + 26, 9 + 15 + 27, 9 + 15 + 28, 9 + 15 + 29, 9 + 15 + 30, 9 + 15 + 31, 9 + 15 + 32, 9 + 15 + 33, 9 + 15 + 34, 9 + 15 + 35, 9 + 15 + 36, 9 + 15 + 37. |
| 16 | 9 + 16 + 17, 9 + 16 + 18, 9 + 16 + 19, 9 + 16 + 20, 9 + 16 + 21, 9 + 16 + 22, 9 + 16 + 23, 9 + 16 + 24, 9 + 16 + 25, 9 + 16 + 26, 9 + 16 + 27, 9 + 16 + 28, 9 + 16 + 29, 9 + 16 + 30, 9 + 16 + 31, 9 + 16 + 32, 9 + 16 + 33, 9 + 16 + 34, 9 + 16 + 35, 9 + 16 + 36, 9 + 16 + 37. |
| 17 | 9 + 17 + 18, 9 + 17 + 19, 9 + 17 + 20, 9 + 17 + 21, 9 + 17 + 22, 9 + 17 + 23, 9 + 17 + 24, 9 + 17 + 25, 9 + 17 + 26, 9 + 17 + 27, 9 + 17 + 28, 9 + 17 + 29, 9 + 17 + 30, 9 + 17 + 31, 9 + 17 + 32, 9 + 17 + 33, 9 + 17 + 34, 9 + 17 + 35, 9 + 17 + 36, 9 + 17 + 37. |
| 18 | 9 + 18 + 19, 9 + 18 + 20, 9 + 18 + 21, 9 + 18 + 22, 9 + 18 + 23, 9 + 18 + 24, 9 + 18 + 25, 9 + 18 + 26, 9 + 18 + 27, 9 + 18 + 28, 9 + 18 + 29, 9 + 18 + 30, 9 + 18 + 31, 9 + 18 + 32, 9 + 18 + 33, 9 + 18 + 34, 9 + 18 + 35, 9 + 18 + 36, 9 + 18 + 37. |
| 19 | 9 + 19 + 20, 9 + 19 + 21, 9 + 19 + 22, 9 + 19 + 23, 9 + 19 + 24, 9 + 19 + 25, 9 + 19 + 26, 9 + 19 + 27, 9 + 19 + 28, 9 + 19 + 29, 9 + 19 + 30, 9 + 19 + 31, 9 + 19 + 32, 9 + 19 + 33, 9 + 19 + 34, 9 + 19 + 35, 9 + 19 + 36, 9 + 19 + 37. |
| 20 | 9 + 20 + 21, 9 + 20 + 22, 9 + 20 + 23, 9 + 20 + 24, 9 + 20 + 25, 9 + 20 + 26, 9 + 20 + 27, 9 + 20 + 28, 9 + 20 + 29, 9 + 20 + 30, 9 + 20 + 31, 9 + 20 + 32, 9 + 20 + 33, 9 + 20 + 34, 9 + 20 + 35, 9 + 20 + 36, 9 + 20 + 37. |
| 21 | 9 + 21 + 22, 9 + 21 + 23, 9 + 21 + 24, 9 + 21 + 25, 9 + 21 + 26, 9 + 21 + 27, 9 + 21 + 28, 9 + 21 + 29, 9 + 21 + 30, 9 + 21 + 31, 9 + 21 + 32, 9 + 21 + 33, 9 + 21 + 34, 9 + 21 + 35, 9 + 21 + 36, 9 + 21 + 37. |
| 22 | 9 + 22 + 23, 9 + 22 + 24, 9 + 22 + 25, 9 + 22 + 26, 9 + 22 + 27, 9 + 22 + 28, 9 + 22 + 29, 9 + 22 + 30, 9 + 22 + 31, 9 + 22 + 32, 9 + 22 + 33, 9 + 22 + 34, 9 + 22 + 35, 9 + 22 + 36, 9 + 22 + 37. |
| 23 | 9 + 23 + 24, 9 + 23 + 25, 9 + 23 + 26, 9 + 23 + 27, 9 + 23 + 28, 9 + 23 + 29, 9 + 23 + 30, 9 + 23 + 31, 9 + 23 + 32, 9 + 23 + 33, 9 + 23 + 34, 9 + 23 + 35, 9 + 23 + 36, 9 + 23 + 37. |
| 24 | 9 + 24 + 25, 9 + 24 + 26, 9 + 24 + 27, 9 + 24 + 28, 9 + 24 + 29, 9 + 24 + 30, 9 + 24 + 31, 9 + 24 + 32, 9 + 24 + 33, 9 + 24 + 34, 9 + 24 + 35, 9 + 24 + 36, 9 + 24 + 37. |
| 25 | 9 + 25 + 26, 9 + 25 + 27, 9 + 25 + 28, 9 + 25 + 29, 9 + 25 + 30, 9 + 25 + 31, 9 + 25 + 32, 9 + 25 + 33, 9 + 25 + 34, 9 + 25 + 35, 9 + 25 + 36, 9 + 25 + 37. |
| 26 | 9 + 26 + 27, 9 + 26 + 28, 9 + 26 + 29, 9 + 26 + 30, 9 + 26 + 31, 9 + 26 + 32, 9 + 26 + 33, 9 + 26 + 34, 9 + 26 + 35, 9 + 26 + 36, 9 + 26 + 37. |
| 27 | 9 + 27 + 28, 9 + 27 + 29, 9 + 27 + 30, 9 + 27 + 31, 9 + 27 + 32, 9 + 27 + 33, 9 + 27 + 34, 9 + 27 + 35, 9 + 27 + 36, 9 + 27 + 37. |
| 28 | 9 + 28 + 29, 9 + 28 + 30, 9 + 28 + 31, 9 + 28 + 32, 9 + 28 + 33, 9 + 28 + 34, 9 + 28 + 35, 9 + 28 + 36, 9 + 28 + 37. |
| 29 | 9 + 29 + 30, 9 + 29 + 31, 9 + 29 + 32, 9 + 29 + 33, 9 + 29 + 34, 9 + 29 + 35, 9 + 29 + 36, 9 + 29 + 37. |
| 30 | 9 + 30 + 31, 9 + 30 + 32, 9 + 30 + 33, 9 + 30 + 34, 9 + 30 + 35, 9 + 30 + 36, 9 + 30 + 37. |
| 31 | 9 + 31 + 32, 9 + 31 + 33, 9 + 31 + 34, 9 + 31 + 35, 9 + 31 + 36, 9 + 31 + 37. |
| 32 | 9 + 32 + 33, 9 + 32 + 34, 9 + 32 + 35, 9 + 32 + 36, 9 + 32 + 37. |
| 33 | 9 + 33 + 34, 9 + 33 + 35, 9 + 33 + 36, 9 + 33 + 37. |
| 34 | 9 + 34 + 35, 9 + 34 + 36, 9 + 34 + 37. |
| 35 | 9 + 35 + 36, 9 + 35 + 37. |
| 36 | 9 + 36 + 37. |

TABLE 10

Fenchyl alcohol family of terpene formulations.
The numbers refer to the terpenes from Table 1. The
designation "family" is only for convenience in presentation,
as other tables also include formulations with fenchyl alcohol.

Each disclosure of three terpenes represents a distinct formulation. In one embodiment, the formulation that is described by the indicated mixture of the three terpenes does not include any additional terpenes. In other embodiments, it does include additional terpenes.

| Sub-family | |
|---|---|
| 11 | 10 + 11 + 12, 10 + 11 + 13, 10 + 11 + 14, 10 + 11 + 15, 10 + 11 + 16, 10 + 11 + 17, 10 + 11 + 18, 10 + 11 + 19, 10 + 11 + 20, 10 + 11 + 21, 10 + 11 + 22, 10 + 11 + 23, 10 + 11 + 24, 10 + 11 + 25, 10 + 11 + 26, 10 + 11 + 27, 10 + 11 + 28, 10 + 11 + 29, 10 + 11 + 30, 10 + 11 + 31, 10 + 11 + 32, 10 + 11 + 33, 10 + 11 + 34, 10 + 11 + 35, 10 + 11 + 36, 10 + 11 + 37. |
| 12 | 10 + 12 + 13, 10 + 12 + 14, 10 + 12 + 15, 10 + 12 + 16, 10 + 12 + 17, 10 + 12 + 18, 10 + 12 + 19, 10 + 12 + 20, 10 + 12 + 21, 10 + 12 + 22, 10 + 12 + 23, 10 + 12 + 24, 10 + 12 + 25, 10 + 12 + 26, 10 + 12 + 27, 10 + 12 + 28, 10 + 12 + 29, 10 + 12 + 30, 10 + 12 + 31, 10 + 12 + 32, 10 + 12 + 33, 10 + 12 + 34, 10 + 12 + 35, 10 + 12 + 36, 10 + 12 + 37. |
| 13 | 10 + 13 + 14, 10 + 13 + 15, 10 + 13 + 16, 10 + 13 + 17, 10 + 13 + 18, 10 + 13 + 19, 10 + 13 + 20, 10 + 13 + 21, 10 + 13 + 22, 10 + 13 + 23, 10 + 13 + 24, 10 + 13 + 25, 10 + 13 + 26, 10 + 13 + 27, 10 + 13 + 28, 10 + 13 + 29, 10 + 13 + 30, 10 + 13 + 31, 10 + 13 + 32, 10 + 13 + 33, 10 + 13 + 34, 10 + 13 + 35, 10 + 13 + 36, 10 + 13 + 37. |
| 14 | 10 + 14 + 15, 10 + 14 + 16, 10 + 14 + 17, 10 + 14 + 18, 10 + 14 + 19, 10 + 14 + 20, 10 + 14 + 21, 10 + 14 + 22, 10 + 14 + 23, 10 + 14 + 24, 10 + 14 + 25, 10 + 14 + 26, 10 + 14 + 27, 10 + 14 + 28, 10 + 14 + 29, 10 + 14 + 30, 10 + 14 + 31, 10 + 14 + 32, 10 + 14 + 33, 10 + 14 + 34, 10 + 14 + 35, 10 + 14 + 36, 10 + 14 + 37. |
| 15 | 10 + 15 + 16, 10 + 15 + 17, 10 + 15 + 18, 10 + 15 + 19, 10 + 15 + 20, 10 + 15 + 21, 10 + 15 + 22, 10 + 15 + 23, 10 + 15 + 24, 10 + 15 + 25, 10 + 15 + 26, 10 + 15 + 27, 10 + 15 + 28, 10 + 15 + 29, 10 + 15 + 30, 10 + 15 + 31, 10 + 15 + 32, 10 + 15 + 33, 10 + 15 + 34, 10 + 15 + 35, 10 + 15 + 36, 10 + 15 + 37. |
| 16 | 10 + 16 + 17, 10 + 16 + 18, 10 + 16 + 19, 10 + 16 + 20, 10 + 16 + 21, 10 + 16 + 22, 10 + 16 + 23, 10 + 16 + 24, 10 + 16 + 25, 10 + 16 + 26, 10 + 16 + 27, 10 + 16 + 28, 10 + 16 + 29, 10 + 16 + 30, 10 + 16 + 31, 10 + 16 + 32, 10 + 16 + 33, 10 + 16 + 34, 10 + 16 + 35, 10 + 16 + 36, 10 + 16 + 37. |
| 17 | 10 + 17 + 18, 10 + 17 + 19, 10 + 17 + 20, 10 + 17 + 21, 10 + 17 + 22, 10 + 17 + 23, 10 + 17 + 24, 10 + 17 + 25, 10 + 17 + 26, 10 + 17 + 27, 10 + 17 + 28, 10 + 17 + 29, 10 + 17 + 30, 10 + 17 + 31, 10 + 17 + 32, 10 + 17 + 33, 10 + 17 + 34, 10 + 17 + 35, 10 + 17 + 36, 10 + 17 + 37. |
| 18 | 10 + 18 + 19, 10 + 18 + 20, 10 + 18 + 21, 10 + 18 + 22, 10 + 18 + 23, 10 + 18 + 24, 10 + 18 + 25, 10 + 18 + 26, 10 + 18 + 27, 10 + 18 + 28, 10 + 18 + 29, 10 + 18 + 30, 10 + 18 + 31, 10 + 18 + 32, 10 + 18 + 33, 10 + 18 + 34, 10 + 18 + 35, 10 + 18 + 36, 10 + 18 + 37. |
| 19 | 10 + 19 + 20, 10 + 19 + 21, 10 + 19 + 22, 10 + 19 + 23, 10 + 19 + 24, 10 + 19 + 25, 10 + 19 + 26, 10 + 19 + 27, 10 + 19 + 28, 10 + 19 + 29, 10 + 19 + 30, 10 + 19 + 31, 10 + 19 + 32, 10 + 19 + 33, 10 + 19 + 34, 10 + 19 + 35, 10 + 19 + 36, 10 + 19 + 37. |
| 20 | 10 + 20 + 21, 10 + 20 + 22, 10 + 20 + 23, 10 + 20 + 24, 10 + 20 + 25, 10 + 20 + 26, 10 + 20 + 27, 10 + 20 + 28, 10 + 20 + 29, 10 + 20 + 30, 10 + 20 + 31, 10 + 20 + 32, 10 + 20 + 33, 10 + 20 + 34, 10 + 20 + 35, 10 + 20 + 36, 10 + 20 + 37. |
| 21 | 10 + 21 + 22, 10 + 21 + 23, 10 + 21 + 24, 10 + 21 + 25, 10 + 21 + 26, 10 + 21 + 27, 10 + 21 + 28, 10 + 21 + 29, 10 + 21 + 30, 10 + 21 + 31, 10 + 21 + 32, 10 + 21 + 33, 10 + 21 + 34, 10 + 21 + 35, 10 + 21 + 36, 10 + 21 + 37. |
| 22 | 10 + 22 + 23, 10 + 22 + 24, 10 + 22 + 25, 10 + 22 + 26, 10 + 22 + 27, 10 + 22 + 28, 10 + 22 + 29, 10 + 22 + 30, 10 + 22 + 31, 10 + 22 + 32, 10 + 22 + 33, 10 + 22 + 34, 10 + 22 + 35, 10 + 22 + 36, 10 + 22 + 37. |
| 23 | 10 + 23 + 24, 10 + 23 + 25, 10 + 23 + 26, 10 + 23 + 27, 10 + 23 + 28, 10 + 23 + 29, 10 + 23 + 30, 10 + 23 + 31, 10 + 23 + 32, 10 + 23 + 33, 10 + 23 + 34, 10 + 23 + 35, 10 + 23 + 36, 10 + 23 + 37. |
| 24 | 10 + 24 + 25, 10 + 24 + 26, 10 + 24 + 27, 10 + 24 + 28, 10 + 24 + 29, 10 + 24 + 30, 10 + 24 + 31, 10 + 24 + 32, 10 + 24 + 33, 10 + 24 + 34, 10 + 24 + 35, 10 + 24 + 36, 10 + 24 + 37. |
| 25 | 10 + 25 + 26, 10 + 25 + 27, 10 + 25 + 28, 10 + 25 + 29, 10 + 25 + 30, 10 + 25 + 31, 10 + 25 + 32, 10 + 25 + 33, 10 + 25 + 34, 10 + 25 + 35, 10 + 25 + 36, 10 + 25 + 37. |
| 26 | 10 + 26 + 27, 10 + 26 + 28, 10 + 26 + 29, 10 + 26 + 30, 10 + 26 + 31, 10 + 26 + 32, 10 + 26 + 33, 10 + 26 + 34, 10 + 26 + 35, 10 + 26 + 36, 10 + 26 + 37. |
| 27 | 10 + 27 + 28, 10 + 27 + 29, 10 + 27 + 30, 10 + 27 + 31, 10 + 27 + 32, 10 + 27 + 33, 10 + 27 + 34, 10 + 27 + 35, 10 + 27 + 36, 10 + 27 + 37. |
| 28 | 10 + 28 + 29, 10 + 28 + 30, 10 + 28 + 31, 10 + 28 + 32, 10 + 28 + 33, 10 + 28 + 34, 10 + 28 + 35, 10 + 28 + 36, 10 + 28 + 37. |
| 29 | 10 + 29 + 30, 10 + 29 + 31, 10 + 29 + 32, 10 + 29 + 33, 10 + 29 + 34, 10 + 29 + 35, 10 + 29 + 36, 10 + 29 + 37. |
| 30 | 10 + 30 + 31, 10 + 30 + 32, 10 + 30 + 33, 10 + 30 + 34, 10 + 30 + 35, 10 + 30 + 36, 10 + 30 + 37. |
| 31 | 10 + 31 + 32, 10 + 31 + 33, 10 + 31 + 34, 10 + 31 + 35, 10 + 31 + 36, 10 + 31 + 37. |
| 32 | 10 + 32 + 33, 10 + 32 + 34, 10 + 32 + 35, 10 + 32 + 36, 10 + 32 + 37. |
| 33 | 10 + 33 + 34, 10 + 33 + 35, 10 + 33 + 36, 10 + 33 + 37. |
| 34 | 10 + 34 + 35, 10 + 34 + 36, 10 + 34 + 37. |
| 35 | 10 + 35 + 36, 10 + 35 + 37. |
| 36 | 10 + 36 + 37. |

TABLE 11

Geraniol family of terpene formulations.
The numbers refer to the terpenes from Table 1. The
designation "family" is only for convenience in presentation,
as other tables also include formulations with geraniol.

Each disclosure of three terpenes represents a distinct formulation. In one embodiment, the formulation that is described by the indicated mixture of the three terpenes does not include any addition terpenes. In other embodiments, it does include additional terpenes.

| Sub-family | |
|---|---|
| 12 | 11 + 12 + 13, 11 + 12 + 14, 11 + 12 + 15, 11 + 12 + 16, 11 + 12 + 17, 11 + 12 + 18, 11 + 12 + 19, 11 + 12 + 20, 11 + 12 + 21, 11 + 12 + 22, 11 + 12 + 23, 11 + 12 + 24, 11 + 12 + 25, 11 + 12 + 26, 11 + 12 + 27, 11 + 12 + 28, 11 + 12 + 29, 11 + 12 + 30, 11 + 12 + 31, 11 + 12 + 32, 11 + 12 + 33, 11 + 12 + 34, 11 + 12 + 35, 11 + 12 + 36, 11 + 12 + 37. |
| 13 | 11 + 13 + 14, 11 + 13 + 15, 11 + 13 + 16, 11 + 13 + 17, 11 + 13 + 18, 11 + 13 + 19, 11 + 13 + 20, 11 + 13 + 21, 11 + 13 + 22, 11 + 13 + 23, 11 + 13 + 24, 11 + 13 + 25, 11 + 13 + 26, 11 + 13 + 27, 11 + 13 + 28, 11 + 13 + 29, 11 + 13 + 30, 11 + 13 + 31, 11 + 13 + 32, 11 + 13 + 33, 11 + 13 + 34, 11 + 13 + 35, 11 + 13 + 36, 11 + 13 + 37. |
| 14 | 11 + 14 + 15, 11 + 14 + 16, 11 + 14 + 17, 11 + 14 + 18, 11 + 14 + 19, 11 + 14 + 20, 11 + 14 + 21, 11 + 14 + 22, 11 + 14 + 23, 11 + 14 + 24, 11 + 14 + 25, 11 + 14 + 26, 11 + 14 + 27, 11 + 14 + 28, 11 + 14 + 29, 11 + 14 + 30, 11 + 14 + 31, 11 + 14 + 32, 11 + 14 + 33, 11 + 14 + 34, 11 + 14 + 35, 11 + 14 + 36, 11 + 14 + 37. |

TABLE 11-continued

Geraniol family of terpene formulations.
The numbers refer to the terpenes from Table 1. The
designation "family" is only for convenience in presentation,
as other tables also include formulations with geraniol.

| Sub-family | Each disclosure of three terpenes represents a distinct formulation. In one embodiment, the formulation that is described by the indicated mixture of the three terpenes does not include any addition terpenes. In other embodiments, it does include additional terpenes. |
|---|---|
| 15 | 11 + 15 + 16, 11 + 15 + 17, 11 + 15 + 18, 11 + 15 + 19, 11 + 15 + 20, 11 + 15 + 21, 11 + 15 + 22, 11 + 15 + 23, 11 + 15 + 24, 11 + 15 + 25, 11 + 15 + 26, 11 + 15 + 27, 11 + 15 + 28, 11 + 15 + 29, 11 + 15 + 30, 11 + 15 + 31, 11 + 15 + 32, 11 + 15 + 33, 11 + 15 + 34, 11 + 15 + 35, 11 + 15 + 36, 11 + 15 + 37. |
| 16 | 11 + 16 + 17, 11 + 16 + 18, 11 + 16 + 19, 11 + 16 + 20, 11 + 16 + 21, 11 + 16 + 22, 11 + 16 + 23, 11 + 16 + 24, 11 + 16 + 25, 11 + 16 + 26, 11 + 16 + 27, 11 + 16 + 28, 11 + 16 + 29, 11 + 16 + 30, 11 + 16 + 31, 11 + 16 + 32, 11 + 16 + 33, 11 + 16 + 34, 11 + 16 + 35, 11 + 16 + 36, 11 + 16 + 37. |
| 17 | 11 + 17 + 18, 11 + 17 + 19, 11 + 17 + 20, 11 + 17 + 21, 11 + 17 + 22, 11 + 17 + 23, 11 + 17 + 24, 11 + 17 + 25, 11 + 17 + 26, 11 + 17 + 27, 11 + 17 + 28, 11 + 17 + 29, 11 + 17 + 30, 11 + 17 + 31, 11 + 17 + 32, 11 + 17 + 33, 11 + 17 + 34, 11 + 17 + 35, 11 + 17 + 36, 11 + 17 + 37. |
| 18 | 11 + 18 + 19, 11 + 18 + 20, 11 + 18 + 21, 11 + 18 + 22, 11 + 18 + 23, 11 + 18 + 24, 11 + 18 + 25, 11 + 18 + 26, 11 + 18 + 27, 11 + 18 + 28, 11 + 18 + 29, 11 + 18 + 30, 11 + 18 + 31, 11 + 18 + 32, 11 + 18 + 33, 11 + 18 + 34, 11 + 18 + 35, 11 + 18 + 36, 11 + 18 + 37. |
| 19 | 11 + 19 + 20, 11 + 19 + 21, 11 + 19 + 22, 11 + 19 + 23, 11 + 19 + 24, 11 + 19 + 25, 11 + 19 + 26, 11 + 19 + 27, 11 + 19 + 28, 11 + 19 + 29, 11 + 19 + 30, 11 + 19 + 31, 11 + 19 + 32, 11 + 19 + 33, 11 + 19 + 34, 11 + 19 + 35, 11 + 19 + 36, 11 + 19 + 37. |
| 20 | 11 + 20 + 21, 11 + 20 + 22, 11 + 20 + 23, 11 + 20 + 24, 11 + 20 + 25, 11 + 20 + 26, 11 + 20 + 27, 11 + 20 + 28, 11 + 20 + 29, 11 + 20 + 30, 11 + 20 + 31, 11 + 20 + 32, 11 + 20 + 33, 11 + 20 + 34, 11 + 20 + 35, 11 + 20 + 36, 11 + 20 + 37. |
| 21 | 11 + 21 + 22, 11 + 21 + 23, 11 + 21 + 24, 11 + 21 + 25, 11 + 21 + 26, 11 + 21 + 27, 11 + 21 + 28, 11 + 21 + 29, 11 + 21 + 30, 11 + 21 + 31, 11 + 21 + 32, 11 + 21 + 33, 11 + 21 + 34, 11 + 21 + 35, 11 + 21 + 36, 11 + 21 + 37. |
| 22 | 11 + 22 + 23, 11 + 22 + 24, 11 + 22 + 25, 11 + 22 + 26, 11 + 22 + 27, 11 + 22 + 28, 11 + 22 + 29, 11 + 22 + 30, 11 + 22 + 31, 11 + 22 + 32, 11 + 22 + 33, 11 + 22 + 34, 11 + 22 + 35, 11 + 22 + 36, 11 + 22 + 37. |
| 23 | 11 + 23 + 24, 11 + 23 + 25, 11 + 23 + 26, 11 + 23 + 27, 11 + 23 + 28, 11 + 23 + 29, 11 + 23 + 30, 11 + 23 + 31, 11 + 23 + 32, 11 + 23 + 33, 11 + 23 + 34, 11 + 23 + 35, 11 + 23 + 36, 11 + 23 + 37. |
| 24 | 11 + 24 + 25, 11 + 24 + 26, 11 + 24 + 27, 11 + 24 + 28, 11 + 24 + 29, 11 + 24 + 30, 11 + 24 + 31, 11 + 24 + 32, 11 + 24 + 33, 11 + 24 + 34, 11 + 24 + 35, 11 + 24 + 36, 11 + 24 + 37. |
| 25 | 11 + 25 + 26, 11 + 25 + 27, 11 + 25 + 28, 11 + 25 + 29, 11 + 25 + 30, 11 + 25 + 31, 11 + 25 + 32, 11 + 25 + 33, 11 + 25 + 34, 11 + 25 + 35, 11 + 25 + 36, 11 + 25 + 37. |
| 26 | 11 + 26 + 27, 11 + 26 + 28, 11 + 26 + 29, 11 + 26 + 30, 11 + 26 + 31, 11 + 26 + 32, 11 + 26 + 33, 11 + 26 + 34, 11 + 26 + 35, 11 + 26 + 36, 11 + 26 + 37. |
| 27 | 11 + 27 + 28, 11 + 27 + 29, 11 + 27 + 30, 11 + 27 + 31, 11 + 27 + 32, 11 + 27 + 33, 11 + 27 + 34, 11 + 27 + 35, 11 + 27 + 36, 11 + 27 + 37. |
| 28 | 11 + 28 + 29, 11 + 28 + 30, 11 + 28 + 31, 11 + 28 + 32, 11 + 28 + 33, 11 + 28 + 34, 11 + 28 + 35, 11 + 28 + 36, 11 + 28 + 37. |
| 29 | 11 + 29 + 30, 11 + 29 + 31, 11 + 29 + 32, 11 + 29 + 33, 11 + 29 + 34, 11 + 29 + 35, 11 + 29 + 36, 11 + 29 + 37. |
| 30 | 11 + 30 + 31, 11 + 30 + 32, 11 + 30 + 33, 11 + 30 + 34, 11 + 30 + 35, 11 + 30 + 36, 11 + 30 + 37. |
| 31 | 11 + 31 + 32, 11 + 31 + 33, 11 + 31 + 34, 11 + 31 + 35, 11 + 31 + 36, 11 + 31 + 37. |
| 32 | 11 + 32 + 33, 11 + 32 + 34, 11 + 32 + 35, 11 + 32 + 36, 11 + 32 + 37. |
| 33 | 11 + 33 + 34, 11 + 33 + 35, 11 + 33 + 36, 11 + 33 + 37. |
| 34 | 11 + 34 + 35, 11 + 34 + 36, 11 + 34 + 37. |
| 35 | 11 + 35 + 36, 11 + 35 + 37. |
| 36 | 11 + 36 + 37. |

TABLE 12

Guaiol family of terpene formulations.
The numbers refer to the terpenes from Table 1. The
designation "family" is only for convenience in presentation,
as other tables also include formulations with guaiol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 13 | 12 + 13 + 14, 12 + 13 + 15, 12 + 13 + 16, 12 + 13 + 17, 12 + 13 + 18, 12 + 13 + 19, 12 + 13 + 20, 12 + 13 + 21, 12 + 13 + 22, 12 + 13 + 23, 12 + 13 + 24, 12 + 13 + 25, 12 + 13 + 26, 12 + 13 + 27, 12 + 13 + 28, 12 + 13 + 29, 12 + 13 + 30, 12 + 13 + 31, 12 + 13 + 32, 12 + 13 + 33, 12 + 13 + 34, 12 + 13 + 35, 12 + 13 + 36, 12 + 13 + 37. |
| 14 | 12 + 14 + 15, 12 + 14 + 16, 12 + 14 + 17, 12 + 14 + 18, 12 + 14 + 19, 12 + 14 + 20, 12 + 14 + 21, 12 + 14 + 22, 12 + 14 + 23, 12 + 14 + 24, 12 + 14 + 25, 12 + 14 + 26, 12 + 14 + 27, 12 + 14 + 28, 12 + 14 + 29, 12 + 14 + 30, 12 + 14 + 31, 12 + 14 + 32, 12 + 14 + 33, 12 + 14 + 34, 12 + 14 + 35, 12 + 14 + 36, 12 + 14 + 37. |
| 15 | 12 + 15 + 16, 12 + 15 + 17, 12 + 15 + 18, 12 + 15 + 19, 12 + 15 + 20, 12 + 15 + 21, 12 + 15 + 22, 12 + 15 + 23, 12 + 15 + 24, 12 + 15 + 25, 12 + 15 + 26, 12 + 15 + 27, 12 + 15 + 28, 12 + 15 + 29, 12 + 15 + 30, 12 + 15 + 31, 12 + 15 + 32, 12 + 15 + 33, 12 + 15 + 34, 12 + 15 + 35, 12 + 15 + 36, 12 + 15 + 37. |
| 16 | 12 + 16 + 17, 12 + 16 + 18, 12 + 16 + 19, 12 + 16 + 20, 12 + 16 + 21, 12 + 16 + 22, 12 + 16 + 23, 12 + 16 + 24, 12 + 16 + 25, 12 + 16 + 26, 12 + 16 + 27, 12 + 16 + 28, 12 + 16 + 29, 12 + 16 + 30, 12 + 16 + 31, 12 + 16 + 32, 12 + 16 + 33, 12 + 16 + 34, 12 + 16 + 35, 12 + 16 + 36, 12 + 16 + 37. |
| 17 | 12 + 17 + 18, 12 + 17 + 19, 12 + 17 + 20, 12 + 17 + 21, 12 + 17 + 22, 12 + 17 + 23, 12 + 17 + 24, 12 + 17 + 25, 12 + 17 + 26, 12 + 17 + 27, 12 + 17 + 28, 12 + 17 + 29, 12 + 17 + 30, 12 + 17 + 31, 12 + 17 + 32, 12 + 17 + 33, 12 + 17 + 34, 12 + 17 + 35, 12 + 17 + 36, 12 + 17 + 37. |
| 18 | 12 + 18 + 19, 12 + 18 + 20, 12 + 18 + 21, 12 + 18 + 22, 12 + 18 + 23, 12 + 18 + 24, 12 + 18 + 25, 12 + 18 + 26, 12 + 18 + 27, 12 + 18 + 28, 12 + 18 + 29, 12 + 18 + 30, 12 + 18 + 31, 12 + 18 + 32, 12 + 18 + 33, 12 + 18 + 34, 12 + 18 + 35, 12 + 18 + 36, 12 + 18 + 37. |
| 19 | 12 + 19 + 20, 12 + 19 + 21, 12 + 19 + 22, 12 + 19 + 23, 12 + 19 + 24, 12 + 19 + 25, 12 + 19 + 26, 12 + 19 + 27, 12 + 19 + 28, 12 + 19 + 29, 12 + 19 + 30, 12 + 19 + 31, 12 + 19 + 32, 12 + 19 + 33, 12 + 19 + 34, 12 + 19 + 35, 12 + 19 + 36, 12 + 19 + 37. |
| 20 | 12 + 20 + 21, 12 + 20 + 22, 12 + 20 + 23, 12 + 20 + 24, 12 + 20 + 25, 12 + 20 + 26, 12 + 20 + 27, 12 + 20 + 28, 12 + 20 + 29, 12 + 20 + 30, 12 + 20 + 31, 12 + 20 + 32, 12 + 20 + 33, 12 + 20 + 34, 12 + 20 + 35, 12 + 20 + 36, 12 + 20 + 37. |
| 21 | 12 + 21 + 22, 12 + 21 + 23, 12 + 21 + 24, 12 + 21 + 25, 12 + 21 + 26, 12 + 21 + 27, 12 + 21 + 28, 12 + 21 + 29, 12 + 21 + 30, 12 + 21 + 31, 12 + 21 + 32, 12 + 21 + 33, 12 + 21 + 34, 12 + 21 + 35, 12 + 21 + 36, 12 + 21 + 37. |

TABLE 12-continued

Guaiol family of terpene formulations.
The numbers refer to the terpenes from Table 1. The designation "family" is only for convenience in presentation, as other tables also include formulations with guaiol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 22 | 12 + 22 + 23, 12 + 22 + 24, 12 + 22 + 25, 12 + 22 + 26, 12 + 22 + 27, 12 + 22 + 28, 12 + 22 + 29, 12 + 22 + 30, 12 + 22 + 31, 12 + 22 + 32, 12 + 22 + 33, 12 + 22 + 34, 12 + 22 + 35, 12 + 22 + 36, 12 + 22 + 37. |
| 23 | 12 + 23 + 24, 12 + 23 + 25, 12 + 23 + 26, 12 + 23 + 27, 12 + 23 + 28, 12 + 23 + 29, 12 + 23 + 30, 12 + 23 + 31, 12 + 23 + 32, 12 + 23 + 33, 12 + 23 + 34, 12 + 23 + 35, 12 + 23 + 36, 12 + 23 + 37. |
| 24 | 12 + 24 + 25, 12 + 24 + 26, 12 + 24 + 27, 12 + 24 + 28, 12 + 24 + 29, 12 + 24 + 30, 12 + 24 + 31, 12 + 24 + 32, 12 + 24 + 33, 12 + 24 + 34, 12 + 24 + 35, 12 + 24 + 36, 12 + 24 + 37. |
| 25 | 12 + 25 + 26, 12 + 25 + 27, 12 + 25 + 28, 12 + 25 + 29, 12 + 25 + 30, 12 + 25 + 31, 12 + 25 + 32, 12 + 25 + 33, 12 + 25 + 34, 12 + 25 + 35, 12 + 25 + 36, 12 + 25 + 37. |
| 26 | 12 + 26 + 27, 12 + 26 + 28, 12 + 26 + 29, 12 + 26 + 30, 12 + 26 + 31, 12 + 26 + 32, 12 + 26 + 33, 12 + 26 + 34, 12 + 26 + 35, 12 + 26 + 36, 12 + 26 + 37. |
| 27 | 12 + 27 + 28, 12 + 27 + 29, 12 + 27 + 30, 12 + 27 + 31, 12 + 27 + 32, 12 + 27 + 33, 12 + 27 + 34, 12 + 27 + 35, 12 + 27 + 36, 12 + 27 + 37. |
| 28 | 12 + 28 + 29, 12 + 28 + 30, 12 + 28 + 31, 12 + 28 + 32, 12 + 28 + 33, 12 + 28 + 34, 12 + 28 + 35, 12 + 28 + 36, 12 + 28 + 37. |
| 29 | 12 + 29 + 30, 12 + 29 + 31, 12 + 29 + 32, 12 + 29 + 33, 12 + 29 + 34, 12 + 29 + 35, 12 + 29 + 36, 12 + 29 + 37. |
| 30 | 12 + 30 + 31, 12 + 30 + 32, 12 + 30 + 33, 12 + 30 + 34, 12 + 30 + 35, 12 + 30 + 36, 12 + 30 + 37. |
| 31 | 12 + 31 + 32, 12 + 31 + 33, 12 + 31 + 34, 12 + 31 + 35, 12 + 31 + 36, 12 + 31 + 37. |
| 32 | 12 + 32 + 33, 12 + 32 + 34, 12 + 32 + 35, 12 + 32 + 36, 12 + 32 + 37. |
| 33 | 12 + 33 + 34, 12 + 33 + 35, 12 + 33 + 36, 12 + 33 + 37. |
| 34 | 12 + 34 + 35, 12 + 34 + 36, 12 + 34 + 37. |
| 35 | 12 + 35 + 36, 12 + 35 + 37. |
| 36 | 12 + 36 + 37. |

TABLE 13

Alpha-humulene family of terpene formulations.
The numbers refer to the terpenes from Table 1.
The designation "family" is only for convenience in presentation, as other tables also include formulations with alpha-humulene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 14 | 13 + 14 + 15, 13 + 14 + 16, 13 + 14 + 17, 13 + 14 + 18, 13 + 14 + 19, 13 + 14 + 20, 13 + 14 + 21, 13 + 14 + 22, 13 + 14 + 23, 13 + 14 + 24, 13 + 14 + 25, 13 + 14 + 26, 13 + 14 + 27, 13 + 14 + 28, 13 + 14 + 29, 13 + 14 + 30, 13 + 14 + 31, 13 + 14 + 32, 13 + 14 + 33, 13 + 14 + 34, 13 + 14 + 35, 13 + 14 + 36, 13 + 14 + 37. |
| 15 | 13 + 15 + 16, 13 + 15 + 17, 13 + 15 + 18, 13 + 15 + 19, 13 + 15 + 20, 13 + 15 + 21, 13 + 15 + 22, 13 + 15 + 23, 13 + 15 + 24, 13 + 15 + 25, 13 + 15 + 26, 13 + 15 + 27, 13 + 15 + 28, 13 + 15 + 29, 13 + 15 + 30, 13 + 15 + 31, 13 + 15 + 32, 13 + 15 + 33, 13 + 15 + 34, 13 + 15 + 35, 13 + 15 + 36, 13 + 15 + 37. |
| 16 | 13 + 16 + 17, 13 + 16 + 18, 13 + 16 + 19, 13 + 16 + 20, 13 + 16 + 21, 13 + 16 + 22, 13 + 16 + 23, 13 + 16 + 24, 13 + 16 + 25, 13 + 16 + 26, 13 + 16 + 27, 13 + 16 + 28, 13 + 16 + 29, 13 + 16 + 30, 13 + 16 + 31, 13 + 16 + 32, 13 + 16 + 33, 13 + 16 + 34, 13 + 16 + 35, 13 + 16 + 36, 13 + 16 + 37. |
| 17 | 13 + 17 + 18, 13 + 17 + 19, 13 + 17 + 20, 13 + 17 + 21, 13 + 17 + 22, 13 + 17 + 23, 13 + 17 + 24, 13 + 17 + 25, 13 + 17 + 26, 13 + 17 + 27, 13 + 17 + 28, 13 + 17 + 29, 13 + 17 + 30, 13 + 17 + 31, 13 + 17 + 32, 13 + 17 + 33, 13 + 17 + 34, 13 + 17 + 35, 13 + 17 + 36, 13 + 17 + 37. |
| 18 | 13 + 18 + 19, 13 + 18 + 20, 13 + 18 + 21, 13 + 18 + 22, 13 + 18 + 23, 13 + 18 + 24, 13 + 18 + 25, 13 + 18 + 26, 13 + 18 + 27, 13 + 18 + 28, 13 + 18 + 29, 13 + 18 + 30, 13 + 18 + 31, 13 + 18 + 32, 13 + 18 + 33, 13 + 18 + 34, 13 + 18 + 35, 13 + 18 + 36, 13 + 18 + 37. |
| 19 | 13 + 19 + 20, 13 + 19 + 21, 13 + 19 + 22, 13 + 19 + 23, 13 + 19 + 24, 13 + 19 + 25, 13 + 19 + 26, 13 + 19 + 27, 13 + 19 + 28, 13 + 19 + 29, 13 + 19 + 30, 13 + 19 + 31, 13 + 19 + 32, 13 + 19 + 33, 13 + 19 + 34, 13 + 19 + 35, 13 + 19 + 36, 13 + 19 + 37. |
| 20 | 13 + 20 + 21, 13 + 20 + 22, 13 + 20 + 23, 13 + 20 + 24, 13 + 20 + 25, 13 + 20 + 26, 13 + 20 + 27, 13 + 20 + 28, 13 + 20 + 29, 13 + 20 + 30, 13 + 20 + 31, 13 + 20 + 32, 13 + 20 + 33, 13 + 20 + 34, 13 + 20 + 35, 13 + 20 + 36, 13 + 20 + 37. |
| 21 | 13 + 21 + 22, 13 + 21 + 23, 13 + 21 + 24, 13 + 21 + 25, 13 + 21 + 26, 13 + 21 + 27, 13 + 21 + 28, 13 + 21 + 29, 13 + 21 + 30, 13 + 21 + 31, 13 + 21 + 32, 13 + 21 + 33, 13 + 21 + 34, 13 + 21 + 35, 13 + 21 + 36, 13 + 21 + 37. |
| 22 | 13 + 22 + 23, 13 + 22 + 24, 13 + 22 + 25, 13 + 22 + 26, 13 + 22 + 27, 13 + 22 + 28, 13 + 22 + 29, 13 + 22 + 30, 13 + 22 + 31, 13 + 22 + 32, 13 + 22 + 33, 13 + 22 + 34, 13 + 22 + 35, 13 + 22 + 36, 13 + 22 + 37. |
| 23 | 13 + 23 + 24, 13 + 23 + 25, 13 + 23 + 26, 13 + 23 + 27, 13 + 23 + 28, 13 + 23 + 29, 13 + 23 + 30, 13 + 23 + 31, 13 + 23 + 32, 13 + 23 + 33, 13 + 23 + 34, 13 + 23 + 35, 13 + 23 + 36, 13 + 23 + 37. |
| 24 | 13 + 24 + 25, 13 + 24 + 26, 13 + 24 + 27, 13 + 24 + 28, 13 + 24 + 29, 13 + 24 + 30, 13 + 24 + 31, 13 + 24 + 32, 13 + 24 + 33, 13 + 24 + 34, 13 + 24 + 35, 13 + 24 + 36, 13 + 24 + 37. |
| 25 | 13 + 25 + 26, 13 + 25 + 27, 13 + 25 + 28, 13 + 25 + 29, 13 + 25 + 30, 13 + 25 + 31, 13 + 25 + 32, 13 + 25 + 33, 13 + 25 + 34, 13 + 25 + 35, 13 + 25 + 36, 13 + 25 + 37. |
| 26 | 13 + 26 + 27, 13 + 26 + 28, 13 + 26 + 29, 13 + 26 + 30, 13 + 26 + 31, 13 + 26 + 32, 13 + 26 + 33, 13 + 26 + 34, 13 + 26 + 35, 13 + 26 + 36, 13 + 26 + 37. |
| 27 | 13 + 27 + 28, 13 + 27 + 29, 13 + 27 + 30, 13 + 27 + 31, 13 + 27 + 32, 13 + 27 + 33, 13 + 27 + 34, 13 + 27 + 35, 13 + 27 + 36, 13 + 27 + 37. |
| 28 | 13 + 28 + 29, 13 + 28 + 30, 13 + 28 + 31, 13 + 28 + 32, 13 + 28 + 33, 13 + 28 + 34, 13 + 28 + 35, 13 + 28 + 36, 13 + 28 + 37. |
| 29 | 13 + 29 + 30, 13 + 29 + 31, 13 + 29 + 32, 13 + 29 + 33, 13 + 29 + 34, 13 + 29 + 35, 13 + 29 + 36, 13 + 29 + 37. |
| 30 | 13 + 30 + 31, 13 + 30 + 32, 13 + 30 + 33, 13 + 30 + 34, 13 + 30 + 35, 13 + 30 + 36, 13 + 30 + 37. |
| 31 | 13 + 31 + 32, 13 + 31 + 33, 13 + 31 + 34, 13 + 31 + 35, 13 + 31 + 36, 13 + 31 + 37. |
| 32 | 13 + 32 + 33, 13 + 32 + 34, 13 + 32 + 35, 13 + 32 + 36, 13 + 32 + 37. |
| 33 | 13 + 33 + 34, 13 + 33 + 35, 13 + 33 + 36, 13 + 33 + 37. |
| 34 | 13 + 34 + 35, 13 + 34 + 36, 13 + 34 + 37. |
| 35 | 13 + 35 + 36, 13 + 35 + 37. |
| 36 | 13 + 36 + 37. |

TABLE 14

Isoborneol family of terpene formulations.
The numbers refer to the terpenes from Table 1.
The designation "family" is only for convenience in presentation,
as other tables also include formulations with isoborneol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 15 | 14 + 15 + 16, 14 + 15 + 17, 14 + 15 + 18, 14 + 15 + 19, 14 + 15 + 20, 14 + 15 + 21, 14 + 15 + 22, 14 + 15 + 23, 14 + 15 + 24, 14 + 15 + 25, 14 + 15 + 26, 14 + 15 + 27, 14 + 15 + 28, 14 + 15 + 29, 14 + 15 + 30, 14 + 15 + 31, 14 + 15 + 32, 14 + 15 + 33, 14 + 15 + 34, 14 + 15 + 35, 14 + 15 + 36, 14 + 15 + 37. |
| 16 | 14 + 16 + 17, 14 + 16 + 18, 14 + 16 + 19, 14 + 16 + 20, 14 + 16 + 21, 14 + 16 + 22, 14 + 16 + 23, 14 + 16 + 24, 14 + 16 + 25, 14 + 16 + 26, 14 + 16 + 27, 14 + 16 + 28, 14 + 16 + 29, 14 + 16 + 30, 14 + 16 + 31, 14 + 16 + 32, 14 + 16 + 33, 14 + 16 + 34, 14 + 16 + 35, 14 + 16 + 36, 14 + 16 + 37. |
| 17 | 14 + 17 + 18, 14 + 17 + 19, 14 + 17 + 20, 14 + 17 + 21, 14 + 17 + 22, 14 + 17 + 23, 14 + 17 + 24, 14 + 17 + 25, 14 + 17 + 26, 14 + 17 + 27, 14 + 17 + 28, 14 + 17 + 29, 14 + 17 + 30, 14 + 17 + 31, 14 + 17 + 32, 14 + 17 + 33, 14 + 17 + 34, 14 + 17 + 35, 14 + 17 + 36, 14 + 17 + 37. |
| 18 | 14 + 18 + 19, 14 + 18 + 20, 14 + 18 + 21, 14 + 18 + 22, 14 + 18 + 23, 14 + 18 + 24, 14 + 18 + 25, 14 + 18 + 26, 14 + 18 + 27, 14 + 18 + 28, 14 + 18 + 29, 14 + 18 + 30, 14 + 18 + 31, 14 + 18 + 32, 14 + 18 + 33, 14 + 18 + 34, 14 + 18 + 35, 14 + 18 + 36, 14 + 18 + 37. |
| 19 | 14 + 19 + 20, 14 + 19 + 21, 14 + 19 + 22, 14 + 19 + 23, 14 + 19 + 24, 14 + 19 + 25, 14 + 19 + 26, 14 + 19 + 27, 14 + 19 + 28, 14 + 19 + 29, 14 + 19 + 30, 14 + 19 + 31, 14 + 19 + 32, 14 + 19 + 33, 14 + 19 + 34, 14 + 19 + 35, 14 + 19 + 36, 14 + 19 + 37. |
| 20 | 14 + 20 + 21, 14 + 20 + 22, 14 + 20 + 23, 14 + 20 + 24, 14 + 20 + 25, 14 + 20 + 26, 14 + 20 + 27, 14 + 20 + 28, 14 + 20 + 29, 14 + 20 + 30, 14 + 20 + 31, 14 + 20 + 32, 14 + 20 + 33, 14 + 20 + 34, 14 + 20 + 35, 14 + 20 + 36, 14 + 20 + 37. |
| 21 | 14 + 21 + 22, 14 + 21 + 23, 14 + 21 + 24, 14 + 21 + 25, 14 + 21 + 26, 14 + 21 + 27, 14 + 21 + 28, 14 + 21 + 29, 14 + 21 + 30, 14 + 21 + 31, 14 + 21 + 32, 14 + 21 + 33, 14 + 21 + 34, 14 + 21 + 35, 14 + 21 + 36, 14 + 21 + 37. |
| 22 | 14 + 22 + 23, 14 + 22 + 24, 14 + 22 + 25, 14 + 22 + 26, 14 + 22 + 27, 14 + 22 + 28, 14 + 22 + 29, 14 + 22 + 30, 14 + 22 + 31, 14 + 22 + 32, 14 + 22 + 33, 14 + 22 + 34, 14 + 22 + 35, 14 + 22 + 36, 14 + 22 + 37. |
| 23 | 14 + 23 + 24, 14 + 23 + 25, 14 + 23 + 26, 14 + 23 + 27, 14 + 23 + 28, 14 + 23 + 29, 14 + 23 + 30, 14 + 23 + 31, 14 + 23 + 32, 14 + 23 + 33, 14 + 23 + 34, 14 + 23 + 35, 14 + 23 + 36, 14 + 23 + 37. |
| 24 | 14 + 24 + 25, 14 + 24 + 26, 14 + 24 + 27, 14 + 24 + 28, 14 + 24 + 29, 14 + 24 + 30, 14 + 24 + 31, 14 + 24 + 32, 14 + 24 + 33, 14 + 24 + 34, 14 + 24 + 35, 14 + 24 + 36, 14 + 24 + 37. |
| 25 | 14 + 25 + 26, 14 + 25 + 27, 14 + 25 + 28, 14 + 25 + 29, 14 + 25 + 30, 14 + 25 + 31, 14 + 25 + 32, 14 + 25 + 33, 14 + 25 + 34, 14 + 25 + 35, 14 + 25 + 36, 14 + 25 + 37. |
| 26 | 14 + 26 + 27, 14 + 26 + 28, 14 + 26 + 29, 14 + 26 + 30, 14 + 26 + 31, 14 + 26 + 32, 14 + 26 + 33, 14 + 26 + 34, 14 + 26 + 35, 14 + 26 + 36, 14 + 26 + 37. |
| 27 | 14 + 27 + 28, 14 + 27 + 29, 14 + 27 + 30, 14 + 27 + 31, 14 + 27 + 32, 14 + 27 + 33, 14 + 27 + 34, 14 + 27 + 35, 14 + 27 + 36, 14 + 27 + 37. |
| 28 | 14 + 28 + 29, 14 + 28 + 30, 14 + 28 + 31, 14 + 28 + 32, 14 + 28 + 33, 14 + 28 + 34, 14 + 28 + 35, 14 + 28 + 36, 14 + 28 + 37. |
| 29 | 14 + 29 + 30, 14 + 29 + 31, 14 + 29 + 32, 14 + 29 + 33, 14 + 29 + 34, 14 + 29 + 35, 14 + 29 + 36, 14 + 29 + 37. |
| 30 | 14 + 30 + 31, 14 + 30 + 32, 14 + 30 + 33, 14 + 30 + 34, 14 + 30 + 35, 14 + 30 + 36, 14 + 30 + 37. |
| 31 | 14 + 31 + 32, 14 + 31 + 33, 14 + 31 + 34, 14 + 31 + 35, 14 + 31 + 36, 14 + 31 + 37. |
| 32 | 14 + 32 + 33, 14 + 32 + 34, 14 + 32 + 35, 14 + 32 + 36, 14 + 32 + 37. |
| 33 | 14 + 33 + 34, 14 + 33 + 35, 14 + 33 + 36, 14 + 33 + 37. |
| 34 | 14 + 34 + 35, 14 + 34 + 36, 14 + 34 + 37. |
| 35 | 14 + 35 + 36, 14 + 35 + 37. |
| 36 | 14 + 36 + 37. |

TABLE 15

Limonene family of terpene formulations.
The numbers refer to the terpenes from Table 1.
The designation "family" is only for convenience in presentation,
as other tables also include formulations with limonene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 16 | 15 + 16 + 17, 15 + 16 + 18, 15 + 16 + 19, 15 + 16 + 20, 15 + 16 + 21, 15 + 16 + 22, 15 + 16 + 23, 15 + 16 + 24, 15 + 16 + 25, 15 + 16 + 26, 15 + 16 + 27, 15 + 16 + 28, 15 + 16 + 29, 15 + 16 + 30, 15 + 16 + 31, 15 + 16 + 32, 15 + 16 + 33, 15 + 16 + 34, 15 + 16 + 35, 15 + 16 + 36, 15 + 16 + 37. |
| 17 | 15 + 17 + 18, 15 + 17 + 19, 15 + 17 + 20, 15 + 17 + 21, 15 + 17 + 22, 15 + 17 + 23, 15 + 17 + 24, 15 + 17 + 25, 15 + 17 + 26, 15 + 17 + 27, 15 + 17 + 28, 15 + 17 + 29, 15 + 17 + 30, 15 + 17 + 31, 15 + 17 + 32, 15 + 17 + 33, 15 + 17 + 34, 15 + 17 + 35, 15 + 17 + 36, 15 + 17 + 37. |
| 18 | 15 + 18 + 19, 15 + 18 + 20, 15 + 18 + 21, 15 + 18 + 22, 15 + 18 + 23, 15 + 18 + 24, 15 + 18 + 25, 15 + 18 + 26, 15 + 18 + 27, 15 + 18 + 28, 15 + 18 + 29, 15 + 18 + 30, 15 + 18 + 31, 15 + 18 + 32, 15 + 18 + 33, 15 + 18 + 34, 15 + 18 + 35, 15 + 18 + 36, 15 + 18 + 37. |
| 19 | 15 + 19 + 20, 15 + 19 + 21, 15 + 19 + 22, 15 + 19 + 23, 15 + 19 + 24, 15 + 19 + 25, 15 + 19 + 26, 15 + 19 + 27, 15 + 19 + 28, 15 + 19 + 29, 15 + 19 + 30, 15 + 19 + 31, 15 + 19 + 32, 15 + 19 + 33, 15 + 19 + 34, 15 + 19 + 35, 15 + 19 + 36, 15 + 19 + 37. |
| 20 | 15 + 20 + 21, 15 + 20 + 22, 15 + 20 + 23, 15 + 20 + 24, 15 + 20 + 25, 15 + 20 + 26, 15 + 20 + 27, 15 + 20 + 28, 15 + 20 + 29, 15 + 20 + 30, 15 + 20 + 31, 15 + 20 + 32, 15 + 20 + 33, 15 + 20 + 34, 15 + 20 + 35, 15 + 20 + 36, 15 + 20 + 37. |
| 21 | 15 + 21 + 22, 15 + 21 + 23, 15 + 21 + 24, 15 + 21 + 25, 15 + 21 + 26, 15 + 21 + 27, 15 + 21 + 28, 15 + 21 + 29, 15 + 21 + 30, 15 + 21 + 31, 15 + 21 + 32, 15 + 21 + 33, 15 + 21 + 34, 15 + 21 + 35, 15 + 21 + 36, 15 + 21 + 37. |
| 22 | 15 + 22 + 23, 15 + 22 + 24, 15 + 22 + 25, 15 + 22 + 26, 15 + 22 + 27, 15 + 22 + 28, 15 + 22 + 29, 15 + 22 + 30, 15 + 22 + 31, 15 + 22 + 32, 15 + 22 + 33, 15 + 22 + 34, 15 + 22 + 35, 15 + 22 + 36, 15 + 22 + 37. |
| 23 | 15 + 23 + 24, 15 + 23 + 25, 15 + 23 + 26, 15 + 23 + 27, 15 + 23 + 28, 15 + 23 + 29, 15 + 23 + 30, 15 + 23 + 31, 15 + 23 + 32, 15 + 23 + 33, 15 + 23 + 34, 15 + 23 + 35, 15 + 23 + 36, 15 + 23 + 37. |
| 24 | 15 + 24 + 25, 15 + 24 + 26, 15 + 24 + 27, 15 + 24 + 28, 15 + 24 + 29, 15 + 24 + 30, 15 + 24 + 31, 15 + 24 + 32, 15 + 24 + 33, 15 + 24 + 34, 15 + 24 + 35, 15 + 24 + 36, 15 + 24 + 37. |
| 25 | 15 + 25 + 26, 15 + 25 + 27, 15 + 25 + 28, 15 + 25 + 29, 15 + 25 + 30, 15 + 25 + 31, 15 + 25 + 32, 15 + 25 + 33, 15 + 25 + 34, 15 + 25 + 35, 15 + 25 + 36, 15 + 25 + 37. |
| 26 | 15 + 26 + 27, 15 + 26 + 28, 15 + 26 + 29, 15 + 26 + 30, 15 + 26 + 31, 15 + 26 + 32, 15 + 26 + 33, 15 + 26 + 34, 15 + 26 + 35, 15 + 26 + 36, 15 + 26 + 37. |

TABLE 15-continued

Limonene family of terpene formulations.
The numbers refer to the terpenes from Table 1.
The designation "family" is only for convenience in presentation,
as other tables also include formulations with limonene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 27 | 15 + 27 + 28, 15 + 27 + 29, 15 + 27 + 30, 15 + 27 + 31, 15 + 27 + 32, 15 + 27 + 33, 15 + 27 + 34, 15 + 27 + 35, 15 + 27 + 36, 15 + 27 + 37. |
| 28 | 15 + 28 + 29, 15 + 28 + 30, 15 + 28 + 31, 15 + 28 + 32, 15 + 28 + 33, 15 + 28 + 34, 15 + 28 + 35, 15 + 28 + 36, 15 + 28 + 37. |
| 29 | 15 + 29 + 30, 15 + 29 + 31, 15 + 29 + 32, 15 + 29 + 33, 15 + 29 + 34, 15 + 29 + 35, 15 + 29 + 36, 15 + 29 + 37. |
| 30 | 15 + 30 + 31, 15 + 30 + 32, 15 + 30 + 33, 15 + 30 + 34, 15 + 30 + 35, 15 + 30 + 36, 15 + 30 + 37. |
| 31 | 15 + 31 + 32, 15 + 31 + 33, 15 + 31 + 34, 15 + 31 + 35, 15 + 31 + 36, 15 + 31 + 37. |
| 32 | 15 + 32 + 33, 15 + 32 + 34, 15 + 32 + 35, 15 + 32 + 36, 15 + 32 + 37. |
| 33 | 15 + 33 + 34, 15 + 33 + 35, 15 + 33 + 36, 15 + 33 + 37. |
| 34 | 15 + 34 + 35, 15 + 34 + 36, 15 + 34 + 37. |
| 35 | 15 + 35 + 36, 15 + 35 + 37. |
| 36 | 15 + 36 + 37. |

TABLE 16

Linalool family of terpene formulations.
The numbers refer to the terpenes from Table 1.
The designation "family" is only for convenience in presentation,
as other tables also include formulations with linalool.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 17 | 16 + 17 + 18, 16 + 17 + 19, 16 + 17 + 20, 16 + 17 + 21, 16 + 17 + 22, 16 + 17 + 23, 16 + 17 + 24, 16 + 17 + 25, 16 + 17 + 26, 16 + 17 + 27, 16 + 17 + 28, 16 + 17 + 29, 16 + 17 + 30, 16 + 17 + 31, 16 + 17 + 32, 16 + 17 + 33, 16 + 17 + 34, 16 + 17 + 35, 16 + 17 + 36, 16 + 17 + 37. |
| 18 | 16 + 18 + 19, 16 + 18 + 20, 16 + 18 + 21, 16 + 18 + 22, 16 + 18 + 23, 16 + 18 + 24, 16 + 18 + 25, 16 + 18 + 26, 16 + 18 + 27, 16 + 18 + 28, 16 + 18 + 29, 16 + 18 + 30, 16 + 18 + 31, 16 + 18 + 32, 16 + 18 + 33, 16 + 18 + 34, 16 + 18 + 35, 16 + 18 + 36, 16 + 18 + 37. |
| 19 | 16 + 19 + 20, 16 + 19 + 21, 16 + 19 + 22, 16 + 19 + 23, 16 + 19 + 24, 16 + 19 + 25, 16 + 19 + 26, 16 + 19 + 27, 16 + 19 + 28, 16 + 19 + 29, 16 + 19 + 30, 16 + 19 + 31, 16 + 19 + 32, 16 + 19 + 33, 16 + 19 + 34, 16 + 19 + 35, 16 + 19 + 36, 16 + 19 + 37. |
| 20 | 16 + 20 + 21, 16 + 20 + 22, 16 + 20 + 23, 16 + 20 + 24, 16 + 20 + 25, 16 + 20 + 26, 16 + 20 + 27, 16 + 20 + 28, 16 + 20 + 29, 16 + 20 + 30, 16 + 20 + 31, 16 + 20 + 32, 16 + 20 + 33, 16 + 20 + 34, 16 + 20 + 35, 16 + 20 + 36, 16 + 20 + 37. |
| 21 | 16 + 21 + 22, 16 + 21 + 23, 16 + 21 + 24, 16 + 21 + 25, 16 + 21 + 26, 16 + 21 + 27, 16 + 21 + 28, 16 + 21 + 29, 16 + 21 + 30, 16 + 21 + 31, 16 + 21 + 32, 16 + 21 + 33, 16 + 21 + 34, 16 + 21 + 35, 16 + 21 + 36, 16 + 21 + 37. |
| 22 | 16 + 22 + 23, 16 + 22 + 24, 16 + 22 + 25, 16 + 22 + 26, 16 + 22 + 27, 16 + 22 + 28, 16 + 22 + 29, 16 + 22 + 30, 16 + 22 + 31, 16 + 22 + 32, 16 + 22 + 33, 16 + 22 + 34, 16 + 22 + 35, 16 + 22 + 36, 16 + 22 + 37. |
| 23 | 16 + 23 + 24, 16 + 23 + 25, 16 + 23 + 26, 16 + 23 + 27, 16 + 23 + 28, 16 + 23 + 29, 16 + 23 + 30, 16 + 23 + 31, 16 + 23 + 32, 16 + 23 + 33, 16 + 23 + 34, 16 + 23 + 35, 16 + 23 + 36, 16 + 23 + 37. |
| 24 | 16 + 24 + 25, 16 + 24 + 26, 16 + 24 + 27, 16 + 24 + 28, 16 + 24 + 29, 16 + 24 + 30, 16 + 24 + 31, 16 + 24 + 32, 16 + 24 + 33, 16 + 24 + 34, 16 + 24 + 35, 16 + 24 + 36, 16 + 24 + 37. |
| 25 | 16 + 25 + 26, 16 + 25 + 27, 16 + 25 + 28, 16 + 25 + 29, 16 + 25 + 30, 16 + 25 + 31, 16 + 25 + 32, 16 + 25 + 33, 16 + 25 + 34, 16 + 25 + 35, 16 + 25 + 36, 16 + 25 + 37. |
| 26 | 16 + 26 + 27, 16 + 26 + 28, 16 + 26 + 29, 16 + 26 + 30, 16 + 26 + 31, 16 + 26 + 32, 16 + 26 + 33, 16 + 26 + 34, 16 + 26 + 35, 16 + 26 + 36, 16 + 26 + 37. |
| 27 | 16 + 27 + 28, 16 + 27 + 29, 16 + 27 + 30, 16 + 27 + 31, 16 + 27 + 32, 16 + 27 + 33, 16 + 27 + 34, 16 + 27 + 35, 16 + 27 + 36, 16 + 27 + 37. |
| 28 | 16 + 28 + 29, 16 + 28 + 30, 16 + 28 + 31, 16 + 28 + 32, 16 + 28 + 33, 16 + 28 + 34, 16 + 28 + 35, 16 + 28 + 36, 16 + 28 + 37. |
| 29 | 16 + 29 + 30, 16 + 29 + 31, 16 + 29 + 32, 16 + 29 + 33, 16 + 29 + 34, 16 + 29 + 35, 16 + 29 + 36, 16 + 29 + 37. |
| 30 | 16 + 30 + 31, 16 + 30 + 32, 16 + 30 + 33, 16 + 30 + 34, 16 + 30 + 35, 16 + 30 + 36, 16 + 30 + 37. |
| 31 | 16 + 31 + 32, 16 + 31 + 33, 16 + 31 + 34, 16 + 31 + 35, 16 + 31 + 36, 16 + 31 + 37. |
| 32 | 16 + 32 + 33, 16 + 32 + 34, 16 + 32 + 35, 16 + 32 + 36, 16 + 32 + 37. |
| 33 | 16 + 33 + 34, 16 + 33 + 35, 16 + 33 + 36, 16 + 33 + 37. |
| 34 | 16 + 34 + 35, 16 + 34 + 36, 16 + 34 + 37. |
| 35 | 16 + 35 + 36, 16 + 35 + 37. |
| 36 | 16 + 36 + 37. |

TABLE 17

Menthol family of terpene formulations.
The numbers refer to the terpenes from Table 1.
The designation "family" is only for convenience in presentation,
as other tables also include formulations with menthol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 18 | 17 + 18 + 19, 17 + 18 + 20, 17 + 18 + 21, 17 + 18 + 22, 17 + 18 + 23, 17 + 18 + 24, 17 + 18 + 25, 17 + 18 + 26, 17 + 18 + 27, 17 + 18 + 28, 17 + 18 + 29, 17 + 18 + 30, 17 + 18 + 31, 17 + 18 + 32, 17 + 18 + 33, 17 + 18 + 34, 17 + 18 + 35, 17 + 18 + 36, 17 + 18 + 37. |
| 19 | 17 + 19 + 20, 17 + 19 + 21, 17 + 19 + 22, 17 + 19 + 23, 17 + 19 + 24, 17 + 19 + 25, 17 + 19 + 26, 17 + 19 + 27, 17 + 19 + 28, 17 + 19 + 29, 17 + 19 + 30, 17 + 19 + 31, 17 + 19 + 32, 17 + 19 + 33, 17 + 19 + 34, 17 + 19 + 35, 17 + 19 + 36, 17 + 19 + 37. |
| 20 | 17 + 20 + 21, 17 + 20 + 22, 17 + 20 + 23, 17 + 20 + 24, 17 + 20 + 25, 17 + 20 + 26, 17 + 20 + 27, 17 + 20 + 28, 17 + 20 + 29, 17 + 20 + 30, 17 + 20 + 31, 17 + 20 + 32, 17 + 20 + 33, 17 + 20 + 34, 17 + 20 + 35, 17 + 20 + 36, 17 + 20 + 37. |
| 21 | 17 + 21 + 22, 17 + 21 + 23, 17 + 21 + 24, 17 + 21 + 25, 17 + 21 + 26, 17 + 21 + 27, 17 + 21 + 28, 17 + 21 + 29, 17 + 21 + 30, 17 + 21 + 31, 17 + 21 + 32, 17 + 21 + 33, 17 + 21 + 34, 17 + 21 + 35, 17 + 21 + 36, 17 + 21 + 37. |
| 22 | 17 + 22 + 23, 17 + 22 + 24, 17 + 22 + 25, 17 + 22 + 26, 17 + 22 + 27, 17 + 22 + 28, 17 + 22 + 29, 17 + 22 + 30, 17 + 22 + 31, 17 + 22 + 32, 17 + 22 + 33, 17 + 22 + 34, 17 + 22 + 35, 17 + 22 + 36, 17 + 22 + 37. |

TABLE 17-continued

Menthol family of terpene formulations.
The numbers refer to the terpenes from Table 1.
The designation "family" is only for convenience in presentation,
as other tables also include formulations with menthol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 23 | 17 + 23 + 24, 17 + 23 + 25, 17 + 23 + 26, 17 + 23 + 27, 17 + 23 + 28, 17 + 23 + 29, 17 + 23 + 30, 17 + 23 + 31, 17 + 23 + 32, 17 + 23 + 33, 17 + 23 + 34, 17 + 23 + 35, 17 + 23 + 36, 17 + 23 + 37. |
| 24 | 17 + 24 + 25, 17 + 24 + 26, 17 + 24 + 27, 17 + 24 + 28, 17 + 24 + 29, 17 + 24 + 30, 17 + 24 + 31, 17 + 24 + 32, 17 + 24 + 33, 17 + 24 + 34, 17 + 24 + 35, 17 + 24 + 36, 17 + 24 + 37. |
| 25 | 17 + 25 + 26, 17 + 25 + 27, 17 + 25 + 28, 17 + 25 + 29, 17 + 25 + 30, 17 + 25 + 31, 17 + 25 + 32, 17 + 25 + 33, 17 + 25 + 34, 17 + 25 + 35, 17 + 25 + 36, 17 + 25 + 37. |
| 26 | 17 + 26 + 27, 17 + 26 + 28, 17 + 26 + 29, 17 + 26 + 30, 17 + 26 + 31, 17 + 26 + 32, 17 + 26 + 33, 17 + 26 + 34, 17 + 26 + 35, 17 + 26 + 36, 17 + 26 + 37. |
| 27 | 17 + 27 + 28, 17 + 27 + 29, 17 + 27 + 30, 17 + 27 + 31, 17 + 27 + 32, 17 + 27 + 33, 17 + 27 + 34, 17 + 27 + 35, 17 + 27 + 36, 17 + 27 + 37. |
| 28 | 17 + 28 + 29, 17 + 28 + 30, 17 + 28 + 31, 17 + 28 + 32, 17 + 28 + 33, 17 + 28 + 34, 17 + 28 + 35, 17 + 28 + 36, 17 + 28 + 37. |
| 29 | 17 + 29 + 30, 17 + 29 + 31, 17 + 29 + 32, 17 + 29 + 33, 17 + 29 + 34, 17 + 29 + 35, 17 + 29 + 36, 17 + 29 + 37. |
| 30 | 17 + 30 + 31, 17 + 30 + 32, 17 + 30 + 33, 17 + 30 + 34, 17 + 30 + 35, 17 + 30 + 36, 17 + 30 + 37. |
| 31 | 17 + 31 + 32, 17 + 31 + 33, 17 + 31 + 34, 17 + 31 + 35, 17 + 31 + 36, 17 + 31 + 37. |
| 32 | 17 + 32 + 33, 17 + 32 + 34, 17 + 32 + 35, 17 + 32 + 36, 17 + 32 + 37. |
| 33 | 17 + 33 + 34, 17 + 33 + 35, 17 + 33 + 36, 17 + 33 + 37. |
| 34 | 17 + 34 + 35, 17 + 34 + 36, 17 + 34 + 37. |
| 35 | 17 + 35 + 36, 17 + 35 + 37. |
| 36 | 17 + 36 + 37. |

TABLE 18

Myrcene family of terpene formulations.
The numbers refer to the terpenes from Table 1.
The designation "family" is only for convenience in presentation,
as other tabes also include formulations with myrcene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 19 | 18 + 19 + 20, 18 + 19 + 21, 18 + 19 + 22, 18 + 19 + 23, 18 + 19 + 24, 18 + 19 + 25, 18 + 19 + 26, 18 + 19 + 27, 18 + 19 + 28, 18 + 19 + 29, 18 + 19 + 30, 18 + 19 + 31, 18 + 19 + 32, 18 + 19 + 33, 18 + 19 + 34, 18 + 19 + 35, 18 + 19 + 36, 18 + 19 + 37. |
| 20 | 18 + 20 + 21, 18 + 20 + 22, 18 + 20 + 23, 18 + 20 + 24, 18 + 20 + 25, 18 + 20 + 26, 18 + 20 + 27, 18 + 20 + 28, 18 + 20 + 29, 18 + 20 + 30, 18 + 20 + 31, 18 + 20 + 32, 18 + 20 + 33, 18 + 20 + 34, 18 + 20 + 35, 18 + 20 + 36, 18 + 20 + 37. |
| 21 | 18 + 21 + 22, 18 + 21 + 23, 18 + 21 + 24, 18 + 21 + 25, 18 + 21 + 26, 18 + 21 + 27, 18 + 21 + 28, 18 + 21 + 29, 18 + 21 + 30, 18 + 21 + 31, 18 + 21 + 32, 18 + 21 + 33, 18 + 21 + 34, 18 + 21 + 35, 18 + 21 + 36, 18 + 21 + 37. |
| 22 | 18 + 22 + 23, 18 + 22 + 24, 18 + 22 + 25, 18 + 22 + 26, 18 + 22 + 27, 18 + 22 + 28, 18 + 22 + 29, 18 + 22 + 30, 18 + 22 + 31, 18 + 22 + 32, 18 + 22 + 33, 18 + 22 + 34, 18 + 22 + 35, 18 + 22 + 36, 18 + 22 + 37. |
| 23 | 18 + 23 + 24, 18 + 23 + 25, 18 + 23 + 26, 18 + 23 + 27, 18 + 23 + 28, 18 + 23 + 29, 18 + 23 + 30, 18 + 23 + 31, |

TABLE 18-continued

Myrcene family of terpene formulations.
The numbers refer to the terpenes from Table 1.
The designation "family" is only for convenience in presentation,
as other tabes also include formulations with myrcene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
|  | 18 + 23 + 32, 18 + 23 + 33, 18 + 23 + 34, 18 + 23 + 35, 18 + 23 + 36, 18 + 23 + 37. |
| 24 | 18 + 24 + 25, 18 + 24 + 26, 18 + 24 + 27, 18 + 24 + 28, 18 + 24 + 29, 18 + 24 + 30, 18 + 24 + 31, 18 + 24 + 32, 18 + 24 + 33, 18 + 24 + 34, 18 + 24 + 35, 18 + 24 + 36, 18 + 24 + 37. |
| 25 | 18 + 25 + 26, 18 + 25 + 27, 18 + 25 + 28, 18 + 25 + 29, 18 + 25 + 30, 18 + 25 + 31, 18 + 25 + 32, 18 + 25 + 33, 18 + 25 + 34, 18 + 25 + 35, 18 + 25 + 36, 18 + 25 + 37. |
| 26 | 18 + 26 + 27, 18 + 26 + 28, 18 + 26 + 29, 18 + 26 + 30, 18 + 26 + 31, 18 + 26 + 32, 18 + 26 + 33, 18 + 26 + 34, 18 + 26 + 35, 18 + 26 + 36, 18 + 26 + 37. |
| 27 | 18 + 27 + 28, 18 + 27 + 29, 18 + 27 + 30, 18 + 27 + 31, 18 + 27 + 32, 18 + 27 + 33, 18 + 27 + 34, 18 + 27 + 35, 18 + 27 + 36, 18 + 27 + 37. |
| 28 | 18 + 28 + 29, 18 + 28 + 30, 18 + 28 + 31, 18 + 28 + 32, 18 + 28 + 33, 18 + 28 + 34, 18 + 28 + 35, 18 + 28 + 36, 18 + 28 + 37. |
| 29 | 18 + 29 + 30, 18 + 29 + 31, 18 + 29 + 32, 18 + 29 + 33, 18 + 29 + 34, 18 + 29 + 35, 18 + 29 + 36, 18 + 29 + 37. |
| 30 | 18 + 30 + 31, 18 + 30 + 32, 18 + 30 + 33, 18 + 30 + 34, 18 + 30 + 35, 18 + 30 + 36, 18 + 30 + 37. |
| 31 | 18 + 31 + 32, 18 + 31 + 33, 18 + 31 + 34, 18 + 31 + 35, 18 + 31 + 36, 18 + 31 + 37. |
| 32 | 18 + 32 + 33, 18 + 32 + 34, 18 + 32 + 35, 18 + 32 + 36, 18 + 32 + 37. |
| 33 | 18 + 33 + 34, 18 + 33 + 35, 18 + 33 + 36, 18 + 33 + 37. |
| 34 | 18 + 34 + 35, 18 + 34 + 36, 18 + 34 + 37. |
| 35 | 18 + 35 + 36, 18 + 35 + 37. |
| 36 | 18 + 36 + 37. |

TABLE 19

Nerol family of terpene formulations.
The numbers refer to the terpenes from Table 1.
The designation "family" is only for convenience in presentation,
as other tables also include formulations with nerol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 20 | 19 + 20 + 21, 19 + 20 + 22, 19 + 20 + 23, 19 + 20 + 24, 19 + 20 + 25, 19 + 20 + 26, 19 + 20 + 27, 19 + 20 + 28, 19 + 20 + 29, 19 + 20 + 30, 19 + 20 + 31, 19 + 20 + 32, 19 + 20 + 33, 19 + 20 + 34, 19 + 20 + 35, 19 + 20 + 36, 19 + 20 + 37. |
| 21 | 19 + 21 + 22, 19 + 21 + 23, 19 + 21 + 24, 19 + 21 + 25, 19 + 21 + 26, 19 + 21 + 27, 19 + 21 + 28, 19 + 21 + 29, 19 + 21 + 30, 19 + 21 + 31, 19 + 21 + 32, 19 + 21 + 33, 19 + 21 + 34, 19 + 21 + 35, 19 + 21 + 36, 19 + 21 + 37. |
| 22 | 19 + 22 + 23, 19 + 22 + 24, 19 + 22 + 25, 19 + 22 + 26, 19 + 22 + 27, 19 + 22 + 28, 19 + 22 + 29, 19 + 22 + 30, 19 + 22 + 31, 19 + 22 + 32, 19 + 22 + 33, 19 + 22 + 34, 19 + 22 + 35, 19 + 22 + 36, 19 + 22 + 37. |
| 23 | 19 + 23 + 24, 19 + 23 + 25, 19 + 23 + 26, 19 + 23 + 27, 19 + 23 + 28, 19 + 23 + 29, 19 + 23 + 30, 19 + 23 + 31, 19 + 23 + 32, 19 + 23 + 33, 19 + 23 + 34, 19 + 23 + 35, 19 + 23 + 36, 19 + 23 + 37. |
| 24 | 19 + 24 + 25, 19 + 24 + 26, 19 + 24 + 27, 19 + 24 + 28, 19 + 24 + 29, 19 + 24 + 30, 19 + 24 + 31, 19 + 24 + 32, 19 + 24 + 33, 19 + 24 + 34, 19 + 24 + 35, 19 + 24 + 36, 19 + 24 + 37. |

TABLE 19-continued

Nerol family of terpene formulations.
The numbers refer to the terpenes from Table 1.
The designation "family" is only for convenience in presentation,
as other tables also include formulations with nerol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 25 | 19 + 25 + 26, 19 + 25 + 27, 19 + 25 + 28, 19 + 25 + 29, 19 + 25 + 30, 19 + 25 + 31, 19 + 25 + 32, 19 + 25 + 33, 19 + 25 + 34, 19 + 25 + 35, 19 + 25 + 36, 19 + 25 + 37. |
| 26 | 19 + 26 + 27, 19 + 26 + 28, 19 + 26 + 29, 19 + 26 + 30, 19 + 26 + 31, 19 + 26 + 32, 19 + 26 + 33, 19 + 26 + 34, 19 + 26 + 35, 19 + 26 + 36, 19 + 26 + 37. |
| 27 | 19 + 27 + 28, 19 + 27 + 29, 19 + 27 + 30, 19 + 27 + 31, 19 + 27 + 32, 19 + 27 + 33, 19 + 27 + 34, 19 + 27 + 35, 19 + 27 + 36, 19 + 27 + 37. |
| 28 | 19 + 28 + 29, 19 + 28 + 30, 19 + 28 + 31, 19 + 28 + 32, 19 + 28 + 33, 19 + 28 + 34, 19 + 28 + 35, 19 + 28 + 36, 19 + 28 + 37. |
| 29 | 19 + 29 + 30, 19 + 29 + 31, 19 + 29 + 32, 19 + 29 + 33, 19 + 29 + 34, 19 + 29 + 35, 19 + 29 + 36, 19 + 29 + 37. |
| 30 | 19 + 30 + 31, 19 + 30 + 32, 19 + 30 + 33, 19 + 30 + 34, 19 + 30 + 35, 19 + 30 + 36, 19 + 30 + 37. |
| 31 | 19 + 31 + 32, 19 + 31 + 33, 19 + 31 + 34, 19 + 31 + 35, 19 + 31 + 36, 19 + 31 + 37. |
| 32 | 19 + 32 + 33, 19 + 32 + 34, 19 + 32 + 35, 19 + 32 + 36, 19 + 32 + 37. |
| 33 | 19 + 33 + 34, 19 + 33 + 35, 19 + 33 + 36, 19 + 33 + 37. |
| 34 | 19 + 34 + 35, 19 + 34 + 36, 19 + 34 + 37. |
| 35 | 19 + 35 + 36, 19 + 35 + 37. |
| 36 | 19 + 36 + 37. |

TABLE 20

Cis-ocimene family of terpene formulations.
The numbers refer to the terpenes from Table 1.
The designation "family" is only for convenience in presentation,
as other tables also include formulatons with cis-ocimene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 21 | 20 + 21 + 22, 20 + 21 + 23, 20 + 21 + 24, 20 + 21 + 25, 20 + 21 + 26, 20 + 21 + 27, 20 + 21 + 28, 20 + 21 + 29, 20 + 21 + 30, 20 + 21 + 31, 20 + 21 + 32, 20 + 21 + 33, 20 + 21 + 34, 20 + 21 + 35, 20 + 21 + 36, 20 + 21 + 37. |
| 22 | 20 + 22 + 23, 20 + 22 + 24, 20 + 22 + 25, 20 + 22 + 26, 20 + 22 + 27, 20 + 22 + 28, 20 + 22 + 29, 20 + 22 + 30, 20 + 22 + 31, 20 + 22 + 32, 20 + 22 + 33, 20 + 22 + 34, 20 + 22 + 35, 20 + 22 + 36, 20 + 22 + 37. |
| 23 | 20 + 23 + 24, 20 + 23 + 25, 20 + 23 + 26, 20 + 23 + 27, 20 + 23 + 28, 20 + 23 + 29, 20 + 23 + 30, 20 + 23 + 31, 20 + 23 + 32, 20 + 23 + 33, 20 + 23 + 34, 20 + 23 + 35, 20 + 23 + 36, 20 + 23 + 37. |
| 24 | 20 + 24 + 25, 20 + 24 + 26, 20 + 24 + 27, 20 + 24 + 28, 20 + 24 + 29, 20 + 24 + 30, 20 + 24 + 31, 20 + 24 + 32, 20 + 24 + 33, 20 + 24 + 34, 20 + 24 + 35, 20 + 24 + 36, 20 + 24 + 37. |
| 25 | 20 + 25 + 26, 20 + 25 + 27, 20 + 25 + 28, 20 + 25 + 29, 20 + 25 + 30, 20 + 25 + 31, 20 + 25 + 32, 20 + 25 + 33, 20 + 25 + 34, 20 + 25 + 35, 20 + 25 + 36, 20 + 25 + 37. |
| 26 | 20 + 26 + 27, 20 + 26 + 28, 20 + 26 + 29, 20 + 26 + 30, 20 + 26 + 31, 20 + 26 + 32, 20 + 26 + 33, 20 + 26 + 34, 20 + 26 + 35, 20 + 26 + 36, 20 + 26 + 37. |
| 27 | 20 + 27 + 28, 20 + 27 + 29, 20 + 27 + 30, 20 + 27 + 31, 20 + 27 + 32, 20 + 27 + 33, 20 + 27 + 34, 20 + 27 + 35, 20 + 27 + 36, 20 + 27 + 37. |
| 28 | 20 + 28 + 29, 20 + 28 + 30, 20 + 28 + 31, 20 + 28 + 32, 20 + 28 + 33, 20 + 28 + 34, 20 + 28 + 35, 20 + 28 + 36, 20 + 28 + 37. |
| 29 | 20 + 29 + 30, 20 + 29 + 31, 20 + 29 + 32, 20 + 29 + 33, 20 + 29 + 34, 20 + 29 + 35, 20 + 29 + 36, 20 + 29 + 37. |
| 30 | 20 + 30 + 31, 20 + 30 + 32, 20 + 30 + 33, 20 + 30 + 34, 20 + 30 + 35, 20 + 30 + 36, 20 + 30 + 37. |
| 31 | 20 + 31 + 32, 20 + 31 + 33, 20 + 31 + 34, 20 + 31 + 35, 20 + 31 + 36, 20 + 31 + 37. |
| 32 | 20 + 32 + 33, 20 + 32 + 34, 20 + 32 + 35, 20 + 32 + 36, 20 + 32 + 37. |
| 33 | 20 + 33 + 34, 20 + 33 + 35, 20 + 33 + 36, 20 + 33 + 37. |
| 34 | 20 + 34 + 35, 20 + 34 + 36, 20 + 34 + 37. |
| 35 | 20 + 35 + 36, 20 + 35 + 37. |
| 36 | 20 + 36 + 37. |

TABLE 21

Trans-ocimene family of terpene formulations.
The numbers refer to the terpenes from Table 1.
The designation "family" is only
for convenience in presentation, as other tables also include
formulations with trans-ocimene.

| Sub-family | Each disclosure of three terpenes represents a distinct formulation. in one embodiment, the formulation that is described by the indicated mixture of the three terpenes does not include any additional terpenes. In other embodiments, it does include additional terpenes. |
|---|---|
| 22 | 21 + 22 + 23, 21 + 22 + 24, 21 + 22 + 25, 21 + 22 + 26, 21 + 22 + 27, 21 + 22 + 28, 21 + 22 + 29, 21 + 22 + 30, 21 + 22 + 31, 21 + 22 + 32, 21 + 22 + 33, 21 + 22 + 34, 21 + 22 + 35, 21 + 22 + 36, 21 + 22 + 37. |
| 23 | 21 + 23 + 24, 21 + 23 + 25, 21 + 23 + 26, 21 + 23 + 27, 21 + 23 + 28, 21 + 23 + 29, 21 + 23 + 30, 21 + 23 + 31, 21 + 23 + 32, 21 + 23 + 33, 21 + 23 + 34, 21 + 23 + 35, 21 + 23 + 36, 21 + 23 + 37. |
| 24 | 21 + 24 + 25, 21 + 24 + 26, 21 + 24 + 27, 21 + 24 + 28, 21 + 24 + 29, 21 + 24 + 30, 21 + 24 + 31, 21 + 24 + 32, 21 + 24 + 33, 21 + 24 + 34, 21 + 24 + 35, 21 + 24 + 36, 21 + 24 + 37. |
| 25 | 21 + 25 + 26, 21 + 25 + 27, 21 + 25 + 28, 21 + 25 + 29, 21 + 25 + 30, 21 + 25 + 31, 21 + 25 + 32, 21 + 25 + 33, 21 + 25 + 34, 21 + 25 + 35, 21 + 25 + 36, 21 + 25 + 37. |
| 26 | 21 + 26 + 27, 21 + 26 + 28, 21 + 26 + 29, 21 + 26 + 30, 21 + 26 + 31, 21 + 26 + 32, 21 + 26 + 33, 21 + 26 + 34, 21 + 26 + 35, 21 + 28 + 36, 21 + 26 + 37. |
| 27 | 21 + 27 + 28, 21 + 27 + 29, 21 + 27 + 30, 21 + 27 + 31, 21 + 27 + 32, 21 + 27 + 33, 21 + 27 + 34, 21 + 27 + 35, 21 + 27 + 36, 21 + 27 + 37. |
| 28 | 21 + 28 + 29, 21 + 28 + 30, 21 + 28 + 31, 21 + 28 + 32, 21 + 28 + 33, 21 + 28 + 34, 21 + 28 + 35, 21 + 28 + 36, 21 + 28 + 37. |
| 29 | 21 + 29 + 30, 21 + 29 + 31, 21 + 29 + 32, 21 + 29 + 33, 21 + 29 + 34, 21 + 29 + 35, 21 + 29 + 36, 21 + 29 + 37. |
| 30 | 21 + 30 + 31, 21 + 30 + 32, 21 + 30 + 33, 21 + 30 + 34, 21 + 30 + 35, 21 + 30 + 36, 21 + 30 + 37. |
| 31 | 21 + 31 + 32, 21 + 31 + 33, 21 + 31 + 34, 21 + 31 + 35, 21 + 31 + 36, 21 + 31 + 37. |
| 32 | 21 + 32 + 33, 21 + 32 + 34, 21 + 32 + 35, 21 + 32 + 36, 21 + 32 + 37. |
| 33 | 21 + 33 + 34, 21 + 33 + 35, 21 + 33 + 36, 21 + 33 + 37. |
| 34 | 21 + 34 + 35, 21 + 34 + 36, 21 + 34 + 37. |
| 35 | 21 + 35 + 36, 21 + 35 + 37. |
| 36 | 21 + 36 + 37. |

TABLE 22

Alpha-phellandrene family of terpene formulations.
The numbers refer to the terpenes from Table 1.
The designation "family" is only for
convenience in presentation as other tables also include formulations
with alpha-phellandrene.

Each disclosure of three terpenes represents a distinct formulation.
In one embodiment, the formulation that is described by the indicated mixture of the three terpenes does not include any additional terpenes. In other embodiments, it does include additional terpenes.

| Sub-family | |
|---|---|
| 23 | 22 + 23 + 24, 22 + 23 + 25, 22 + 23 + 26, 22 + 23 + 27, 22 + 23 + 28, 22 + 23 + 29, 22 + 23 + 30, 22 + 23 + 31, 22 + 23 + 32, 22 + 23 + 33, 22 + 23 + 34, 22 + 23 + 35, 22 + 23 + 36, 22 + 23 + 37. |
| 24 | 22 + 24 + 25, 22 + 24 + 26, 22 + 24 + 27, 22 + 24 + 28, 22 + 24 + 29, 22 + 24 + 30, 22 + 24 + 31, 22 + 24 + 32, 22 + 24 + 33, 22 + 24 + 34, 22 + 24 + 35, 22 + 24 + 36, 22 + 24 + 37. |
| 25 | 22 + 25 + 26, 22 + 25 + 27, 22 + 25 + 28, 22 + 25 + 29, 22 + 25 + 30, 22 + 25 + 31, 22 + 25 + 32, 22 + 25 + 33, 22 + 25 + 34, 22 + 25 + 35, 22 + 25 + 36, 22 + 25 + 37. |
| 26 | 22 + 26 + 27, 22 + 26 + 28, 22 + 26 + 29, 22 + 26 + 30, 22 + 26 + 31, 22 + 26 + 32, 22 + 26 + 33, 22 + 26 + 34, 22 + 26 + 35, 22 + 26 + 36, 22 + 26 + 37. |
| 27 | 22 + 27 + 28, 22 + 27 + 29, 22 + 27 + 30, 22 + 27 + 31, 22 + 27 + 32, 22 + 27 + 33, 22 + 27 + 34, 22 + 27 + 35, 22 + 27 + 36, 22 + 27 + 37. |
| 28 | 22 + 28 + 29, 22 + 28 + 30, 22 + 28 + 31, 22 + 28 + 32, 22 + 28 + 33, 22 + 28 + 34, 22 + 28 + 35, 22 + 28 + 36, 22 + 28 + 37. |
| 29 | 22 + 29 + 30, 22 + 29 + 31, 22 + 29 + 32. 22 + 29 + 33. 22 + 29 + 34, 22 + 29 + 35, 22 + 29 + 36, 22 + 29 + 37 |
| 30 | 22 + 30 + 31, 22 + 30 + 32, 22 + 30 + 33, 22 + 30 + 34, 22 + 30 + 35, 22 + 30 + 36, 22 + 30 + 37. |
| 31 | 22 + 31 + 32, 22 + 31 + 33, 22 + 31 + 34, 22 + 31 + 35, 22 + 31 + 36, 22 + 31 + 37. |
| 32 | 22 + 32 + 33, 22 + 32 + 34, 22 + 32 + 35, 22 + 32 + 36, 22 + 32 + 37. |
| 33 | 22 + 33 + 34, 22 + 33 + 35, 22 + 33 + 36, 22 + 33 + 37. |
| 34 | 22 + 34 + 35, 22 + 34 + 36, 22 + 34 + 37. |
| 35 | 22 + 35 + 36, 22 + 35 + 37. |
| 36 | 22 + 36 + 37. |

TABLE 23

Alpha-pinene family of terpene formulations.
The numbers refer to the terpenes from Table 1.
The designation "family"
is only for convenience in presentation as other tables
also include formulations with alpha-pinene.

Each disclosure of three terpenes represents a distinct formulation.
In one embodiment, the formulation that is described by the indicated mixture of the three terpenes does not include any additional terpenes. In other embodiments, if does include additional terpenes.

| Sub-family | |
|---|---|
| 24 | 23 + 24 + 25, 23 + 24 + 26, 23 + 24 + 27, 23 + 24 + 28, 23 + 24 + 29, 23 + 24 + 30, 23 + 24 + 31, 23 + 24 + 32, 23 + 24 + 33, 23 + 24 + 34, 23 + 24 + 35, 23 + 24 + 36, 23 + 24 + 37. |
| 25 | 23 + 25 + 26, 23 + 25 + 27, 23 + 25 + 28, 23 + 25 + 29, 23 + 25 + 30, 23 + 25+ 31, 23 + 25 + 32, 23, + 25 + 33, 23 + 25 + 34, 23 + 25 + 35, 23 + 25 + 36, 23 + 25 + 37. |
| 26 | 23 + 26 + 27, 23 + 26 + 28, 23 + 26 + 29, 23 + 26 + 30, 23 + 28 + 31, 23 + 26 + 32, 23 + 26 + 33, 23 + 26 + 34, 23 + 26 + 35, 23 + 26 + 36, 23 + 26 + 37. |
| 27 | 23 + 27 + 28, 23 + 27 + 29, 23 + 27 + 30, 23 + 27 + 31, 23 + 27 + 32, 23 + 27 + 33, 23 + 27 + 34, 23 + 27 + 35, 23 + 27 + 36, 23 + 27 + 37. |
| 28 | 23 + 28 + 29, 23 + 28 + 30, 23 + 28 + 31, 23 + 28 + 32, 23 + 28 + 33, 23 + 28 + 34, 23 + 28 + 35, 23 + 28 + 36, 23 + 28 + 37. |
| 29 | 23 + 29 + 30, 23 + 29 + 31, 23 + 29 + 32, 23 + 29 + 33, 23 + 29 + 34, 23 + 29 + 35, 23 + 29 + 36, 23 + 29 + 37. |
| 30 | 23 + 30 + 31, 23 + 30 + 32, 23 + 30 + 33, 23 + 30 + 34, 23 + 30 + 35, 23 + 30 + 36, 23 + 30 + 37. |
| 31 | 23 + 31 + 32, 23 + 31 + 33, 23 + 31 + 34, 23 + 31 + 35, 23 + 31 + 36, 23 + 31 +37. |
| 32 | 23 + 32 + 33, 23 + 32 + 34, 23 + 32 + 35, 23 + 32 + 36, 23 + 32 + 37. |
| 33 | 23 + 33 + 34, 23 + 33 + 35, 23 + 33 + 36, 23 + 33 + 37. |
| 34 | 23 + 34 + 35, 23 + 34 + 36, 23 + 34 + 37. |
| 35 | 23 + 35 + 36, 23 + 35 + 37. |
| 36 | 23 + 36 + 37. |

TABLE 24

Beta-pinene family of terpene formulations.
The numbers refer to the terpenes from Table 1.
The designation "family" is only
for convenience in presentation, as other tables
also include formulations with beta-pinene Each disclosure of three terpenes represents a distinct formulation,
In one embodiment, the formulation that is described by the 1, indicated mixture of the three terpenes does not include any 1 additional terpenes, In other embodiments, It does include additional terpenes.

| Sub-family | |
|---|---|
| 25 | 24 + 25 + 26, 24 + 25 + 27, 24 + 25 + 28, 24 + 25 + 29, 24 + 25 + 30, 24 + 25 + 31, 24 + 25 + 32, 24 + 25 + 33, 24 + 25 + 34, 24 + 25 + 35, 24 + 25 + 36, 24 + 25 + 37. |
| 26 | 24 + 26 + 27, 24 + 26 + 28, 24 + 26 + 29, 24 + 26 + 30, 24 + 26 + 31, 24 + 26 + 32, 24 + 26 + 33, 24 + 26 + 35, 24 + 26 + 36, 24 + 26 + 37. |
| 27 | 24 + 27 + 28, 24 + 27 + 29, 24 + 27 + 30, 24 + 27 + 31, 24 + 27 + 32, 24 + 27 + 33, 24 + 27 + 34, 24 + 27 + 35, 24 + 27 + 36, 24 + 27 + 37. |
| 28 | 24 + 28 + 29, 24 + 28 + 30, 24 + 28 + 31, 24 + 28 + 32, 24 + 28 + 33, 24 + 28 + 34, 24 + 28 + 35, 24 + 28 + 36, 24 + 28 + 37. |
| 29 | 24 + 29 + 30, 24 + 29 + 31, 24 + 29 + 32, 24 + 29 + 33, 24 + 29 + 34, 24 + 29 + 35, 24 + 29 + 36, 24 + 29 + 37. |
| 30 | 24 + 30 + 31, 24 + 30 + 32, 24 + 30 + 33, 24 + 30 + 34, 24 + 30 + 35, 24 + 30 + 36, 24 + 30 + 37. |
| 31 | 24 + 31 + 32, 24 + 31 + 33, 24 + 31 + 34, 24 + 31 + 35, 24 + 31 + 36, 24 + 31 + 37. |
| 32 | 24 + 32 + 33, 24 + 32 + 34, 24 + 32 + 35, 24 + 32 + 36, 24 + 32 + 37. |
| 33 | 24 + 33 + 34, 24 + 33 + 35, 24 + 33 + 36, 24 + 33 + 37. |
| 34 | 24 + 34 + 35, 24 + 34 + 36, 24 + 34 + 37. |
| 35 | 24 + 35 + 36, 24 + 35 + 37. |
| 36 | 24 + 36 + 37. |

TABLE 25

Sabinene family of terpene formulations.
The numbers refer to the terpenes from Table 1.
The designation "family" is only for convenience
in presentation, as other tables also include formulations with sabinene.

Each disclosure of three terpenes represents a distinct formulation.
In one embodiment, the formulation that is described by the indicated mixture of the three terpenes does not include any additional terpenes. In other embodiments, it does include additional terpenes

| Sub-family | |
|---|---|
| 26 | 25 + 26 + 27, 25 + 26 + 28, 25 + 26 + 29, 25 + 26 + 30, 25 + 26 + 31, 25 + 26 + 32, 25 + 26 + 33, 25 + 26 + 34, 25 + 26 + 35, 25 + 26 + 36, 25 + 26 + 37. |
| 27 | 25 + 27 + 28, 25 + 27 + 29, 25 + 27 + 30, 25 + 27 + 31, 25 + 27 + 32, 25 + 27 + 33, 25 + 27 + 34, 25 + 27 + 35, 25 + 27 + 36, 25 + 27 + 37. |
| 28 | 25 + 28 + 29, 25 + 28 + 30, 25 + 28 + 31, 25 + 28 + 32, 25 + 28 + 33, 25 + 28 + 34, 25 + 28 + 35, 25 + 28 + 36, 25 + 28 + 37. |
| 29 | 25 + 29 + 30, 25 + 29 + 31, 25 + 28 + 32, 25 + 29 + 33, 25 + 29 + 34, 25 + 29 + 35, 25 + 29 + 36, 25 + 29 + 37. |
| 30 | 25 + 30 + 31, 25 + 30 + 32, 25 + 30 + 33, 25 + 30 + 34, 25 + 30 + 35, 25 + 30 + 36, 25 + 30 + 37. |
| 31 | 25 + 31 + 32, 25 + 31 + 33, 25 + 31 + 34, 25 + 31 + 35, 25 + 31 + 36, 25 + 31 + 37. |
| 32 | 25 + 32 + 33, 25 + 32 + 34, 25 + 32 + 35, 25 + 32 + 36, 25 + 32 + 37. |
| 33 | 25 + 33 + 34, 25 + 33 + 35, 25 + 33 + 36, 25 + 33 + 37. |
| 34 | 25 + 34 + 35, 25 + 34 + 36, 25 + 34 + 37. |
| 35 | 25 + 35 + 36, 25 + 35 + 37. |
| 36 | 25 + 36 + 37. |

TABLE 26

Alpha-terpinene family of terpene formulations.
The numbers refer to the terpenes from Table 1.
The designation "family" is only for convenience in presentation, as other tables also include formulations with alpha-terpinene.

Each disclosure of three terpenes represents a distinct formulation.
In one embodiment, the formulation that is described by the indicated mixture of the three terpenes does not include any additional terpenes. In other embodiments, it does include additional terpenes.

| Sub-family | |
|---|---|
| 27 | 26 + 27 + 28, 26 + 27 + 29, 26 + 27 + 30, 28 + 27 + 31, 26 + 27 + 32, 26 + 27 + 33, 26 + 27 + 34, 26 + 27 + 35, 26 + 27 + 36, 26 + 27 + 37. |
| 28 | 26 + 28 + 29, 26 + 28 + 30, 26 + 28 + 31, 26 + 28 + 32, 26 + 28 + 33, 26 + 28 + 34, 26 + 28 + 35, 26 + 28 + 36, 26 + 28 + 37. |
| 29 | 26 + 29 + 30, 26 + 29 + 31, 26 + 29 + 32, 26 + 29 + 33, 26 + 29 + 34, 26 + 29 + 35, 26 + 29+ 36, 26 + 29 + 37. |
| 30 | 26 + 30 + 31, 26 + 30 + 32, 26 + 30 + 33, 26 + 30 + 34, 26 + 30 + 35, 26 + 30 + 36, 26 + 30 + 37. |
| 31 | 26 + 31 + 32, 26 + 31 + 33, 26 + 31 + 34, 26 + 31 + 35, 26 + 31 + 36, 26 + 31 + 37. |
| 32 | 26 + 32 + 33, 26 + 32 + 34, 26 + 32 + 35, 26 + 32 + 36, 26 + 32 + 37. |
| 33 | 26 + 33 + 34, 26 + 33 + 35, 26 + 33 + 36, 26 + 33 + 37. |
| 34 | 26 + 34 + 35, 26 + 34 + 36, 26 + 34 + 37. |
| 35 | 26 + 35 + 36, 26 + 35 + 37. |
| 36 | 26 + 36 + 37 |

TABLE 27

Alpha-terpineol family of terpene formulations.
The numbers refer to the terpenes from Table 1.
The designation "family" is only for convenience in presentation, as other tables also include formulations with alpha-terpineol.

Each disclosure of three terpenes represents a distinct formulation.
In one embodiment, the formulation that is described by the indicated mixture of the three terpenes does not include any additional terpenes. In other embodiments, it does include additional terpenes.

| Sub-family | |
|---|---|
| 28 | 27 + 28 + 29, 27 + 28 + 30, 27 + 28 + 31, 27 + 28 + 32, 27 + 28 + 33, 27 + 28 + 34, 27 + 28 + 35, 27 + 28 + 36, 27 + 28 + 37. |
| 29 | 27 + 29 + 30, 27 + 29 + 31, 27 + 29 + 32, 27 + 29 + 33, 27 + 29 + 34, 27 + 29 + 35, 27 + 29 + 36, 27 + 29 + 37. |
| 30 | 27 + 30 + 31, 27 + 30 + 32, 27 + 30 + 33, 27 + 30 + 34, 27 + 30 + 35, 27 + 30 + 36, 27 + 30 + 37. |
| 31 | 27 + 31 + 32, 27 + 31 + 33, 27+ 31 + 34, 27 + 31 + 35, 27 + 31 + 36, 27 + 31 + 37. |
| 32 | 27 + 32 + 33, 27 + 32 + 34, 27 + 32 + 35, 27 + 32 + 36, 27 + 32 + 37. |
| 33 | 27 + 33 + 34, 27 + 33 + 35, 27 + 33 + 36, 27 + 33 + 37. |
| 34 | 27 + 34 + 35, 27 + 34 + 36, 27 + 34 + 37 |
| 35 | 27 + 35 + 36, 27 + 35 + 37. |
| 36 | 27 + 38 + 37. |

TABLE 28

Terpinolene family of terpene formulations.
The numbers refer to the terpenes from Table 1.
The designation "family" is only for convenience in presentation, as other tables also include formulations with terpinolene.

Each disclosure of three terpenes represents a distinct formulation.
In one embodlinent, the formulation that is described by the indicated mixture of the three terpenes does not include any additional terpenes. In other embodiments, it does include additional terpenes.

| Sub-family | |
|---|---|
| 29 | 28 + 29 + 30, 28 + 29 + 31, 28 + 29 + 32, 28 + 29 + 33, 28 + 29 + 34, 28 + 29 + 35, 28 + 29 + 36, 28 + 29 + 37. |
| 30 | 28 + 30 + 31, 28 + 30 + 32, 28 + 30 + 33, 28 + 30 + 34, 28 + 30 + 35, 28 + 30 + 36, 28 + 30 + 37. |
| 31 | 28 + 31 + 32, 28 + 31 + 33, 28 + 31 + 34, 28 + 31 + 35, 28 + 31 + 36, 28 + 31 + 37. |
| 32 | 28 + 32 + 33, 28 + 32 + 34, 28 + 32 + 35, 28 + 32 + 36, 28 + 32 + 37. |
| 33 | 28 + 33 + 34, 28 + 33 + 35, 28 + 33 + 36, 28 + 33 + 37. |
| 34 | 28 + 34 + 35, 28 + 34 + 36, 28 + 34 + 37. |
| 35 | 28 + 35 + 36, 28 + 35 + 37. |
| 36 | 28 + 36 + 37. |

TABLE 29

Alpha-guaiene family of terbene formulations.
The numbers refer to the terpenes from Table 1.
The designation "family" is only for convenience in presentation, as other tables also include formulations with alpha-guaiene.

Each disclosure of three terpenes represents a distinct formulation.
In one embodiment, the formulation that is described by the indicated mixture of the three terpenes does not include any additional terpenes. In other embodiments, it does include additional terpenes.

| Sub-family | |
|---|---|
| 30 | 29 + 30 + 31, 29 + 30 + 32, 29 + 30 + 33, 29 + 30 + 34, 29 + 30 + 35, 29 + 30 + 36, 29 + 30 + 37. |
| 31 | 29 + 31 + 32, 29 + 31 + 33, 29 + 31 + 34, 29 + 31 + 35, 29 + 31 + 36, 29 + 31 + 37. |

TABLE 29-continued

Alpha-guaiene family of terpene formulations.
The numbers refer to the terpenes from Table 1.
The designation
"family" is only for convenience in presentation, as
other tables also include formulations with alpha-guaiene.

Each disclosure of three terpenes represents a distinct formulation.
In one embodiment, the formulation that is described by the indicated mixture of the three terpenes does not include any additional terpenes. In other embodiments, it does include additional terpenes.

| Sub-family | |
|---|---|
| 32 | 29 + 32 + 33, 29 + 32 + 34, 29 + 32 + 35, 29 + 32 + 36, 29 + 32 + 37. |
| 33 | 29 + 33 + 34, 29 + 33 + 35, 29 + 33 + 36, 29 + 33 + 37. |
| 34 | 29 + 34 + 35, 29 + 34 + 36, 29 + 34 + 37. |
| 35 | 29 + 35 + 36, 29 + 35 + 37. |
| 36 | 29 + 36 + 37. |

TABLE 30

Elemene family of terpene formulations.
The numbers refer to the terpenes from Table 1.
The designation "family" is
only for convenience in presentation, as other
tables also include formulations with elemene.

Each disclosure of three terpenes represents a distinct formulation.
In one embodiment, the formulation that is described by the indicated mixture of the three terpenes does not include any additional terpenes. In other embodiments, it does include additional terpenes.

| Sub-family | |
|---|---|
| 31 | 30 + 31 + 32, 30 + 31 + 33, 30 + 31 + 34, 30 + 31 + 35, 30 + 31 + 36, 30 + 31+ 37. |
| 32 | 30 + 32 + 33, 30 + 32 + 34, 30 + 32 + 35, 30 + 32 + 36, 30 + 32 + 37. |
| 33 | 30 + 33 + 34, 30 + 33 + 35, 30 + 33 + 36, 30 + 33 + 37. |
| 34 | 30 + 34 + 35, 30 + 34 + 36, 30 + 34 + 37. |
| 35 | 30 + 35 + 36, 30 + 35 + 37. |
| 38 | 30 + 36 + 37. |

TABLE 31

Farnesene family of terpene formulations.
The numbers refer to the terpenes from Table 1.
The designation "family" is only for convenience
in presentation, as other tables also include for with farnesene.

Each disclosure of three terpenes represents a distinct formulation.
in one embodiment, the formulation that is described by the indicated mixture of the three terpenes does not include any additional terpenes. In other embodiments, it does include additional terpenes.

| Sub-family | |
|---|---|
| 32 | 31 + 32 + 33, 31 + 32 + 34, 31 + 32 + 35, 31 + 32 + 36, 31 + 32 + 37. |
| 33 | 31 + 33 + 34, 31 + 33 + 35, 31 + 33 + 36, 31 + 33 + 37. |
| 34 | 31 + 34 + 35, 31 + 34 + 36, 31 + 34 + 37. |
| 35 | 31 + 35 + 36, 31 + 35 + 37. |
| 36 | 31 + 36 + 37. |

TABLE 32

Germacrene B family of terpene formulations.
The numbers refer to the terpenes from Table 1.
The designation "family"
is only for convenience in presentation, as other
tables also include formulations with germcrene B.

Each disclosure of three terpenes represents a distinct formulation.
In one embodiment, the formulation that is described by the indicated mixture of the three terpenes does not include any additional terpenes. In other embodiments, it does include additional terpenes.

| Sub-family | |
|---|---|
| 33 | 32 + 33 + 34, 32 + 33 + 35, 32 + 33 + 36, 32 + 33 + 37. |
| 34 | 32 + 34 + 35, 32 + 34 + 36, 32 + 34 + 37. |
| 35 | 32 + 35 + 36, 32 + 35 + 37. |
| 36 | 32 + 36 + 37. |

TABLE 33

Guaia-1(10),11-diene family of terpene formulations.
The numbers refer to the terpenes from Table 1.
The designation "family" is
only for convenience in presentation, as other tables also
include formulations with Guaia-1(10),11-diene.

Each disclosure of three terpenes represents a distinct formulation.
In one embodiment, the formulation that is described by the indicated mixture of the three terpenes does not include any additional terpenes. In other embodiments, it does include additional terpenes.

| Sub-family | |
|---|---|
| 34 | 33 + 34 + 35, 33 + 34 + 36, 33 + 34 + 37. |
| 35 | 33 + 35 + 36, 33 + 35 + 37. |
| 36 | 33 + 36 + 37. |

TABLE 34

Trans-2-pinanol family of terpene formulations.
The numbers refer to the terpenes from Table 1.
The designation "family" is
only for convenience in presentation, as other tables
also include formulations with Trans-2-pinanol.

Each disclosure of three terpenes represents a distinct formulation.
In one embodiment, the formulation that is described by the indicated mixture of the three terpenes does not include any additional terpenes. In other embodiments,
it does include additional terpenes.

| Sub-family | |
|---|---|
| 35 | 34 + 35 + 36, 34 + 35 + 37. |
| 36 | 34 + 36 + 37. |

TABLES 35-37

Table 35. Selina-3,7(11)-diene family of terpene formulatons. The numbers refer to the terpenes from Table 1. The designation "family" is only for convenience in presentation, as other tables also include formulations with Selina-3,7(11)-diene.

| Subfamily | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 36 | 35 + 36 + 37. |

| Table 36 | Eudesm-7(11)-en-4-ol. All members a this family are disclosed in the above tables. This means that all possible combinations of three different terpenes, where one of the terpenes is eudesm-7(11)-en-4-ol, are disclosed above. |
|---|---|
| Table 37 | Valencene family. All members of this family are disclosed in the above tables. This means that all possible combinations of three different terpenes, where one of the terpenes is valencene, are disclosed above. |

Non-limiting percentage values (wt./vol.) for three members of any terpene trio are disclosed below. The values listed below are not with respect to the order of terpenes, in any given terpene trio that is disclosed elsewhere in Tables 2-37.

Formulations Consisting of a Terpene Trio and One or More Other Terpenes

The present disclosure provides a composition that comprises a formulation that consists of a terpene trio, as disclosed in Tables 1-37, plus one or more additional terpenes, where none of the one or more additional terpenes are in the trio. This one or more additional terpenes are referred to as "other terpenes." In non-limiting embodiments, the present disclosure provides a composition that is:

1 part trio (wt./vol.) and 0.0 parts other terpenes (wt./vol.); 1 part trio (wt./vol.) and 0.0-0.1 parts other terpenes (wt./vol.); 1 part trio (wt./vol.) and 0.1 parts other terpenes (wt./vol.); 1 part trio (wt./vol.) and 0.2 parts other terpenes (wt./vol.); 1 part trio (wt./vol.) and 0.3 parts other terpenes (wt./vol.); 1 part trio (wt./vol.) and 0.4 parts other terpenes (wt./vol.); 1 part trio (wt./vol.) and 0.5 parts other terpenes (wt./vol.); 1 part trio (wt./vol.) and 0.6 parts other terpenes (wt./vol.); 1 part trio (wt./vol.) and 0.7 parts other terpenes (wt./vol.); 1 part trio (wt./vol.) and 0.8 parts other terpenes (wt./vol.); 1 part trio (wt./vol.) and 0.9 parts other terpenes (wt./vol.); 1 part trio (wt./vol.) and 1.0 parts other terpenes (wt./vol.); 1 part trio (wt./vol.) and 1.5 parts other terpenes (wt./vol.); 1 part trio (wt./vol.) and 2.0 parts other terpenes (wt./vol.); 1 part trio (wt./vol.) and 2.5 parts other terpenes (wt./vol.); 1 part trio (wt./vol.) and 3.0 parts other terpenes (wt./vol.); 1 part trio (wt./vol.) and 3.5 parts other terpenes (wt./vol.); 1 part trio (wt./vol.) and 4.0 parts other terpenes (wt./vol.); 1 part trio (wt./vol.) and 4.5 parts other terpenes (wt./vol.); 1 part trio (wt./vol.) and 5.0 parts other terpenes (wt./vol.); 1 part trio (wt./vol.) and 5.5 parts other terpenes (wt./vol.); 1 part trio (wt./vol.) and 6.0 parts other terpenes (wt./vol.); 1 part trio (wt./vol.) and 6.5 parts other terpenes (wt./vol.); 1 part trio (wt./vol.) and 7.0 parts other terpenes (wt./vol.); 1 part trio (wt./vol.) and 7.5 parts other terpenes (wt./vol.); 1 part trio (wt./vol.) and 8.0 parts other terpenes (wt./vol.); 1 part trio (wt./vol.) and 8.5 parts other terpenes (wt./vol.); 1 part trio (wt./vol.) and 9.0 parts other terpenes (wt./vol.); 1 part trio (wt./vol.) and 9.5 parts other terpenes (wt./vol.); 1 part trio (wt./vol.) and 10.0 parts other terpenes (wt./vol.); and the like.

The following embodiments track the above embodiments, but with ranges: 1 part trio (wt./vol.) and 0.1-0.2 parts other terpenes (wt./vol.); 1 part trio (wt./vol.) and 0.2-0.3 parts other terpenes (wt./vol.); 1 part trio (wt./vol.) and 0.3-0.4 parts other terpenes (wt./vol.); 1 part trio (wt./vol.) and 0.4-0.5 parts other terpenes (wt./vol.); 1 part trio (wt./vol.) and 0.5-0.6 parts other terpenes (wt./vol.); 1 part trio (wt./vol.) and 0.6-0.7 parts other terpenes (wt./vol.); 1 part trio (wt./vol.) and 0.7-0.8 parts other terpenes (wt./vol.); 1 part trio (wt./vol.) and 0.8-0.9 parts other terpenes (wt./vol.); 1 part trio (wt./vol.) and 0.9-1.0 parts other terpenes (wt./vol.); 1 part trio (wt./vol.) and 1.0-1.5 parts other terpenes (wt./vol.); 1 part trio (wt./vol.) and 1.5-2.0 parts other terpenes (wt./vol.); 1 part trio (wt./vol.) and 2.0-2.5 parts other terpenes (wt./vol.); 1 part trio (wt./vol.) and 2.5-3.0 parts other terpenes (wt./vol.); 1 part trio (wt./vol.) and 3.0-3.5 parts other terpenes (wt./vol.); 1 part trio (wt./vol.) and 3.5-4.0 parts other terpenes (wt./vol.); 1 part trio (wt./vol.) and 4.0-4.5 parts other terpenes (wt./vol.); 1 part trio (wt./vol.) and 4.5-5.0 parts other terpenes (wt./vol.); 1 part trio (wt./vol.) and 5.0-5.5 parts other terpenes (wt./vol.); 1 part trio (wt./vol.) and 5.5-6.0 parts other terpenes (wt./vol.); 1 part trio (wt./vol.) and 6.0-6.5 parts other terpenes (wt./vol.); 1 part trio (wt./vol.) and 6.5-7.0 parts other terpenes (wt./vol.); 1 part trio (wt./vol.) and 7.0-7.5 parts other terpenes (wt./vol.); 1 part trio (wt./vol.) and 7.5-8.0 parts other terpenes (wt./vol.); 1 part trio (wt./vol.) and 8.0-8.5 parts other terpenes (wt./vol.); 1 part trio (wt./vol.) and 8.5-9.0 parts other terpenes (wt./vol.); 1 part trio (wt./vol.) and 9.0-9.5 parts other terpenes (wt./vol.); 1 part trio (wt./vol.) and 9.5-10.0 parts other terpenes (wt./vol.); 1 part trio (wt./vol.) and 10.0-10.5 parts other terpenes (wt./vol.); and the like.

Ratios of the Three Terpenes in the Terpene Trio

In non-limiting embodiments, the present disclosure encompasses a composition that comprises a formulation that includes a terpene trio, e.g., terpene A, terpene B, and terpene C. The designations, A, B, and C, and the affiliated percentages (wt./vol.) do not imply any particular relationship with the terpene trios disclosed above. In other words, the designation "A (10%), B (15%), C (75%)," can be used to refer to each of the following formulations. The goal of this narrative is only to explain the versatility of the "A (xx %), B (xx %), C (xx %)," terminology in applying the fallowing table for describing terpene trios.

BCP (10%); LIM (15%); and MYR (75%).
BCP (10%); MYR (15%); and LIM (75%).
LIM (10%); BCP (15%); and MYR (75%).
MYR (10%); BCP (15%); and LIM (75%).
MYR (10%); LIM (15%); and BCP (75%).
LIM (10%); MYR (15%); and BCP (75%).

The following table (Table 38) can be used to assign percentage values to any terpene trio. In other words, the following table is not limited to terpene trios that consist of BCP, LIM, and MYR.

TABLE 38

Percentage values (wt./vol.) for three members of any terpene trio. The values listed below are not with respect to the order of terpenes, in any given terpene trio that is disclosed elsewhere in this specification.

| A | B | C | A | B | C | A | B | C | A | B | C |
|---|---|---|---|---|---|---|---|---|---|---|---|
| 2 | 5 | 93 | 2 | 10 | 88 | 2 | 15 | 83 | 2 | 20 | 78 |
| 4 | 5 | 91 | 4 | 10 | 86 | 4 | 15 | 81 | 4 | 20 | 76 |
| 5 | 5 | 90 | 5 | 10 | 85 | 5 | 15 | 80 | 5 | 20 | 75 |
| 6 | 5 | 89 | 6 | 10 | 84 | 6 | 15 | 79 | 6 | 20 | 74 |
| 8 | 5 | 87 | 8 | 10 | 82 | 8 | 15 | 77 | 8 | 20 | 72 |
| 10 | 5 | 85 | 10 | 10 | 80 | 10 | 15 | 75 | 10 | 20 | 70 |
| 12 | 5 | 83 | 12 | 10 | 78 | 12 | 15 | 73 | 12 | 20 | 68 |
| 14 | 5 | 81 | 14 | 10 | 76 | 14 | 15 | 71 | 14 | 20 | 66 |
| 16 | 5 | 79 | 16 | 10 | 74 | 16 | 15 | 69 | 15 | 20 | 64 |
| 18 | 5 | 77 | 18 | 10 | 72 | 18 | 15 | 67 | 18 | 20 | 62 |
| 20 | 5 | 75 | 20 | 10 | 70 | 20 | 15 | 65 | 20 | 20 | 60 |
| 25 | 5 | 70 | 25 | 10 | 65 | 25 | 15 | 60 | 25 | 20 | 55 |
| 30 | 5 | 65 | 30 | 10 | 60 | 30 | 15 | 55 | 30 | 20 | 50 |
| 35 | 5 | 60 | 35 | 10 | 55 | 35 | 15 | 50 | 35 | 20 | 45 |
| 40 | 5 | 55 | 40 | 10 | 50 | 40 | 15 | 45 | 40 | 20 | 40 |
| 45 | 5 | 50 | 45 | 10 | 45 | 45 | 15 | 40 | 45 | 20 | 35 |
| 50 | 5 | 45 | 50 | 10 | 40 | 50 | 15 | 35 | 50 | 20 | 30 |

| A | B | C | A | B | C | A | B | C | A | B | C |
|---|---|---|---|---|---|---|---|---|---|---|---|
| 2 | 25 | 73 | 2 | 30 | 68 | 2 | 35 | 63 | 2 | 40 | 58 |
| 4 | 25 | 71 | 4 | 30 | 66 | 4 | 35 | 61 | 4 | 40 | 56 |
| 5 | 25 | 70 | 5 | 30 | 65 | 5 | 35 | 60 | 5 | 40 | 55 |
| 6 | 25 | 69 | 6 | 30 | 64 | 6 | 35 | 59 | 6 | 40 | 54 |
| 8 | 25 | 67 | 8 | 30 | 62 | 8 | 35 | 57 | 8 | 40 | 52 |
| 10 | 25 | 65 | 10 | 30 | 60 | 10 | 35 | 55 | 10 | 40 | 50 |
| 12 | 25 | 63 | 12 | 30 | 58 | 12 | 35 | 53 | 12 | 40 | 48 |
| 14 | 25 | 61 | 14 | 30 | 56 | 14 | 35 | 51 | 14 | 40 | 46 |
| 16 | 25 | 59 | 16 | 30 | 54 | 16 | 35 | 49 | 16 | 40 | 44 |
| 18 | 25 | 57 | 18 | 30 | 52 | 18 | 35 | 47 | 18 | 40 | 42 |
| 20 | 25 | 55 | 20 | 30 | 50 | 20 | 35 | 45 | 20 | 40 | 40 |
| 25 | 25 | 50 | 25 | 30 | 45 | 25 | 35 | 40 | 25 | 40 | 35 |
| 30 | 25 | 45 | 30 | 30 | 40 | 30 | 35 | 35 | 30 | 40 | 30 |
| 35 | 25 | 40 | 35 | 30 | 35 | 35 | 35 | 30 | 35 | 40 | 25 |
| 40 | 25 | 35 | 40 | 30 | 30 | 40 | 35 | 25 | 40 | 40 | 20 |
| 45 | 25 | 30 | 45 | 30 | 25 | 45 | 35 | 20 | 45 | 40 | 15 |
| 50 | 25 | 25 | 50 | 30 | 20 | 50 | 35 | 15 | 50 | 40 | 10 |

| A | B | C | A | B | C | A | B | C | A | B | C |
|---|---|---|---|---|---|---|---|---|---|---|---|
| 2 | 45 | 53 | 10 | 45 | 45 | 20 | 45 | 35 | 45 | 45 | 10 |
| 4 | 45 | 51 | 12 | 45 | 43 | 25 | 45 | 30 | 50 | 45 | 5 |
| 5 | 45 | 50 | 14 | 45 | 41 | 30 | 45 | 25 | | | |
| 6 | 45 | 49 | 16 | 45 | 39 | 35 | 45 | 20 | | | |
| 8 | 45 | 47 | 18 | 45 | 37 | 40 | 45 | 15 | | | |

What is encompassed by the present disclosure are terpene trios of the disclosed values. What is also encompassed are values that are "approximately" the disclosed values. What is further encompassed are values that are in a range halfway between the immediately preceding value and the immediately succeeding value. Redundancies in this table are for stylistic reasons.

While the method and apparatus have been described in terms of what are presently considered to be the mostpractical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial, dependencies only.

Support should be understood to exist to the degree required under new matter laws—including but not limited to United States Patent Law 35 USC § 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value failing within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2, Intel Core Duo, AMD Phenom II X4, Intel Core i5, Intel Core i& Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A liquid composition comprising, in combination:
at least two terpenes; and
one enhancer consisting of isophytol, wherein said at least two terpenes comprise at least one of beta-caryophyllene and myrcene and wherein the liquid composition excludes mint oil.

2. The liquid composition of claim 1, wherein the terpenes are selected from the group consisting alpha-bisabolol, borneol, camphene, camphor, beta-caryophyllene (BCP), delta-3-carene, caryophyllene oxide, alpha-cedrene, beta-eudesmol, fenchol, geraniol (GER), guaiol, alpha-humulene, isoborneol, limonene (LIM), linalool (LIN), menthol, myrcene (MYR), neral, nerolidol (NDL), cis-ocimene, trans-ocimene, alpha-phellandrene, alpha-pinene (API), beta-pinene, sabinene, alpha terpinene, alpha-terpineol, terpinolene, alpha-guaiene, elemene, farnesene, farnesol (FOL), germacrene B, guaia-1(10), 11-diene, trans-2-pinanol, selina-3,7(11)-diene, eudesm-7(11)-en-4-ol, and valencene.

3. The liquid composition of claim 2, comprising approximately equal weight percentages (wt terpene/wt composition) of BCP, LIM, MYR, API and LIN.

4. The liquid composition of claim 2, comprising approximately equal weight percentages (wt terpene/wt composition) of MYR, humulene (HUM, and valencene (VAL).

5. The composition of claim 2, comprising approximately equal weight percentages (wt terpene/wt composition) of NDL, FOL, and LIM.

6. The liquid composition of claim 5, additionally comprising eucalyptol (EUC), LIN, or GER.

7. The liquid composition of claim 1, further comprising propylene glycol, polyethylene glycol (PEG), or glycerin.

8. The liquid composition of claim 1, further comprising water.

9. The liquid composition of claim 1, further comprising hydroxymethyl cellulose, hydroxyethyl cellulose, hydroxypropyl or carboxymethyl cellulose.

10. The liquid composition of claim 1, further comprising vitamin E or isopropyl myristate.

11. The liquid composition of claim 1, comprising 2-99% of at least one enhancer selected from the group consisting of triacetin, isophytol and phytol (wt/wt composition).

12. The liquid composition of claim 11, comprising 2-7% terpenes and 93-98% of one enhancer selected from the group consisting of triacetin, isophytol and phytol.

13. The liquid composition of claim 11, further comprising at least one supplemental constituent element selected from the group consisting essentially of phytol, and isophytol.

14. The liquid composition of claim 12, further comprising at least one supplemental constituent element selected from the group consisting essentially of phytol, and isophytol.

15. The liquid composition of claim 1, wherein the composition is substantially free of ledol.

16. The liquid composition of claim 1, wherein the composition is substantially free of α-terpinene.

17. The liquid composition of claim 1, comprising 1-30% terpenes (wt/wt composition).

18. The liquid composition of claim 1, further comprising a cannabinoid.

19. The liquid composition of claim 18, wherein the cannabinoid is selected from the group consisting of tetrahydrocannabinol, delta-9-tetrahydrocannabinol (THC), delta-8-tetrahydrocannabinol, delta-9-tetrahydrocannabinol propyl analogue (THCV), cannabidiol (CBD), cannabidiol propyl analogs (CBDV), cannabinol (CBN), cannabichromene (CBC), cannabichromene propyl analogs (CBCV) and cannabigerol and their cannabinoid acid counterparts.

20. The liquid composition of claim 18, comprising 2-10% terpenes (wt/wt) and 5-80% triacetin (wt/wt).

21. The liquid composition of claim 20, comprising about 5% terpenes (wt/wt).

22. The liquid composition of claim 20, comprising about 10% triacetin (wt/wt).

23. The liquid composition of claim 18, comprising 5-25% cannabinoid (wt/wt).

24. The liquid composition of claim 18, further comprising propylene glycol, polyethylene glycol (PEG), or glycerin.

25. The liquid composition of claim 18, further comprising a surfactant.

* * * * *